US011723776B2

(12) United States Patent
Segina et al.

(10) Patent No.: US 11,723,776 B2
(45) Date of Patent: Aug. 15, 2023

(54) PERIPROSTHETIC SHOULDER FRACTURE REPAIR

(71) Applicant: Genesis Medical Devices LLC, Indialantic, FL (US)

(72) Inventors: Daniel Nick Segina, Satellite Beach, FL (US); James A. Proctor, Jr., Indialantic, FL (US); James Arthur Proctor, III, Indialantic, FL (US)

(73) Assignee: Genesis Medical Devices LLC, Indialantic, FL (US)

( * ) Notice: Subject to any disclaimer, the term of this patent is extended or adjusted under 35 U.S.C. 154(b) by 389 days.

(21) Appl. No.: 16/887,033

(22) Filed: May 29, 2020

(65) Prior Publication Data

US 2020/0390561 A1  Dec. 17, 2020

Related U.S. Application Data

(63) Continuation of application No. 16/027,605, filed on Jul. 5, 2018, now Pat. No. 10,687,950.
(Continued)

(51) Int. Cl.
*A61F 2/40* (2006.01)
*A61B 17/80* (2006.01)
(Continued)

(52) U.S. Cl.
CPC ........ *A61F 2/4059* (2013.01); *A61B 17/1728* (2013.01); *A61B 17/1753* (2013.01); *A61B 17/80* (2013.01); *A61B 17/8042* (2013.01); *A61B 17/8061* (2013.01); *A61B 17/88* (2013.01); *A61F 2/3607* (2013.01);
(Continued)

(58) Field of Classification Search
CPC ....... A61B 17/80; A61B 17/1778; A61F 2/28; A61F 2/40; A61F 2/4059; A61F 2/4014
See application file for complete search history.

(56) References Cited

U.S. PATENT DOCUMENTS 6,494,913 B1  12/2002  Huebner
9,486,261 B2  11/2016  Plecko et al.
(Continued)

OTHER PUBLICATIONS

Extended European Search Report dated Apr. 14, 2021 for Related European Application No. 18828258.6.

*Primary Examiner* — Jason-Dennis N Stewart
(74) *Attorney, Agent, or Firm* — David J. Thibodeau; VLP Law Group, LLP

(57) ABSTRACT

A periprosthetic fracture repair solution that provides a variety of fracture fixation options should a fracture occur after total hip, knee, or especially a total shoulder arthroplasty, and provides associated methods and apparatus for application of provided fixation. The ability to pre-engineer fracture fixation contingent solutions into humeral components provides for a distinct clinical advantage in the planning and execution for periprosthetic fracture fixation. Said methods and apparatus include targeting devices which allow for intimate association of fixed angle locking screws in pre-drilled holes in an existing prosthetic or other components including additional fixation components. Such apparatus and methods further include the use of alignment devices and other components to allow for ease of repair of periprosthetic fractures utilizing the pre-engineered solutions. Such targeting devices are required in specific circumstances as the prosthetics may prevent x-ray imaging and consequently free hand alignment.

22 Claims, 51 Drawing Sheets

Related U.S. Application Data

(60) Provisional application No. 62/640,378, filed on Mar. 8, 2018, provisional application No. 62/528,675, filed on Jul. 5, 2017.

(51) Int. Cl.
*A61B 17/88* (2006.01)
*A61F 2/36* (2006.01)
*A61F 2/38* (2006.01)
*A61B 17/17* (2006.01)
*A61F 2/30* (2006.01)
*A61F 2/46* (2006.01)
*A61B 17/68* (2006.01)
*A61B 17/72* (2006.01)
*A61B 17/90* (2006.01)

(52) U.S. Cl.
CPC ............ *A61F 2/389* (2013.01); *A61F 2/3859* (2013.01); *A61F 2/4014* (2013.01); *A61F 2/4081* (2013.01); *A61B 17/1725* (2013.01); *A61B 17/1778* (2016.11); *A61B 17/72* (2013.01); *A61B 17/8875* (2013.01); *A61B 17/90* (2021.08); *A61B 2017/681* (2013.01); *A61F 2002/3069* (2013.01); *A61F 2002/30322* (2013.01); *A61F 2002/30433* (2013.01); *A61F 2002/30593* (2013.01); *A61F 2002/30594* (2013.01); *A61F 2002/30617* (2013.01); *A61F 2002/4687* (2013.01)

(56) References Cited

U.S. PATENT DOCUMENTS

| | | |
|---|---|---|
| 2005/0125067 A1 | 6/2005 | Sweeney |
| 2010/0137925 A1 | 6/2010 | Durand-Allen et al. |
| 2012/0172992 A1 | 7/2012 | Fockens |
| 2016/0128841 A1 | 5/2016 | Dalla Pria et al. |
| 2017/0151059 A1 | 6/2017 | Segina et al. |

PERIPROSTHETIC SHOULDER FRACTURE REPAIR

CROSS REFERENCE TO RELATED APPLICATIONS

This application claims priority to a co-pending U.S. patent application Ser. No. 16/027,605 filed Jul. 5, 2018 by Daniel Nick Segina, James A. Proctor, Jr. and James Arthur Proctor, III for "PERIPROSTHETIC SHOULDER FRACTURE REPAIR which in turn claimed the benefit of U.S. Provisional Patent Application Ser. No. 62/640,378 filed Mar. 8, 2018 by Daniel Nick Segina, James A. Proctor, Jr. and James Arthur Proctor, III for PERIPROSTHETIC SHOULDER FRACTURE REPAIR", and the benefit of a U.S. Provisional Patent Application Ser. No. 62/528,675 filed Jul. 5, 2017 by Daniel Nick Segina, James A. Proctor, Jr. and James A. Proctor, III for SHOULDER EMBODIMENT OF PERIPROSTHETIC FRACTURE REPAIR".

This application is also related to U.S. patent application Ser. No. 15/893,911 filed on Feb. 12, 2018 by Daniel Nick Segina, James A. Proctor, Jr. and James A. Proctor, III for PERIPROSTHETIC FRACTURE MANAGEMENT ENHANCEMENTS, which is a continuation of U.S. patent application Ser. No. 15/372,609 filed Dec. 8, 2016, by Daniel Nick Segina, James A. Proctor, Jr. and James A. Proctor, III for PERIPROSTHETIC FRACTURE MANAGEMENT ENHANCEMENTS, which is a continuation of U.S. patent application Ser. No. 15/068,923 filed on Mar. 14, 2016 by Daniel Nick Segina, James A. Proctor, Jr. and James A. Proctor, III for PERIPROSTHETIC FRACTURE MANAGEMENT ENHANCEMENTS, which is a continuation of U.S. patent application Ser. No. 14/200,678 filed on Mar. 7, 2014 by Daniel Nick Segina, James A. Proctor, Jr. and James A. Proctor, III for PERIPROSTHETIC FRACTURE MANAGEMENT ENHANCEMENTS, which is a continuation of U.S. patent application Ser. No. 13/398,512 filed on Feb. 16, 2012, by Daniel Nick Segina, James A. Proctor, Jr. and James A. Proctor, III for PERIPROSTHETIC FRACTURE MANAGEMENT ENHANCEMENTS, which claims the benefit of U.S. Provisional Application No. 61/443,292, filed on Feb. 16, 2011.

The entire teachings of all of the above patent applications are incorporated herein by reference.

BACKGROUND

1. Field

The present disclosure relates generally to methods and apparatus for allowing for improvements in the repair of periprosthetic fractures. In some embodiments, these improvements involve the inclusion of features within the implanted prosthetic allowing for use of an apparatus for effective and efficient alignment and installation of one or more fracture stabilization components and related components.

2. Related Art

The current state of fixation of periprosthetic fracture revolves around devices that are designed to avoid originally placed femoral, tibial, humeral, or other components. With a multitude of different fracture patterns that could clinically exist, current solutions for the variability of fracture patterns revolve around the use of either an external bone plate or an internal medullary rod/nail.

Existing approaches for conventional periprosthetic fracture management often result in sub-optimal prognosis as compared with fracture management in the absence of a conventional prosthesis. Additional impacts to the patient recovery time result from significantly more invasive procedures being required for the application of such conventional fracture management devices.

SUMMARY OF PREFERRED EMBODIMENTS

Embodiments of the current invention provide for pre-engineered fracture fixation contingent solutions into femoral, tibial, shoulder, humeral or other components, resulting in a distinct clinical advantage in the planning and execution for periprosthetic fracture fixation. Additional embodiments include a pre-engineered solution to intimately associate with the previously placed total hip arthroplasty or total knee arthroplasty and further in some embodiments utilize approaches for allowing targeting of required fasteners, screws and the like, using a mechanically associated relationship to the existing prosthetic, or other components.

Specific embodiments are related to the design of prosthetics for artificial hip and knee replacement, the repair of Periprosthetic fractures, and associated methods and apparatus for use in the application of fracture stabilization components. Additional embodiments provide for a variety of fracture fixation options should a fracture occur after total hip arthroplasty or total knee arthroplasty.

Other embodiments are more specific to standard or reverse total shoulder replacement, the repair of fractures related to the same, and associated methods and apparatus for use in the application of fracture stabilization components. Additional embodiments provide for a variety of fracture fixation options should a fracture occur after such shoulder replacement.

To support the application of such fixation options in specific embodiments provide for apparatus and methods to include the use of alignment devices and other components to allow methods for ease of repair of Periprosthetic fractures utilizing the pre-engineered solutions. Such targeting devices are required in specific circumstances as the prosthetics may prevent x-ray imaging and consequently free hand alignment. Specific embodiments of the aforementioned alignment device/outrigger may be composed of carbon fiber or other materials transparent to imaging technology utilizing radio lucent materials.

In one embodiment, a method for repairing a periprosthetic fracture comprises mounting an aligning device in mechanical registration with an in situ prosthetic component and locking a fracture stabilization component, and aiming arm, the aligning device and the in situ prosthetic component in mechanical alignment, utilizing the aiming arm to provide alignment of one or more mechanical cannula with one or more prosthetic component interfaces and securing one or more bone fracture segments associated with the periprosthetic fracture with said fracture stabilization component using screws, wherein the fracture stabilization component and the prosthetic component are further mechanically secured.

In another embodiment, a periprosthetic fracture device comprises mounting an aligning device in mechanical registration with an in situ prosthetic component and locking a fracture stabilization component, and aiming arm, the aligning device and the in situ prosthetic component in mechanical alignment, utilizing the aiming arm to provide alignment of one or more mechanical cannula with one or more prosthetic component interfaces and securing one or more bone fracture segments associated with the periprosthetic fracture with said fracture stabilization component using screws, wherein the fracture stabilization component and the prosthetic component are further mechanically secured.

In another embodiment, the prosthetic component further comprises a threaded coupling point for receiving the aligning device.

In another embodiment, the prosthetic component further comprises a guide wire.

In another embodiment, the aligning device and the aiming arm are a single component.

In another embodiment, the prosthetic component is a modified femoral component, and wherein said femoral component interfaces with a periprosthetic distal femoral polyaxial locking plate.

In another embodiment, the prosthetic component is a modified tibial tray component.

In still other arrangements, the component interface may be notched or keyed for proper rotational alignment.

In another embodiment, the mechanical registration is a notched mechanical interface between a femoral nail and the prosthetic component.

In another embodiment, the aligning device and the aiming arm are mechanically assembled components.

In another embodiment, the fracture stabilization component comprises one of the following: a femoral nail, tibial nail, femoral plate, or tibial nail.

Still other embodiments are specific to a standard or modified total shoulder arthroplasty. Accommodating periprosthetic fractures around the shoulder presents a different challenge than the knee or other joints. The size of the medullary canal in conjunction with the distal humeral anatomy as well as proximal fill of the arthroplasty component limit fracture fixation options in the event of a periprosthetic fracture.

In one embodiment for a shoulder implementation, a medullary fixation device includes a registration component that aligns with a humeral component sheath. The medullary fixation device may accommodate insertion of fracture stabilization devices in the future. Locking hardware allows for length and rotational control.

The humeral sheath may include an outer portion having an optional interface to a vacated inner core, permitting a fixation device to extend beyond a distal extent of the humeral bone fracture.

In some embodiments, the sheath may be integrated with the prosthesis, or a separate component that is inserted into the prosthesis and secured via a threaded channel.

As with other embodiments, an aiming arm can assist with rotational control as well as distal alignment for the targeting and insertion of interlocking devices.

In embodiments for reverse total shoulder arthroplasty, an extra-medullary fixation device may be used. The extra-medullary device includes an outrigger/aiming arm to interface with an intact humeral stem component. The extra-medullary fixation device may include a plate with optional aiming canula and interlocking devices.

In some embodiments, the interlocking devices may be screws that pass through the extra-medullary plate and the underlying bone, to the humeral stem component including the outer sheath and inner core.

Optionally, an aiming arm containing an aiming cannula may provide for registration and alignment allowing for the passage of an interlocking device, such as a a screw, through the outer bone cortex, through a distal aspect of a medullary fixation device, to the innermost cortex of the distal humeral bone.

In an embodiment, a proximal locking cap may be placed to provide coverage over the extra-medullary fixation device and the underlying humeral stem component screws. The proximal locking cap may also allow for alignment and rotational registration between the intact humeral stem and the medullary fixation device.

An alternative standard total shoulder embodiment may contain a humeral head articular component as well as solid shaft component or humeral stem component that includes an interface for coupling an extramedullary aiming arm.

A locking end cap containing a recess for a tool such as a hex screwdriver may be used, such an end cap may have a threaded tip allowing for interfacing with a solid humeral core component. Both the recess and the outer diameter of the locking end cap may be circular, thus allowing for unencumbered rotation.

In another embodiment, the interface between the humeral component solid core and the surrounding humeral component may include registration slots or notches brought into alignment with the use of the registration washers or other hardware, and may have features that accommodate the use of tools for securing the hardware. This arrangement provides further solid axial and rotational control.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating the configuration and use of the different embodiments.

DETAILED DESCRIPTION OF PREFERRED EMBODIMENTS

A description of example embodiments follows.

Figure 1:
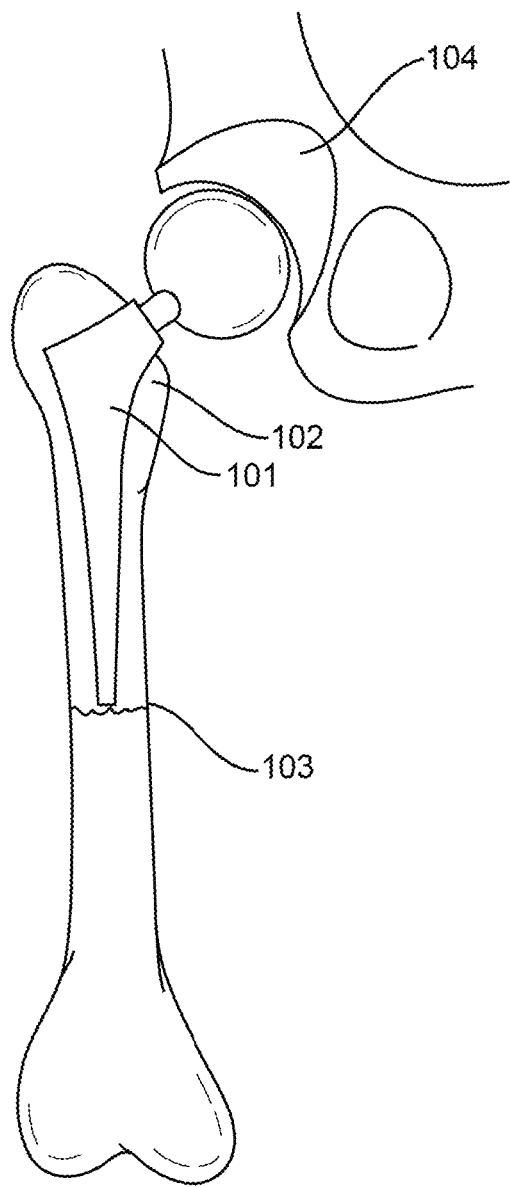
FIG. 1 is an illustration of a first defined fracture below the hip prosthesis.

FIG. 1: Problem #1—Fracture Below Hip Prosthesis

FIG. 1 shows an existing problem in the industry of a fracture below a hip prosthesis. The prosthesis 101, articulates with the hip joint 104, as is known within the industry. Furthermore, the Hip Prosthesis 101 is implanted within the proximal femur 102. Periprosthetic Femur fracture 103 occurs post implantation of the prosthesis 101, into the proximal femur. The current challenge within orthopedic surgery is the fixation of a fracture after implantation of Hip Prosthesis 101. The metallic implant obscures the capacity to provide for fixation through the bone by occupying the inner space of the medullary femoral canal. Clinical solutions attempt to avoid the femoral prosthesis 101 by providing for screw trajectories away from the implant or options for circumferential wire fixation around the implant. While the current fracture pattern 103 is described within, this does not and is not intended to limit the scope of the application of the embodiments of this invention.

Figure 2:
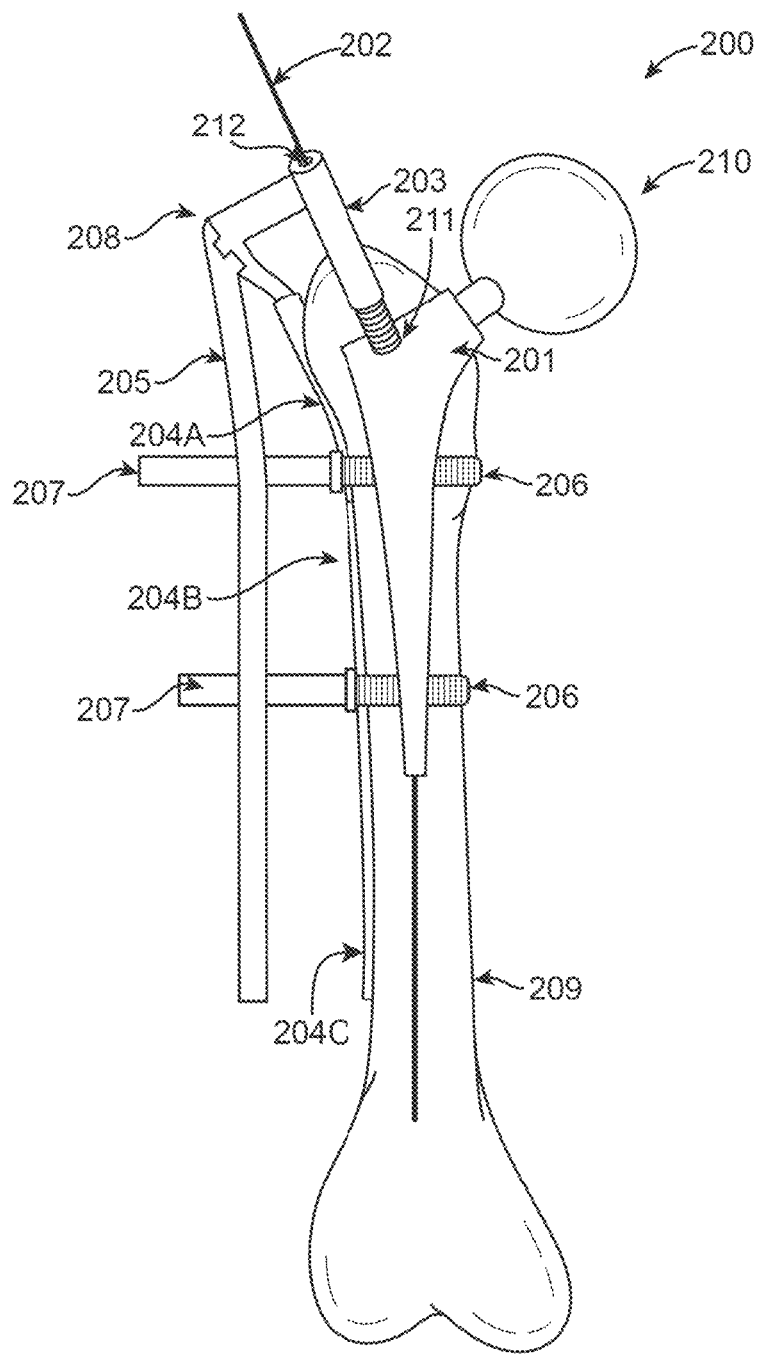
FIG. 2 is an illustration of an embodiment including: Modified Femoral Component to Accommodate Cannulated Outrigger, Custom Modular Plate and Targeting Device.

FIG. 2: Embodiment of Solution #1—Modified Femoral Component to Accommodate Cannulated Outrigger, Custom Modular Plate and Targeting Device.

This section discusses one embodiment to address the problem of FIG. 1, depicted in fracture pattern 103.

Modified Femoral Component 201 is implanted into the proximal femur.

Femoral component 201 with hollow core 212 to accommodate guide a Targeting Guide Wire 202 is depicted to provide for a reference point for an aligning device, such as Cannulated Outrigger 203. This allows for alignment and an intimate association between Femoral Component 201 and an aligning device, such as Cannulated Outrigger 203, resulting in a unique interface reference point 211. Interface Reference point 211 may utilize keyed interfaces between an aligning device, such as Cannulated Outrigger 203 and between Femoral Component 201 so as to allow for a further angular or rotational reference. As a result, spatial orientation is now predetermined and referenced off of the previously implanted Femoral Component 201. With a fracture stabilization component, such as the Cannulated Outrigger 203 mated to Modified Femoral Component 201, an aiming arm, such as a Distal Targeting Device 205 can then be assembled to provide for appropriate and accurate targeting of Fixed Angled Locking Screws 206; targeting through Screw Alignment Cannulae 207 thus providing a mechanism for security fixation of a fracture stabilization component, such as the Custom Modular Plate 204A, 204B, and 204C. Clinical solutions for Coupling Point 208 represent a mating mechanism between the Cannulated Outrigger 203 and an aiming arm, such as the Distal Targeting Device 205. This intimate fit, once again, assures appropriate targeting of the Fixed Angled Locking Screws 206 through the Modified Femoral Component 201 which revolves around fixation. The Modified Femoral Component 201 is implanted into the Native Femur depicted as 209. The interface between Modified Femoral Component 201 and Cannulated Outrigger 203 is described via a threaded Cannulated Outrigger Interface 211. The cannulation of this interface happens over a hollow core 212 which is inserted through Cannulated Outrigger 203 and the Modified Femoral Component 201.

The capacity for the Modified Femoral Outrigger 203 to be mated to the Femoral Component 201 provides for accurate reference point to thus target the screws depicted in 206. This overcomes the challenge of alignment, which is not referenced, and presents a difficult clinical challenge for targeting the appropriate screw 206 and implant 201 interfaces. The clinical benefits extend to the decreased surgical time due to known reference point between Modified Femoral Component 201 and 203; in addition to decreased surgical trauma and surgical dissection in attempts to find the appropriate alignment between Modified Femoral Component 201, Plate 204A, B, and C, and Screw 206. The capacity to limit surgical time as well as surgical exposure necessarily translates into decreased cost as well as decreased patient morbidity. Additionally, improved mechanical fixation would be enhanced due to accurate targeting and interface between Modified Femoral Component 201 and a fracture stabilization component, such as Modular Plate 204A, B, and C as well as Screws 206. Femoral Component 201 would be inserted at the time the patient would be undergoing a total hip arthroplasty. The utility of the interface 211 would come into play after a periprosthetic fracture was to occur. The insertion of Guide Wire 202 into Modified Femoral Component 201 to facilitate the interface of Cannulated Outrigger 203 would be temporary. This interface can then be uncoupled after fixation of the fracture has occurred through the use of a fracture stabilization component, such as the Modular Plate 204A, B, and C and screw fixation with Screw 206. The pre-engineered geometry in Modified Femoral Component 201 would be done at the time of manufacture of said component. Additionally, the Interface 211 as well as the screw holes for Screw 206 would be incorporated into Component 201 prior to implantation, thus ready to be utilized at a future date should periprosthetic fracture of Native Femur 209 occur after total hip arthroplasty. Necessitates it is inserted into the Modified Femoral Component 201 and around the prosthesis either via screws in a trajectory that does not interfere with the Prosthesis 101 or wires that wrap around the bone properly, providing for a method of fixation that once again does not interfere with Prosthesis 101. It should be noted that this deals with only one specific fracture pattern of the proximal femur below a Hip Prosthesis 101. Other potential fracture patterns do exist around other prosthetic implants which will be addressed in further figures in this document.

Figure 3:
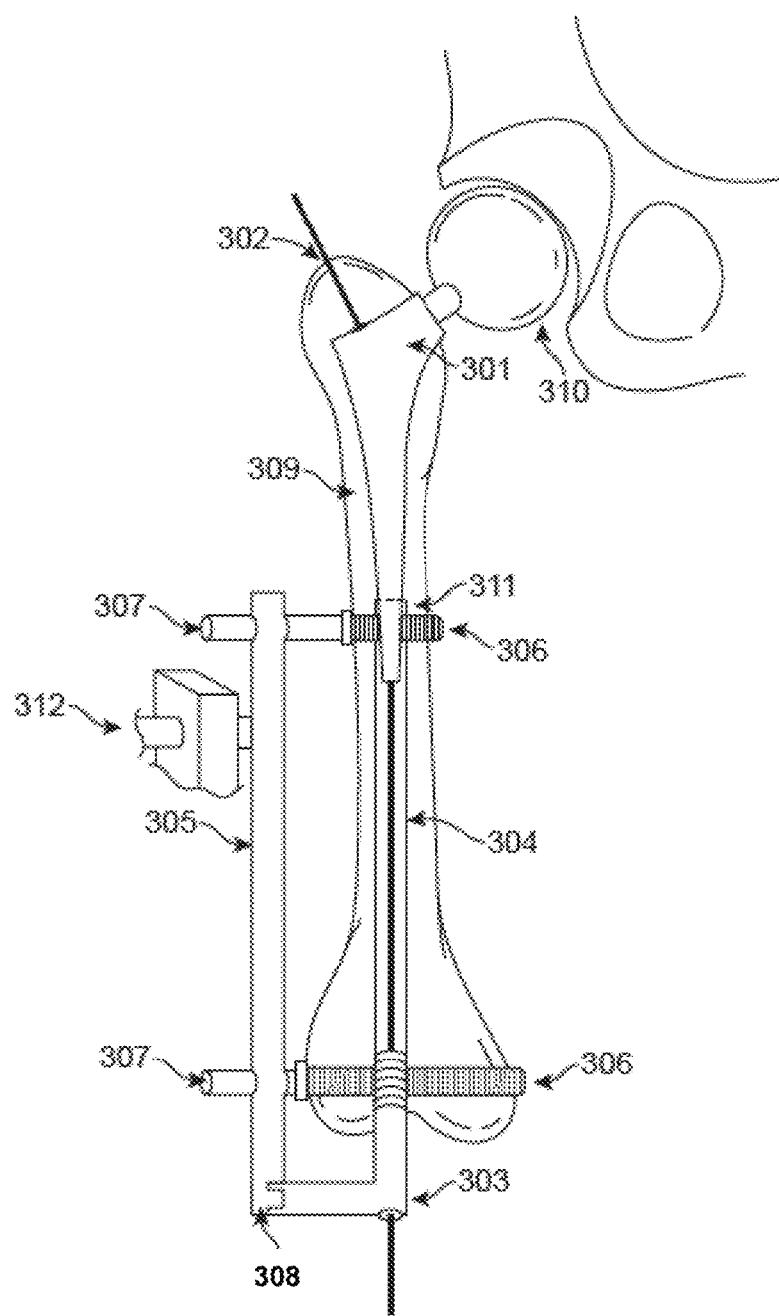
FIG. 3 is an illustration of an embodiment including: Alternative Modified Femoral Component to Accommodate Cannulated Outrigger, Custom Retrograde Nail and Targeting Device.

FIG. 3: Solution #2—Alternative Modified Femoral Component to Accommodate Cannulated Outrigger, Custom Retrograde Nail and Targeting Device FIG. 3 represents an alternative embodiment of the modified femoral component 301 and associated components. This embodiment of the modified femoral component accommodates a custom retrograde Femoral Nail 304 in the treatment of a periprosthetic distal femur fracture. The modified Femoral Component 301 would be inserted at the time of total hip arthroplasty; this component is utilized as a component of fixation of said fracture of the Native Femur 309 after total hip arthroplasty. The Guide Wire 302 is inserted through the Modified Femoral Component 301 which contains an inner cannulation component. The guide wire is advanced to the end of the Native Femur 309 and goes past the fracture site. This guide wire is then be utilized to direct the Custom Retrograde Femoral Nail 304 so that it is placed over the tip of the Modified Femoral Component 301 to provide for an engagement and subsequently secure fracture fixation. The interface between the Modified Femoral Component 301 and the Custom Retrograde Femoral Nail 304 will be further depicted in FIG. 4 which is labeled in the current diagram as 311. Some embodiments will provide for a keyed interface 311 between the Modified Femoral Component 301 and the Custom Retrograde Nail 304. The insertion of the Guide Wire 302 to accommodate and guide the Retrograde Femoral Nail 304 takes place at the time of surgical repair of the fracture. Once the guide wire has been passed to the end of the Native Femur 309 an opening at the distal femur would occur to provide for an entry portal of the Retrograde Femoral Nail 304. Attached to the Retrograde Femoral Nail 304 would be an aligning device, such as the custom Cannulated Outrigger 303. This outrigger is cannulated to accommodate the Guide Wire 302 and the Guide Nail 304 to the appropriate position at the tip of the Customized Modified Femoral Component 301. Attached to 303 will be an aiming arm, such as the Proximal Targeting Device 305. The adjoinment of 305 to 303 would occur at Coupling Point 308. Once an aiming arm, such as the proximal targeting device, is in place it would provide for appropriate and predetermined targeting for the Fixed-Angled Interlocking Screws 306 both at the proximal and distal aspect of the fixation. The screws would align with the fixation device, customized Retrograde Femoral Nail 304, with the use of an aiming arm, such as the proximal targeting device, and the Screw Alignment Cannula 307. A cutaway diagram reveals a three-dimensional profile of an aiming arm, such as Proximal Targeting Device 305, which is labeled 312 in this figure. The benefits of this embodiment provide for a biologically favorable method of fixation that is amenable to minimal soft tissue stripping thus preserving biology around the fracture and helping promote rapid healing. Additionally, surgical time would be significantly shortened. Biomechanical favorability is also achieved with the overlap interface that is obtained between the Customized Modified Femoral Component 301 and the Custom Retrograde Femoral Nail 304. Once again this interface, labeled 311, will be further depicted in the next drawing.

In addition, Modified Femoral Component distal tip 311, may include (in specific embodiments) a specific alignment key feature which allows for alignment of pre-drilled holes which may be present in the Custom Retrograde Femoral Nail 304, and the Modified Femoral Component 301, such that a keying feature angularly aligns with a keying feature present in the Retrograde Femoral Nail 304. One such keying feature may be a notched interface, allowing for proper rotational alignment.

Figure 4:
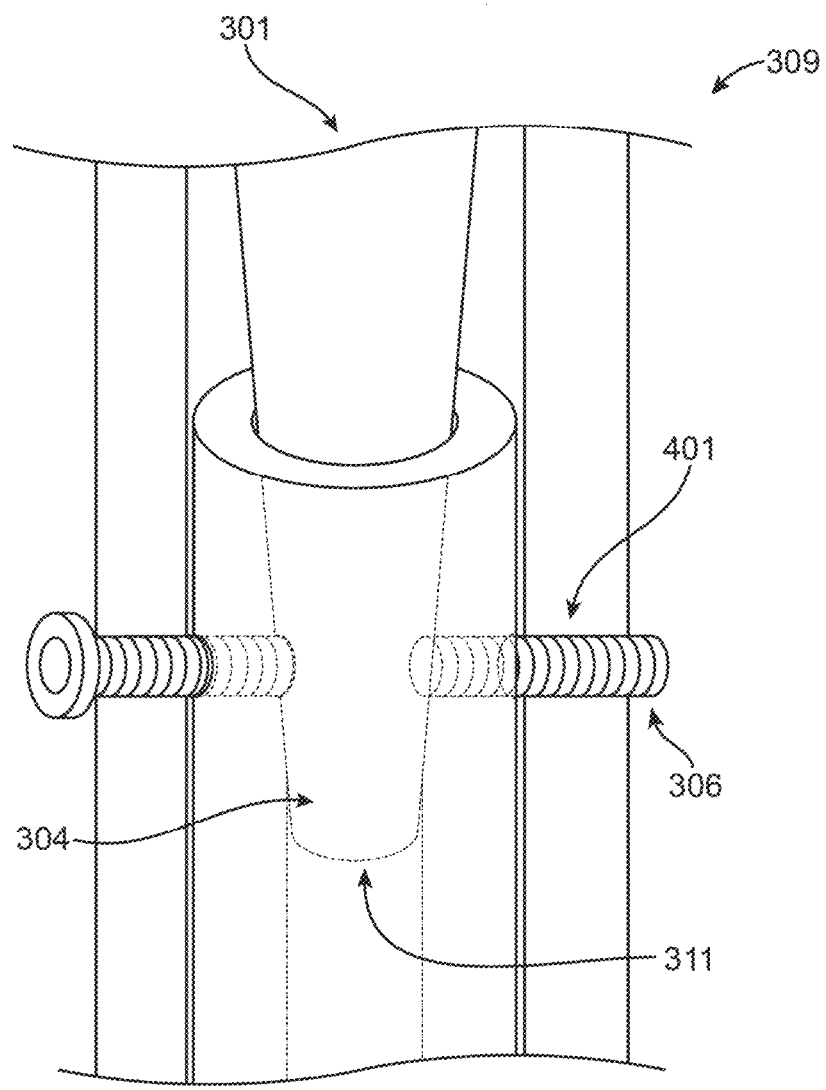
FIG. 4 is an illustration of an embodiment including: Magnified detail of Modified Femoral Component Tip to Accommodate Retrograde Nail.

FIG. 4: Magnified detail of Modified Femoral Component Tip to Accommodate Retrograde Nail In FIG. 4 the depiction represents the interface on a magnified scale between the Modified Femoral Component 301 and the Custom Retrograde Femoral Nail 304. The interface is further specified as 311. In this depiction, a tapering and smaller diameter at the tip of 301 is designed to provide for a unique and overlapping interface between the Modified Femoral Component 301 and the Retrograde Femoral Nail 304. This overlap helps achieve mechanical stability by preventing a stress riser that would occur if no overlap were to exist. Additionally, a predetermined trajectory would be placed and aligned to accommodate the Angular Stable Interlocking Screw 306. This would interface through the cortical bone depicted as 401 as well as the Custom Retrograde Femoral Nail 304 and the Modified Femoral Component 301 and subsequent Modified Femoral Component Distal Tip 311. The ability to target this screw and align it appropriately would be facilitated through the attachment of an aligning device, such as the Cannulated Outrigger 303 depicted in FIG. 3 along with an aiming arm, such as the Proximal Targeting Device 305 and subsequent Alignment Cannula 307.

Figure 5:
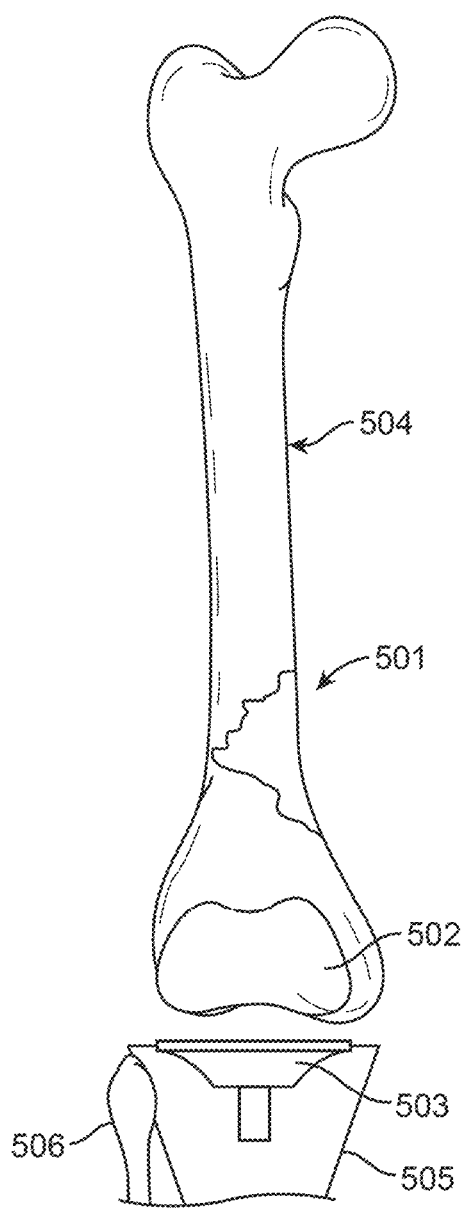
FIG. 5 is an illustration of a periprosthetic distal femur fracture.

FIG. 5: Problem #2—Periprosthetic Distal Femur Fracture Above a Prosthetic Total Knee Arthroplasty.

Depicted in FIG. 5 is the clinical scenario where a fracture would occur above a previously inserted total knee arthroplasty. The fracture would occur in the Native Bone 504 and be depicted by the Fracture Pattern 501. Please note that this is one of potentially many different fracture patterns that may exist and this is only one embodiment of this said fracture. The Femoral Component 502 would be placed onto the Native Femur 504 at the time of total knee arthroplasty. Similarly, the Tibial Component 305 would be placed into the Native Tibia 505 at the time of total knee arthroplasty to articulate the Femoral Component 502. Additionally depicted is the Native Fibula 506. The clinical problem that will be subsequently discussed will be to address said fracture 501 above a total knee arthroplasty otherwise known as a periprosthetic distal femur fracture.

Figure 6:
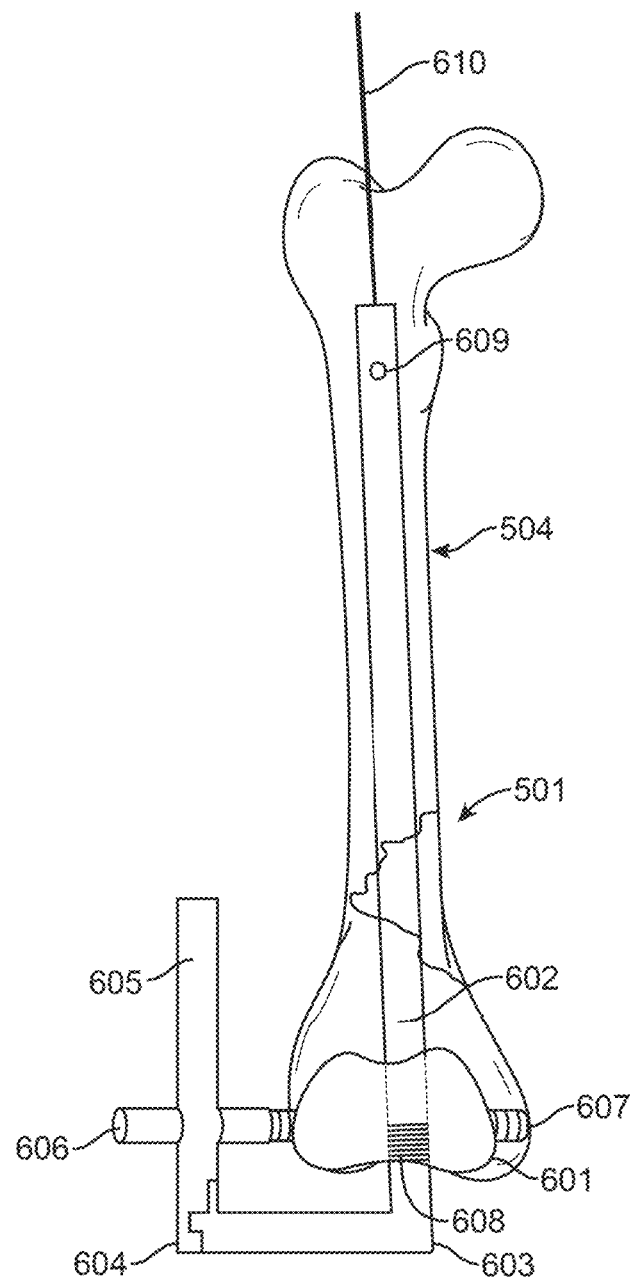
FIG. 6 is an illustration of an embodiment including: Angular Stable Retrograde Periprosthetic Distal Femoral Nail.

FIG. 6: Embodiment of Solution #3—Angular Stable Retrograde Periprosthetic Distal Femoral Nail In an embodiment of one of the current inventions, the alignment devices including the Cannulated Outrigger 603, Proximal Targeting Device 605, Angular Stable Screw Alignment Cannula 606, and Couple Point 604 can be constructed out of a radiolucent material to provide for an avenue of X-ray visualization to help assure appropriate alignment as well as placement. In this embodiment, alignment device required as the prosthetics prevent x-ray imaging and free hand alignment. This is a key advantage and solution to an existing problem. Also note that the alignment device/outrigger may be composed on carbon fiber or other materials transparent to imaging technology using radio lucent materials in some embodiments.

Figure 7:
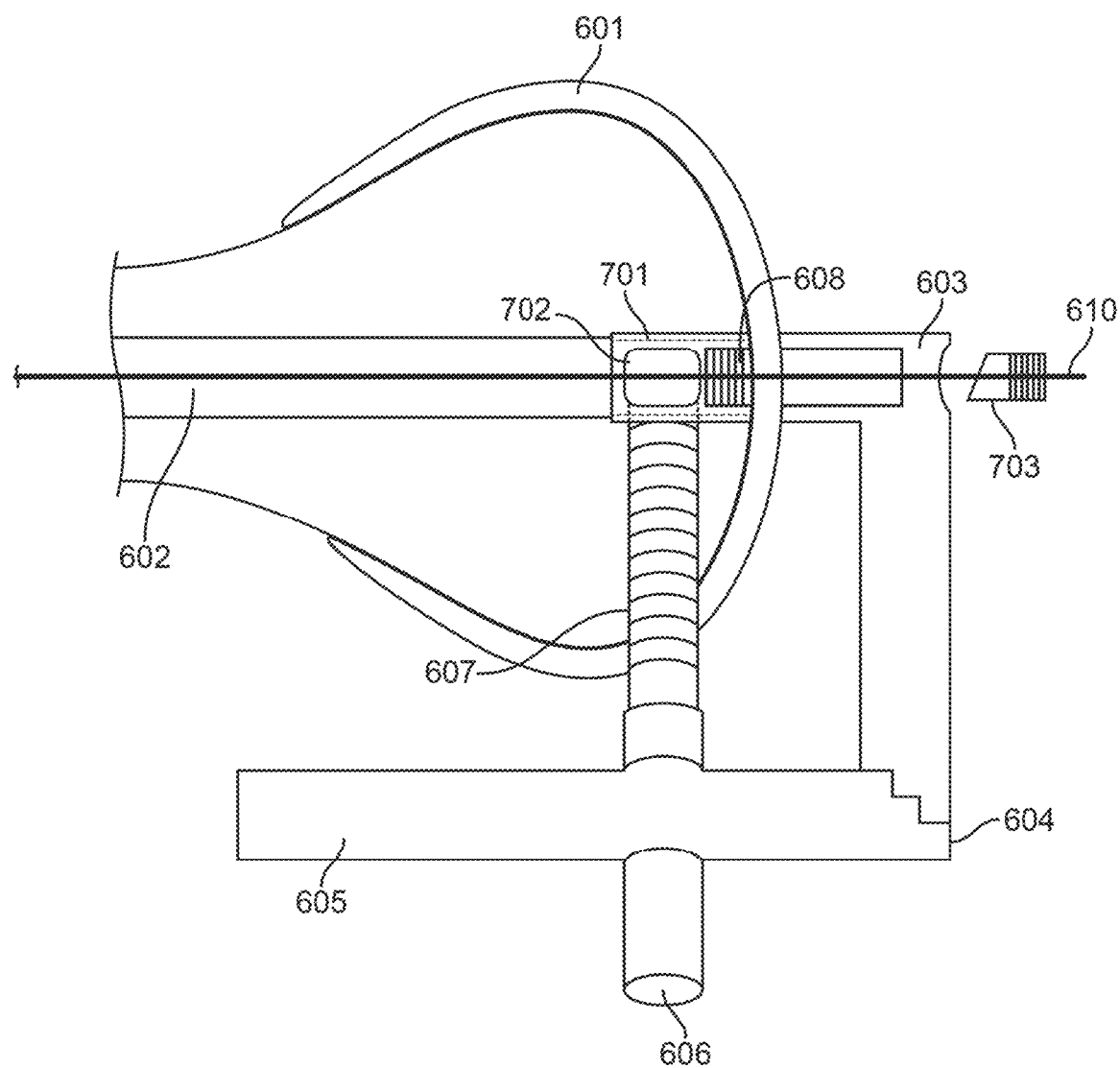
FIG. 7 is an illustration of an embodiment including: Detailed Lateral Projection of Modified Femoral Component (601).

FIG. 7: Detailed Lateral Projection of an Embodiment of a Modified Femoral Component (601)

Depicted in this drawing is a lateral projection of an embodiment of the Modified Femoral Component 601 with the Custom Angular Stable Retrograde Femoral Nail 602 being inserted as would happen in a clinical scenario during fracture repair. The insertion is to the point where the interface is occurring between the Modified Femoral Component 601 and the Custom Retrograde Angular Stable Femoral Nail 602. The alignment as well as insertion would be facilitated over Guide Wire 610 and through the attached Custom Outrigger 603, aiming arm, such as Proximal Targeting Device 605, Alignment Cannula 606, and Coupling Point 604. Depicted out of plane is the Angular Stable Interlocking Screw 607 which would traverse the region labeled 702 and interact with the modification of Modified Femoral Component 601, depicted as 701. The interface and alignment is secured between the Custom Retrograde Femoral Nail 602 and an aligning device, such as the Cannulated Outrigger 603 by a Threaded Interface 608. The design of Subcomponent 601, that is labeled 701, would be made in a way to accept the Retrograde Femoral Nail 602 as well as provide for the traversing of the Angular Stable Interlocking Screw 607. The geometry is designed, as such, to control the coronal and sagittal plane angulatory forces to help maintain alignment. The final capacity to be able to maintain this alignment would be facilitated by the angular stable set assembly end cap with three rotating angular interfaces. Further detail of this object will be described in FIG. 8. Further details around the Area 701, which is specifically described as contingent prosthetic distal femoral nail interface, will be provided. The design of 701 would be manufactured into the Component 601 at the time of initial manufacturing. This modification, 701, would exist at the time of total knee arthroplasty and be present as a contingent source of fixation with angular stabilization should a fracture of the distal femur arise. The geometry of 701, once again, would be to accept the Angular Stable Interlocking Screw 607 as well as the angular stable set assembly end cap with Free Rotating Angular Interface 703. The addition of these two devices through the portal labeled 702 would then be able to obtain and maintain sagittal as well as coronal plane stability. This embodiment encompasses the distinctive benefits of both 703 by itself, and 701 by itself, as well as combined. Further use of 701 as a contingent structure, and separately as a device to accept the nail in operation are further contemplated.

Figure 8:
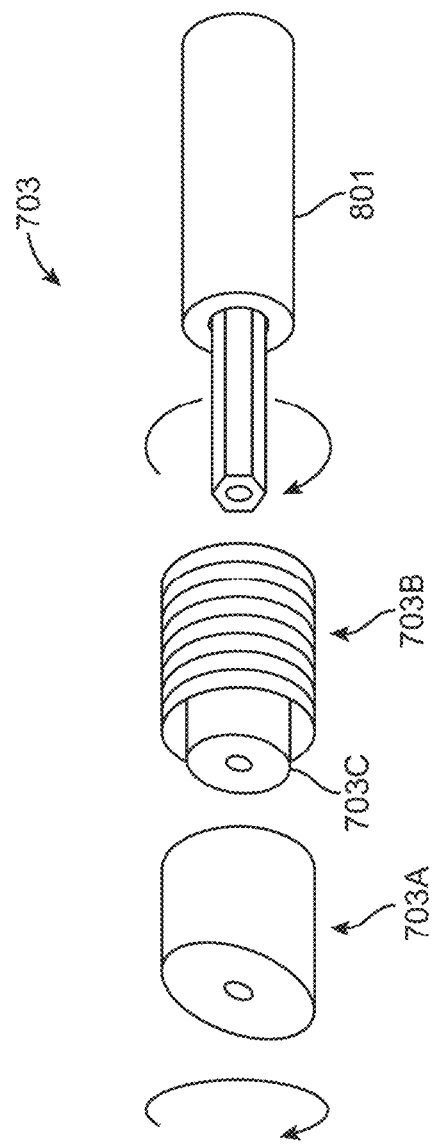
FIG. 8 is an illustration of an embodiment including: Detail of (703) Angular Stable Set Assembly with Free Rotating Angular Interface.

FIG. 8: Detail of an Embodiment of (703) Angular Stable Set Assembly with Free Rotating Angular Interface Depicted in FIG. 8 is a breakdown of an embodiment of the components of the angular stable set assembly end cap with free rotating angular interface. This end cap would be inserted through the Custom Outrigger 603 over the Guide Wire 610. It would then interface through the subcomponent of the Modified Femoral Component 601, labeled as 701. This interface would then provide for a frictional fit to secure the Angular Stable Interlocking Screw 607. Depicted in FIG. 8 is 703A which is the angular portion of the angular state assembly end cap. This is depicted as having a smooth surface to provide for a free-glide insertion without interfacing with underlying threads. Allowing for the insertion would be a Threaded Component 703B. This would interface the threaded component of the Custom Retrograde Femoral Nail 602 at the region labeled 608 in FIG. 7. The threaded capability of this component provides for a threaded and locked frictional fit to secure the interface between Subcomponent 703 of the angular stable set assembly with free rotating angular interface and the Angular Stable Interlocking Screw 607. Free rotation of this device would be allowed through the interface containing a smaller diameter to engage, labeled 703C. The entire Assembly 703A, 703B, and 703C, once placed over the Guide Wire 610, would be screwed into position using the Cannulated Screwdriver 801.

Figure 9:
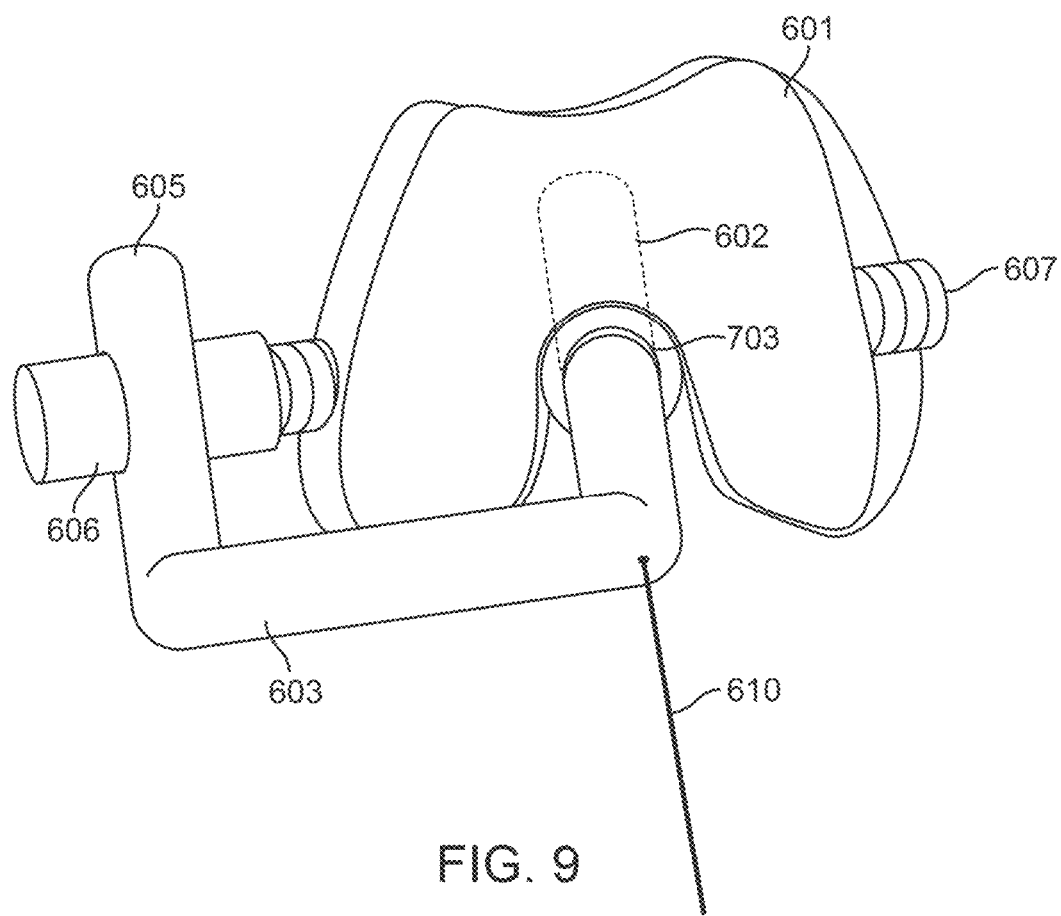
FIG. 9 is an illustration of an embodiment including: Distal Axial Projection of FIG. 6: Angular Stable Retrograde Periprosthetic Distal Femoral Nail.

FIG. 9—Distal Axial Projection of FIG. 6 and an Embodiment of an Angular Stable Retrograde Periprosthetic Distal Femoral Nail Depicted in FIG. 9 is an embodiment of the current invention including an axial projection viewing the innerconnular region of the Modified Femoral Component 601. Once the Retrograde Femoral Nail 602 is inserted through the inner-connular notch over Guide Wire 601, and facilitated by an aligning device, such as the Cannulated Outrigger 603, an Angular Stable Interlocking Screw 607 would then be inserted. This insertion would be introduced with the Alignment Cannula 606 and placed through an aiming arm, such as the Proximal Targeting Device 605. The interface would occur at the modified subcomponent of Modified Femoral Component 601, labeled 703. The projection of 703 in this diagram is a combination of 701 and 702 from FIG. 7. The purpose of this depiction is to demonstrate that no alteration of the surface of the Modified Femoral Component 601 would occur at the time that the fracture fixation would take place, using the insertion of Modified Retrograde Femoral Nail 602 and the placement of Angular Stable Interlocking Screw 607.

Figure 10:
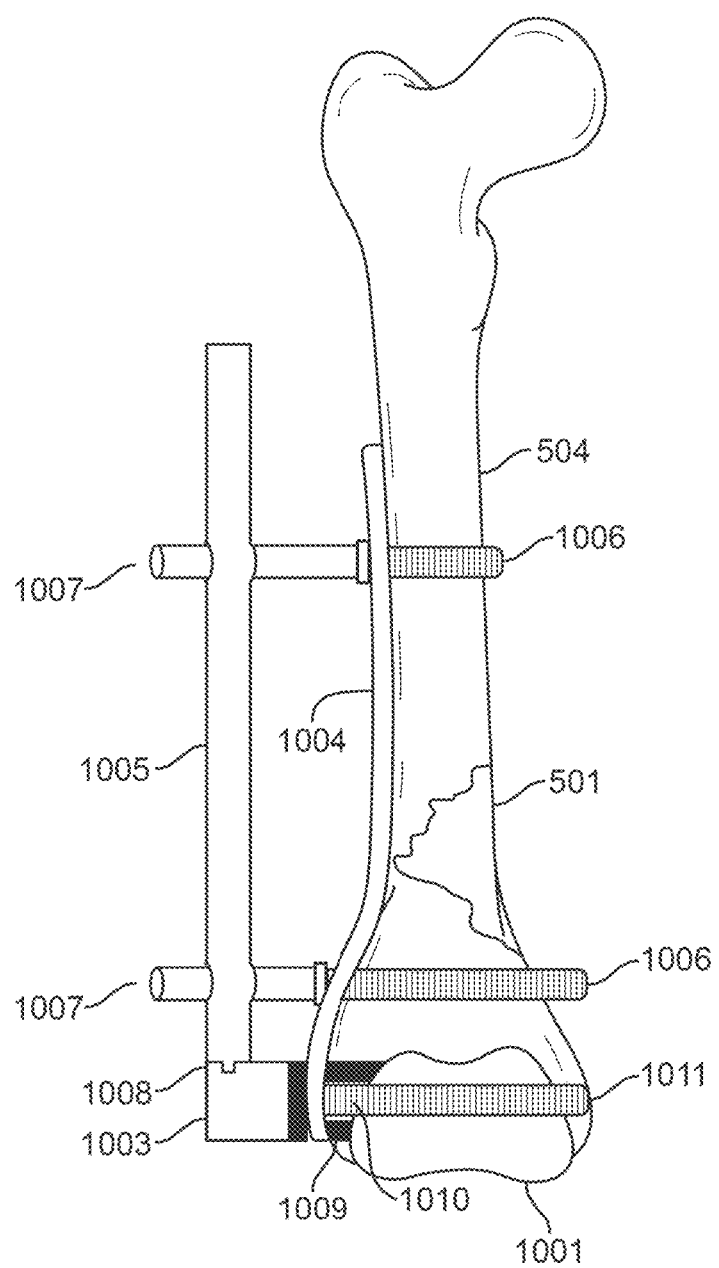
FIG. 10 is an illustration of an embodiment including: Distal Femoral Periprosthetic Plate Fixation with contingent prosthetic interface.

FIG. 10: Solution #4—Distal Femoral Periprosthetic Plate Fixation with Contingent Prosthetic Interface Depicted in this diagram is an alternative embodiment of a method of fixation to deal with a periprosthetic distal femoral fracture. This fracture would be of Native Bone 504 and is depicted as Fracture Pattern 501. The Modified Femoral Component 1001 would be placed at the time of total knee arthroplasty. Modifications would be in place at the time of manufacture of Modified Femoral Component 1001 and be available for a contingent fracture fixation should Fracture 501 occur after total knee arthroplasty takes place. The Modified Femoral Component 1001 is further described as a modified femoral component that interfaces with custom angle stable periprosthetic distal femoral, polyaxial locking plate. In FIG. 10, the Distal Plate Outrigger 1003 is shown to connect to the Custom Angular Stable Periprosthetic Distal Femoral Polyaxial Locking Plate 1004 through the 1003/1001 custom interface-prosthetic contingent mounting interface. Through Couple Point 1008 Proximal Targeting Device 1005 is depicted providing for cannula placement for Screw Alignment Cannula 1007. Through 1007 there would be placed some Fixed Angled Locking Screws 1006 which would interface and subsequently thread into Plate 1004. Distally, once 1009 prosthetic contingent mounting interface is installed to 1004 as well as 1001, the predetermined alignment would be allowed for the placement of Central Distal Angular Stable Interlocking Screw 1011 through the Central Distal Angular Stable Screw Portal 1010.

This alternative embodiment of fixation for Distal Femoral Fracture 501 utilizes a plate-and-screw construct to achieve axial, sagittal, as well as coronal plane alignment maintenance. The capacity to interface with Modified Femoral Component 101 allows for no reliance upon the integrity of the Distal Femoral Bone 504, but rather the ability to directly interface and adjoin to Modified Femoral Component 101 so as to maintain above-said alignments in all three planes. Fracture fixation and alignment is also further maintained with the insertion of additional Locking Screws 1006 above and below the Periprosthetic Fracture 501. The clinical advantage of this device once again provides for minimally invasive exposure of the distal femur and soft tissue preservation for enhanced biologic preservation around Fracture Site 501. Aiming arm, such as the Proximal Targeting Device 1055 would reside outside the skin of the soft tissue envelope of the Femur 504 and guide 1007, screw alignment cannula, through the skin to align appropriately with the Custom Angular Stable Periprosthetic Distal Femoral Polyaxial Locking Plate 1004. Screws would then be inserted through the Plate 1004 and Underlying Bone 504 and lock into position.

Figure 11:
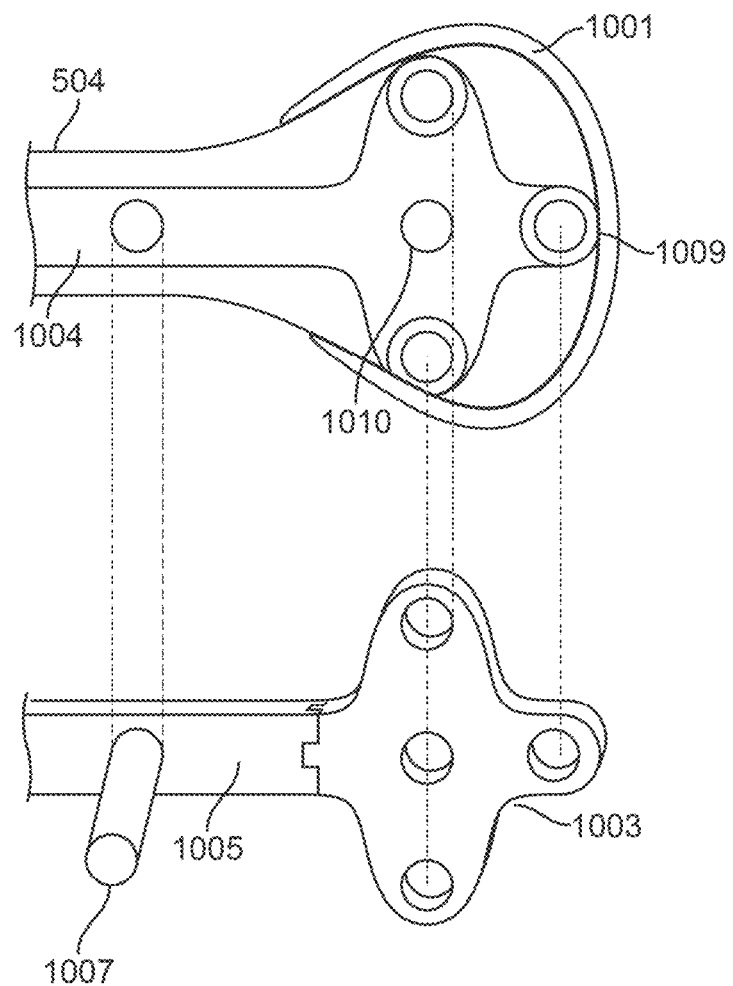
FIG. 11 is an illustration of an embodiment including: Lateral Projection of Distal Femoral Periprosthetic Plate Fixation with contingent prosthetic interface.

FIG. 11: Lateral Projection of en Embodiment of a Distal Femoral Periprosthetic Plate Fixation with Contingent Prosthetic Interface This figure details an embodiment of the three-phase interface between Modified Femoral Component 1001, the custom angular stable periprosthetic distal femoral plate and the Distal Femoral Outrigger 1003. Depicted in 1009 is the interface that allows for the adjoining of 1003 to Modified Femoral Component 1001 as well as the Interposed Plate 1004. The ability to interface all three components provides for the ability to specifically target an angular stable interlocking screw depicted as 1011 in FIG. 10. With the adjoining of these components a fixed-angled construct would exist between the Modified Femoral Component 1001 and the Custom Angular Stable Plate 1004; thus being able to achieve the maintenance of axial, sagittal, as well as coronal plane alignment and avoid the reliance upon underlying native bone quality. Additionally depicted is a Central Pole 1010 that would accommodate a large central angular stable interlocking screw for additional fixation. This screw may be placed in a polyaxial locking capacity. Of note, is the modifications of the Distal Femoral Component 1001 to accommodate the adjoining interface to Custom Angular Stable Locking Plate 1004 and the modifications to Modified Femoral Component 601 to accommodate the Custom Retrograde Femoral Nail 602 can be made within the same implant. With both options available for either plate or nail fixation, a variety of different fixation strategies can be accommodated by the same Modified Femoral Component. Once again, these modifications would take place at the time of manufacture of the Modified Femoral Component 601/1001 and not interfere with the articulation of the planned total knee arthroplasty. The contingencies would remain in place and provide for fixation options should a distal femoral fracture depicted as 501, occur.

1009 allows for the joining of the 1003 outrigger to 1004 plate, and additionally provides for the joining of 1001 femoral component to 1004 plate.

In one embodiment, a screw is used to mount the outrigger, through the plate's holes top the prosthetic. 1009 allows for the joining of the 1003 outrigger to 1004 plate, and additionally provides for the joining of 1001 femoral component to 1004 plate. In one embodiment screws are used to mount the outrigger, through the plate's holes on top of the prosthetic. In this embodiment, several novelties in the prosthetic include contingent accommodations for femoral fracture management procedures, and further the specifics of those accommodations and their use at the time of the repair, and the details of the attached devices and methods for using the features provided.

Figure 12:
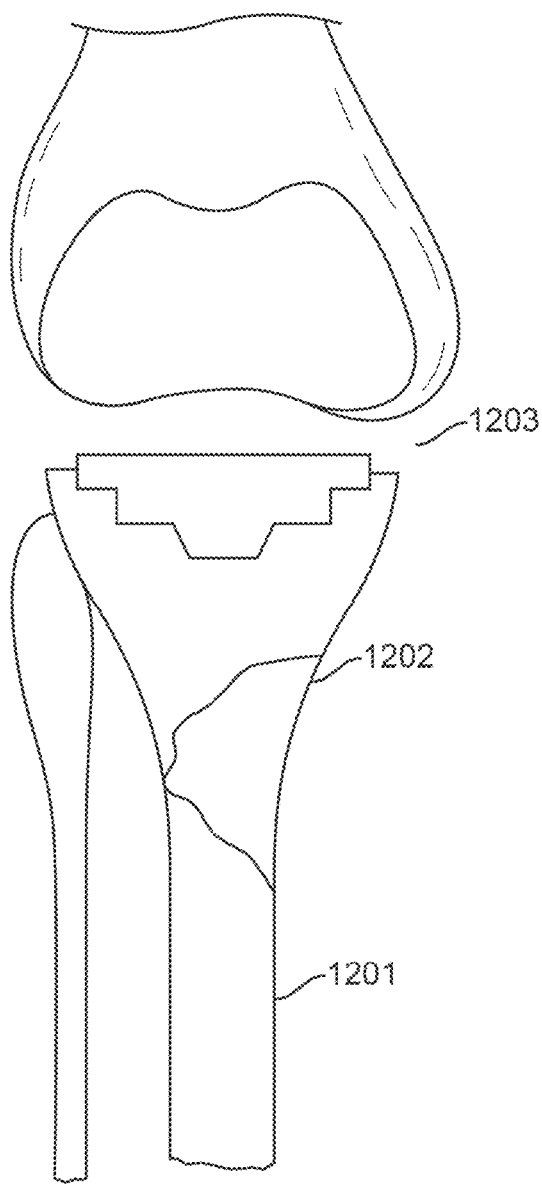
FIG. 12 is an illustration including a fracture below the tibial tray.

FIG. 12: Problem #3—Fracture Below Tibial Tray

Depicted in FIG. 12 is the Native Tibia 1201 as well as potential future fracture of the proximal tibia, labeled 1202. Please note that the Fracture Pattern 1202 is only one potential fracture pattern that could exist below the tibial tray component of the total knee arthroplasty. The tibial tray component is labeled in this diagram as 1203.

Figure 13:
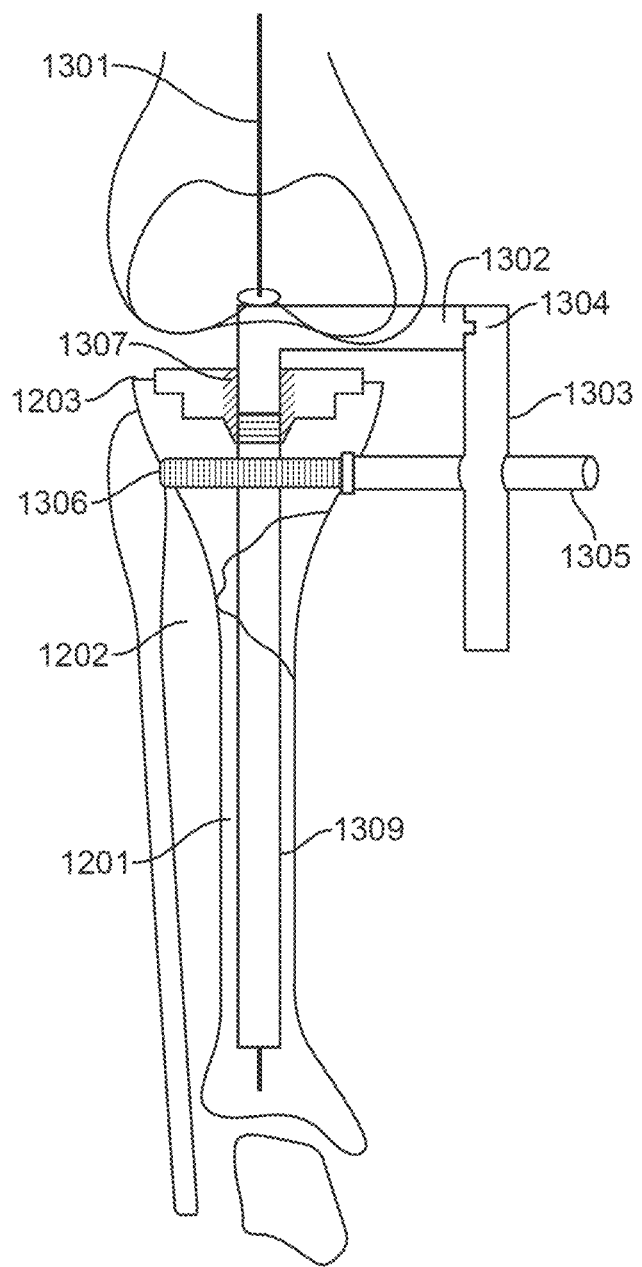
FIG. 13 is an illustration of an embodiment including: Modified Tibial Tray to accommodate contingent fracture management.

FIG. 13: Solution #5—Modified Tibial Tray to Accommodate Contingent Fracture Management Depicted in FIG. 13 is one embodiment of the fracture management device to address fracture of a Tibial Component 1203 with the fracture depicted as 1202. A Guide Wire 1301 would be inserted at the time of fracture fixation through the Tibial Component 1203 through the Interface 1307. Over this guide wire would be placed a Tibial Nail Fixation Device 1309 with the insertion of 1309 being facilitated through an aligning device, such as a Cannulated Outrigger 1302 and aiming arm, such as Proximal Targeting Device 1303. Further details of a coupling point between 1302 and 1303 are depicted as 1304. Providing for appropriate targeting and placement of the Fixed-Angled Locking Screw 106 would be the Screw Alignment Cannula 1305 inserted through the Proximal Targeting Device 1303. The advantage of this design provides for medullary fixation of the fracture of the Native Tibia 1201 with the fracture pattern depicted as 1202. The ability to have the Contingent Prosthetic Accommodation Portal 1307 be in place prior to the fracture provides a significant clinical advantage for potential fracture fixation. The biomechanical and biological advantages of medullary fixation for a fracture pattern depicted as 1202 of the Native Tibia Bone 1201 are extensive. Ease of operation, maintenance of the current total knee arthroplasty, as well as preservation of biology are all distinct advantages. The addition of biomechanical favorability with the medullary implant is also noted.

Figure 14:
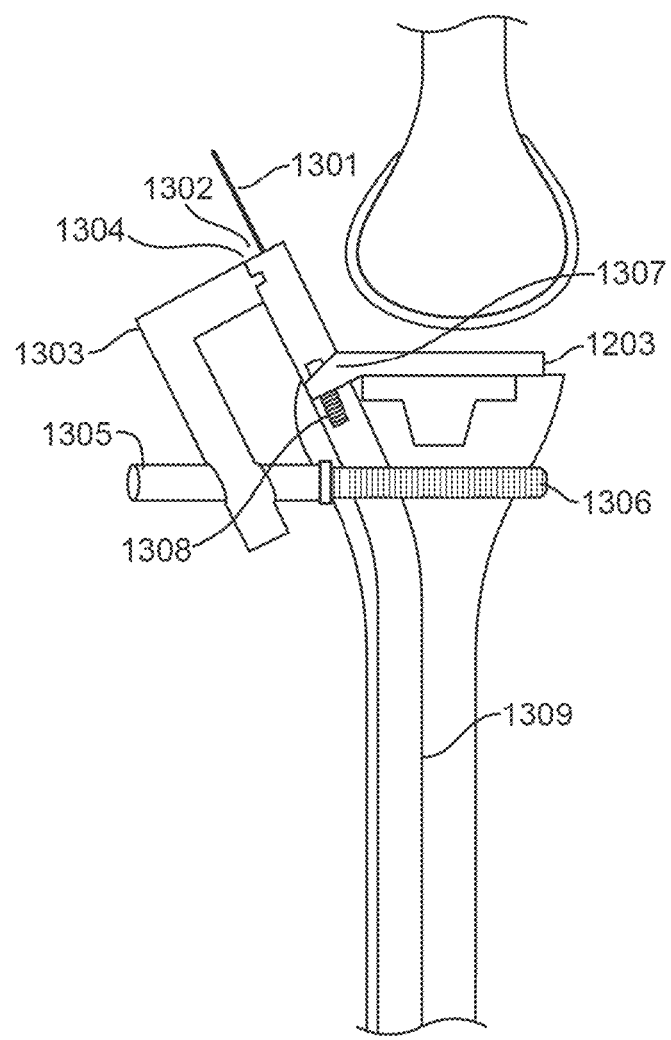
FIG. 14 is an illustration of an embodiment including: Lateral Projection of (FIG. 13) Modified Tibial Tray to accommodate contingent fracture management.

FIG. 14 Lateral Projection of (FIG. 13) Modified Tibial Tray to Accommodate Contingent Fracture Management FIG. 14 represents a Lateral Projection of (FIG. 13) an embodiment of Modified Tibial Tray to accommodate contingent fracture management. Through this lateral projection the Modified Tibial Nail 1309 is inserted through the Customized Tibial Prosthetic Tray 1203 through the Interface 1307. The nail is inserted over a Guide Wire 1301 with this insertion facilitated by an aligning device, such as the Cannulated Outrigger 1302 as well as Proximal Targeting Device 1303. By interlocking the screw 1306 alignment is assured through the Alignment Cannula 1305, with Interlocking Screw 1303 being placed utilizing this mechanism. To secure fixation between the Tibial Nail 1309 and the Tibial Tray 1203 with this Contingent Prosthetic Accommodation Interface 1307 is a Cannulated Coupling Interface 1308. This interface would provide for fixation between 1309 and 1203. As with the previous devices, the modification to the Tibial Tray 1203 would occur at the time of manufacture and be present as a contingent fixation option should a fracture of Native Tibia Bone 1201 occur in a fracture pattern depicted as 1202.

Figure 15:
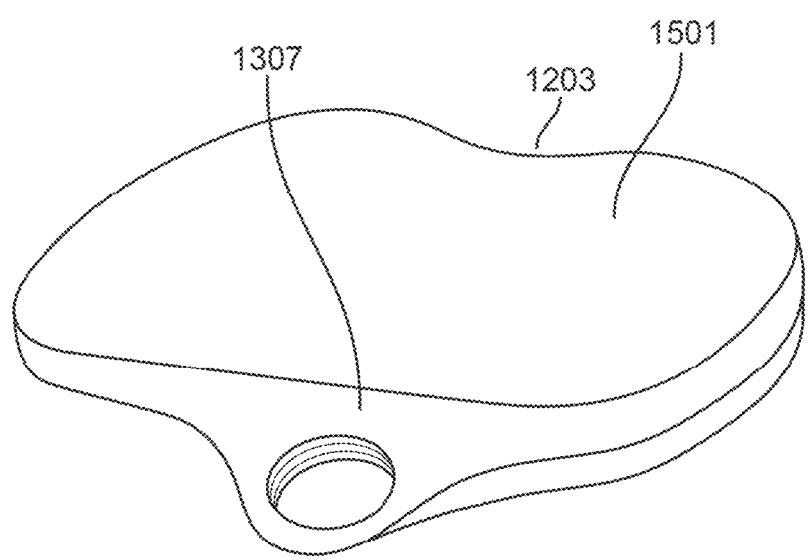
FIG. 15 is an illustration of an embodiment including: 2D rendition of (1203) Prosthetic Tibial Tray.

FIG. 15 2D rendition of (1203) Embodiment of a Prosthetic Tibial Tray

FIG. 15 represents a three-dimensional projection of an embodiment of the Prosthetic Tibial Tray 1203 with the Contingent Prosthetic Accommodation Portal 1307. Of note there is no modification to the articulating surface of 1203 depicted as 1501.

Figure 16:
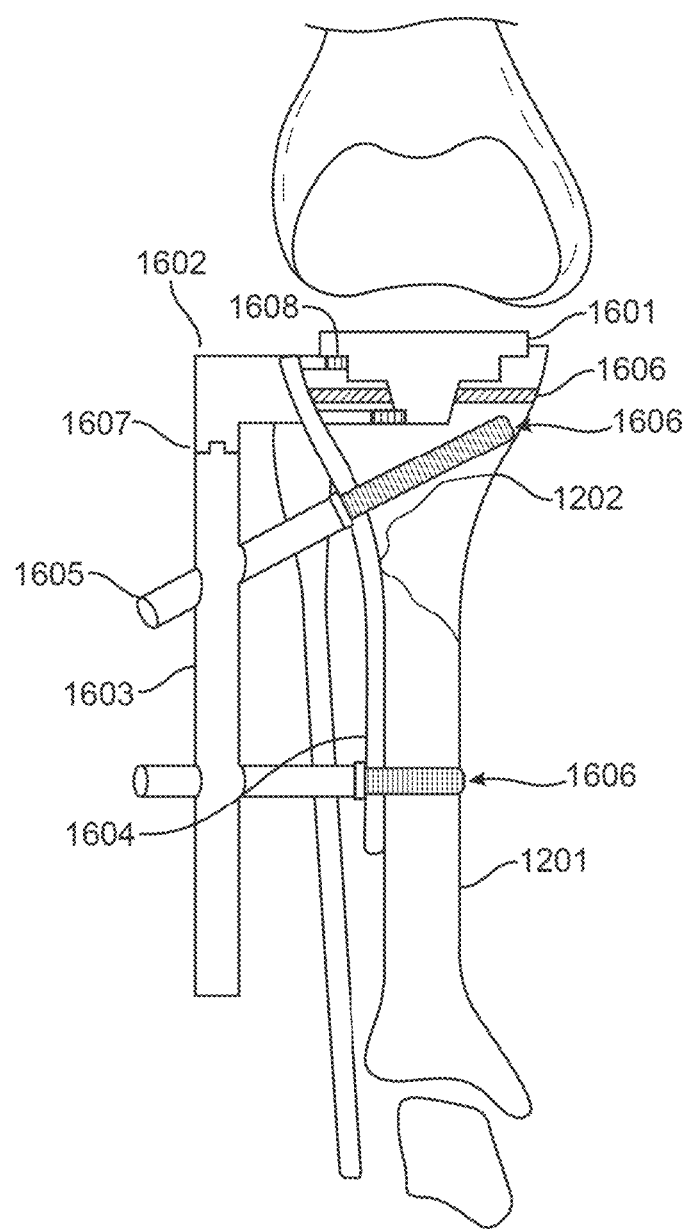
FIG. 16 is an illustration of an embodiment of Contingent Prosthetic Tibial tray accommodation for Proximal Tibial Locking Plate for management of Periprosthetic fracture management.

FIG. 16—Embodiment of Contingent Prosthetic Tibial Tray Accommodation for Proximal Tibial Locking Plate for Management of Periprosthetic Fracture Management Depicted in FIG. 16 is an alternative embodiment of fixation for fracture of the Native Bone 1201, depicted as Fracture Pattern 1202. The placement of the Tibial Tray 1201 would take place at the time of total knee arthroplasty. Fracture below the tibial tray, depicted as 1202, would occur and fixation of said fracture would be managed through the modification of the Tibial Tray 1201. The modifications in Tibial Tray 1201 are made to provide for the adjoining of Custom Outrigger 1602 that would thread into the Modified Tibial Tray 1601 at the Prosthetic Contingent Mounting Interface 1608. This would be through the plate labeled 1604. All three components, 1602, 1604, and 1601 would thus be intimately joined together to provide for appropriate targeting and fixation of Screws 1606. Attached to Proximal Plate Outrigger 1602 would be an aiming arm, such as Distal Targeting Device 1603 that adjoins 1602 through Coupling Point 1607. Through the Distal Targeting Device 1603 Alignment Cannulae 1605 are placed to align the trajectory of the Interlocking Screws 1606.

A distinct clinical advantage for the capacity to align and subsequently maintain the interface between the Tibial Fixation Plate 1604 and the Modified Tibial Tray 1601 relates to the capacity to maintain axial, sagittal, as well as coronal plane alignment both above and below fracture of the Native Tibia 1201, depicted as Fracture Pattern 1202. The plate is designed to be placed in a minimally invasive fashion to avoid compromise of the biology around Fracture 1202. Further clinical advantage is noted by the decrease in surgical time with predetermined targeting as well as enhanced biomechanical properties with the intimate association between the Tibial Plate 1604 and Modified Tibial Tray 1601.

Figure 17:
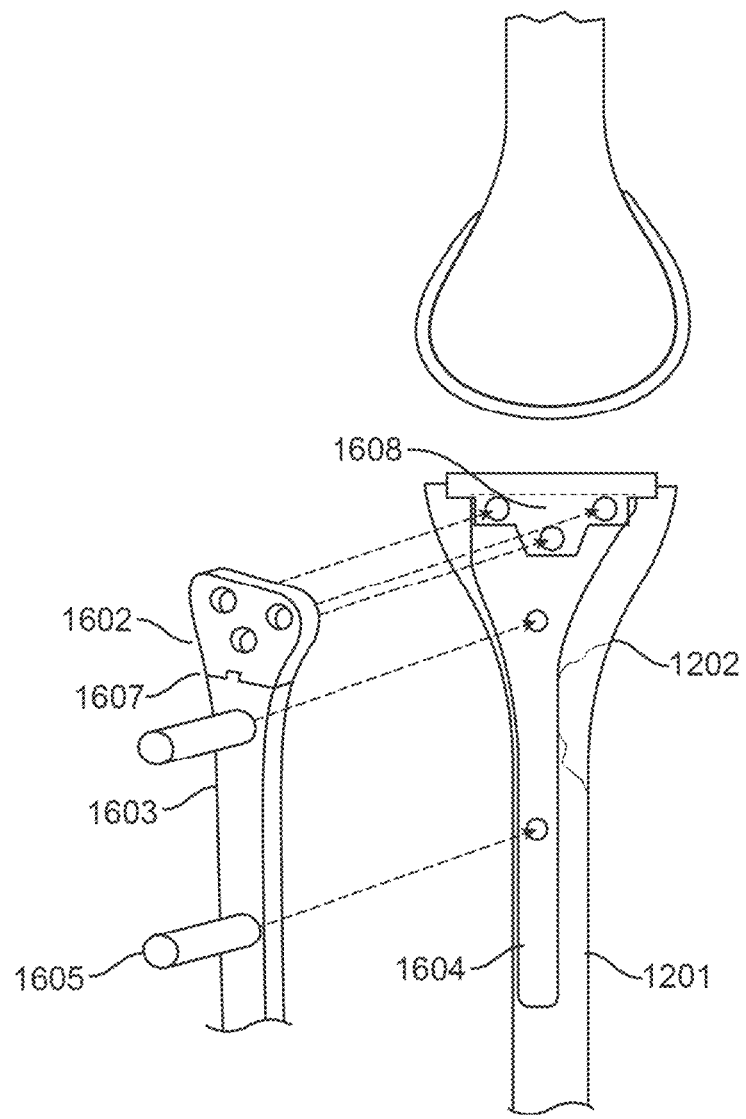
FIG. 17 is an illustration of a Lateral Rendition of (FIG. 16) an embodiment of Contingent Prosthetic Tibial tray accommodation for Proximal Tibial Locking Plate for management of Periprosthetic fracture management.

FIG. 17: Lateral Rendition of (FIG. 16) an Embodiment of Contingent Prosthetic Tibial Tray Accommodation for Proximal Tibial Locking Plate for Management of Periprosthetic Fracture Management A lateral projection depicted in FIG. 17 reveals further detail as to the interface between the Underlying Modified Tibial Tray 1601, Tibial Fixation Plate 1604, as well as the Proximal Plate Outrigger 1602 and aiming arm, such as Proximal Targeting Device 1603. This interface allows adjoinment of the tibial fixation plate directly to the Modified Tibial Tray 1601 at the Interface 1608. This adjoinment is facilitated through the placement of Angular Stable Interlocking Screws 1606. The placement being targeted through the Proximal Plate Outrigger 1602 as well as aiming arm, such as Proximal Targeting Device 1603 and cannulae 1605. With the intimate association between Tibial Tray 1601 and Tibial Fixation Plate 1604, the maintenance of axial, sagittal, as well as coronal alignment is assured.

Figure 18:
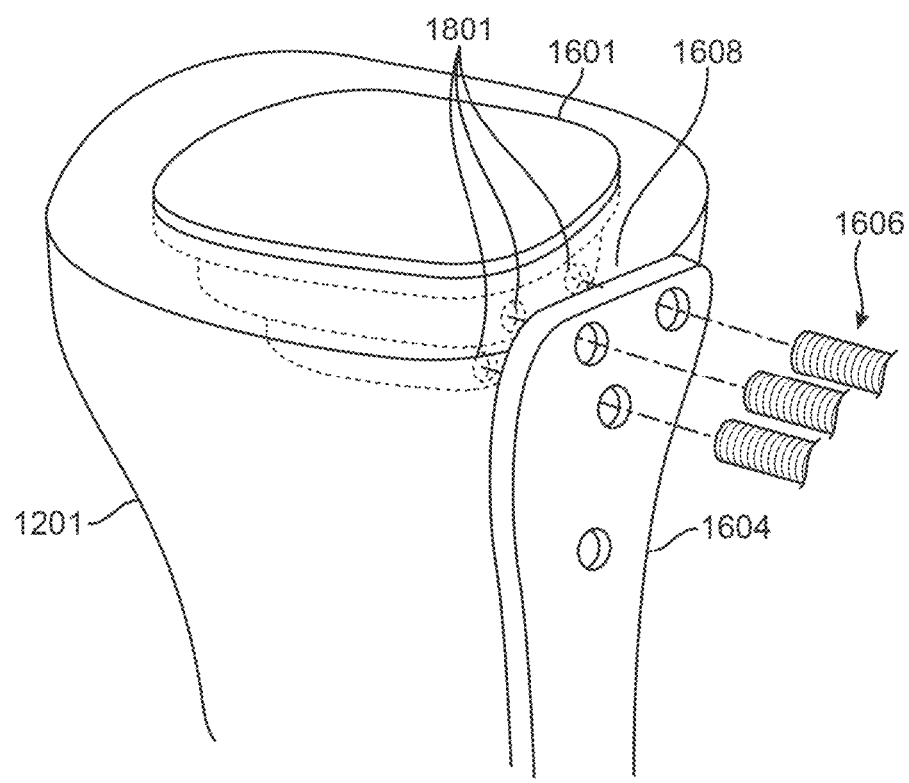
FIG. 18 is an illustration of an embodiment of Tibial Contingent Accommodation and Mounting of Tibial Plate.

FIG. 18: Detail of an Embodiment of Tibial Contingent Accommodation and Mounting of Tibial Plate In FIG. 18 a three-dimensional depiction of an embodiment of the tibial plate fixation device is noted. The Modified Tibial Tray Component 1601 would interface with Tibial Fixation Plate 1604 through the region depicted as 1608. Tibial Tray Contingent Plate Accommodation Mounting Holes 1801 would be present at the time of manufacture. The Tibial Tray Component 1601 would be placed at the time of total knee arthroplasty. Contingent Mounting Holes 1801 would be in place and available to be utilized for fracture fixation should the need arise. These mounting holes would accommodate the Angular Stable Locking Screw 1606 placed to provide for an interface and secure adjoining of Tibial Fixation Plate 1604 to Tibial Tray Component 1601 through Mounting Holes 1801. This mounting interface further assures the maintenance of axial, sagittal, as well as coronal plane alignment. The Tibial Tray Contingent Plate Accommodation Mounting Holes are labeled 1801.

The above-described embodiments of devices provide for a variety of fracture fixation options should a fracture occur after total hip arthroplasty or total knee arthroplasty. The current state of fixation of above-said fracture revolves around devices that are designed to avoid originally placed femoral or tibial components. The ability to pre-engineer fracture fixation contingent solutions into femoral or tibial components provides for a distinct clinical advantage in the planning and execution for periprosthetic fracture fixation. With a multitude of different fracture patterns that could clinically exist, current solutions for the variability of fracture patterns revolve around the use of either an external bone plate or an internal medullary rod/nail. None of the devices that currently exist have a pre-engineered solution to intimately associate with the previously placed total hip arthroplasty or total knee arthroplasty. The Proximal Tibial Plate Contingent Mounting Holes 1801 would be in place and present at the time of manufacture. The Tibia fixation plate and further the Tibial Tray Modification 1307 Entry Portal 13 below said component. This component being labeled the further construct ability the depiction of the in the FIG. 8 as well as 503 would be inserted at the time a total knee arthroplasty would be performed.

Figure 19:
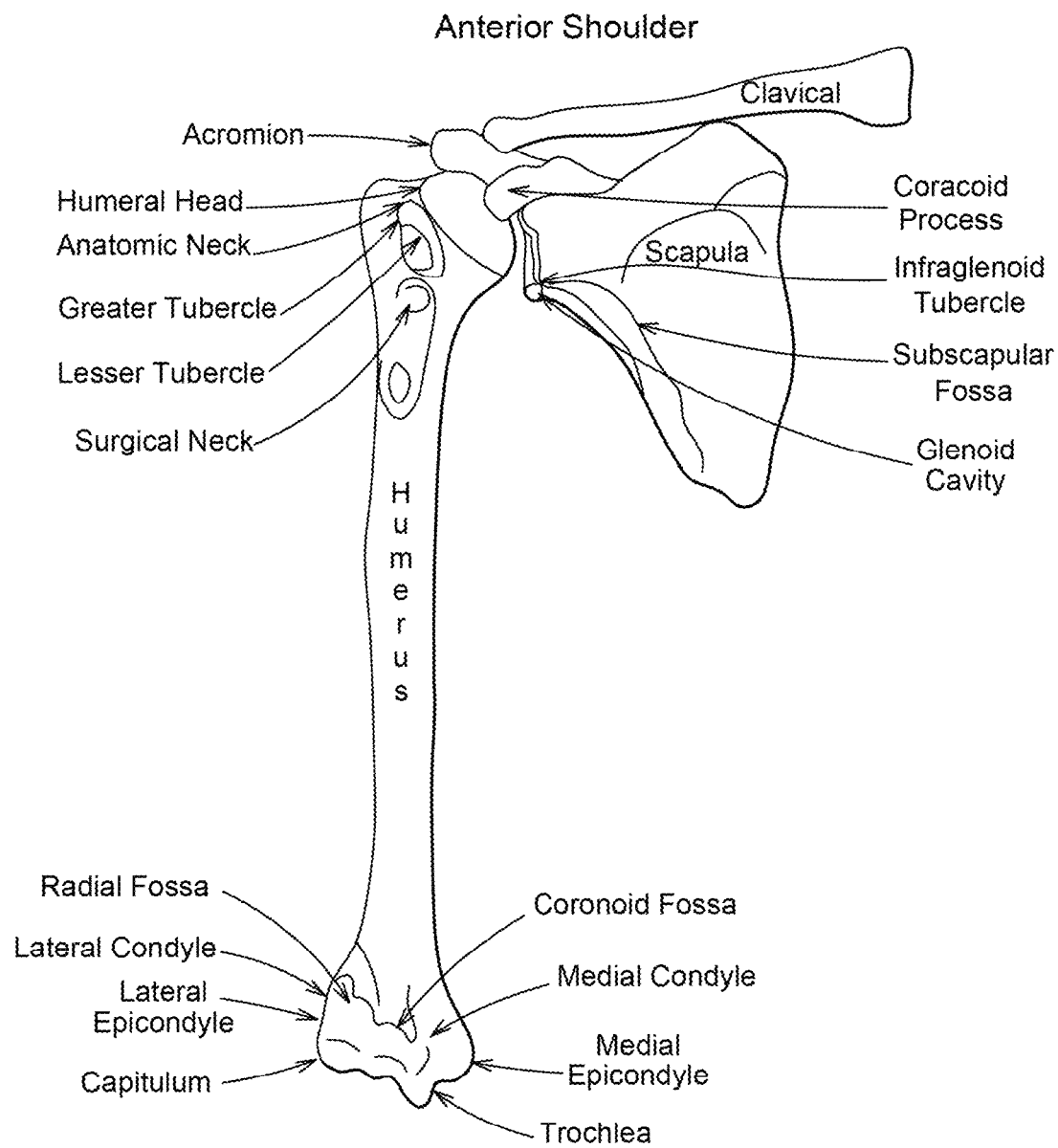
FIG. 19 is a reference diagram of a human anterior shoulder showing the humerus and glenoid cavity.

FIG. 19 is a reference diagram of a human anterior shoulder. Of particular interest to the present discussion is the humerus and glenoid cavity.

Figure 20:
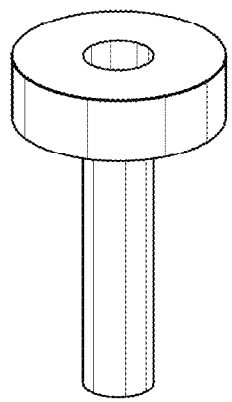
FIG. 20 is a more detailed view of a notched cap used with prosthetic having a core.
Figure 20:
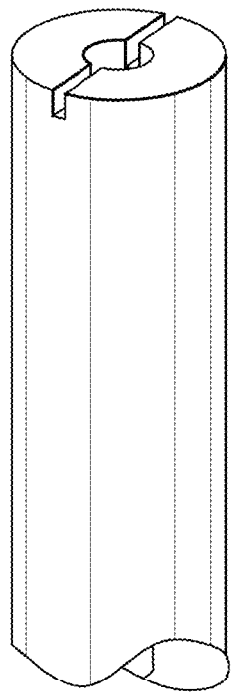

FIG. 20 is a more detailed view of a notched cap used with prosthetic having a core, to be described in more detail below.

Figure 21:
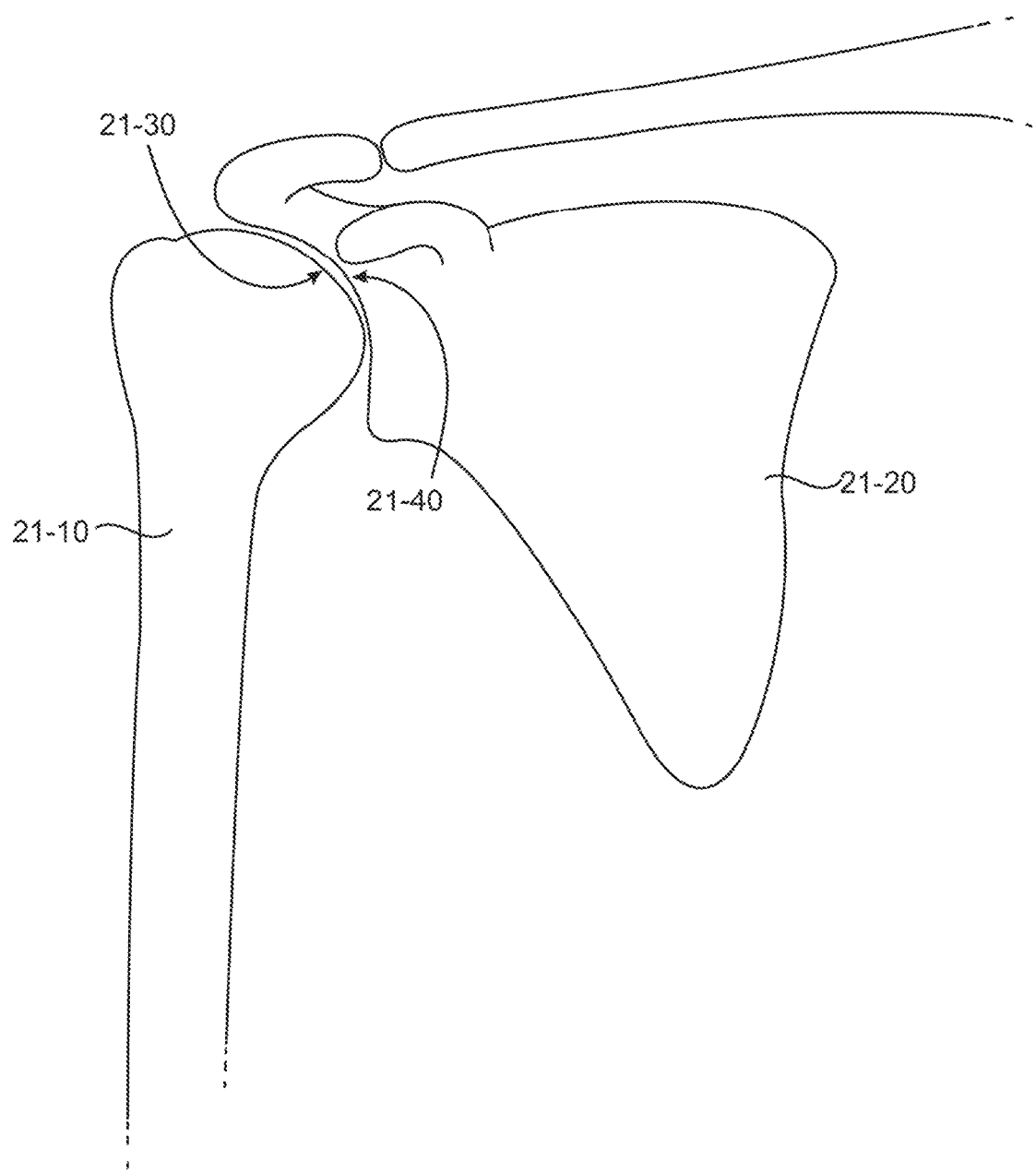
FIG. 21 is a more detailed view of a native shoulder.

FIG. 21 illustrates an intact proximal humeral shaft (designated with numeral 21-10). The intact scapular body 21-20 includes intact articular surface of the proximal humerus identified at 21-30. The intact articular surface of the glenoid is identified as 21-40.

Figure 22:
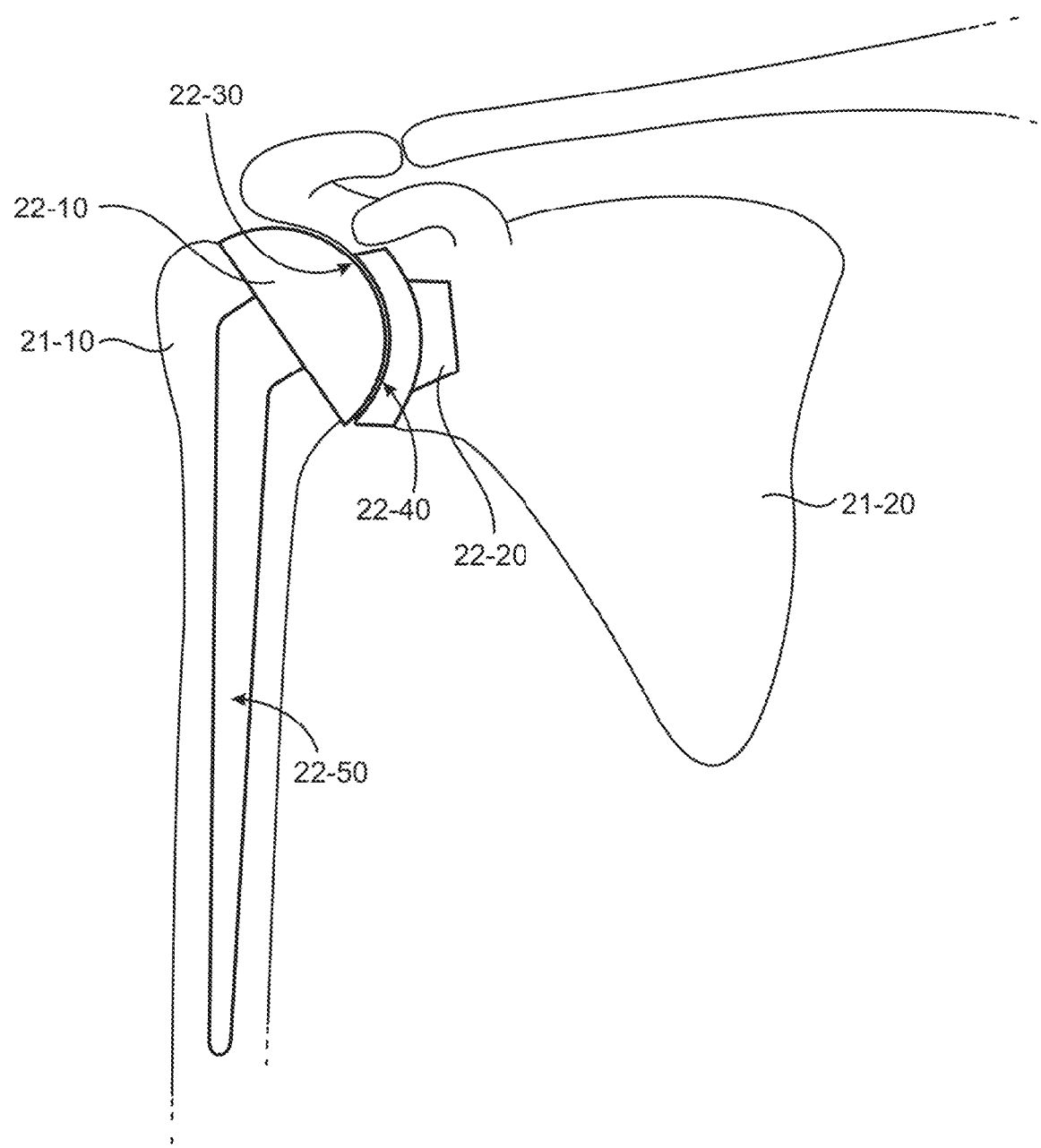
FIG. 22 illustrates a shoulder prosthetic for total arthroplasty without a hollow core component.

FIG. 22 is an overall depiction of a standard total shoulder arthroplasty with replacement of the proximal humerus as well as the glenoid. Specifics for the proximal humeral implant including the intact proximal humeral shaft 21-10 interfacing with humeral head arthroplasty component 22-10. The glenoid backing component is designated 22-20. The arthroplasty/articular interface 22-30 represents the humeral component of the articular interface. The glenoid of the articular interface is designated by 22-40. The arthroplasty component medullary stem is designated 22-50. This standard arthroplasty embodiment contains no contingent features in the event of a periprosthetic fracture. Contrasted to periprosthetic fractures around the hip and knee, periprosthetic fractures around a total shoulder arthroplasty represent a unique clinical challenge. The size of the medullary canal in conjunction with the distal humeral anatomy as well as proximal fill of the arthroplasty component limit greatly fracture fixation options in the event of a periprosthetic fracture.

Figure 23A:
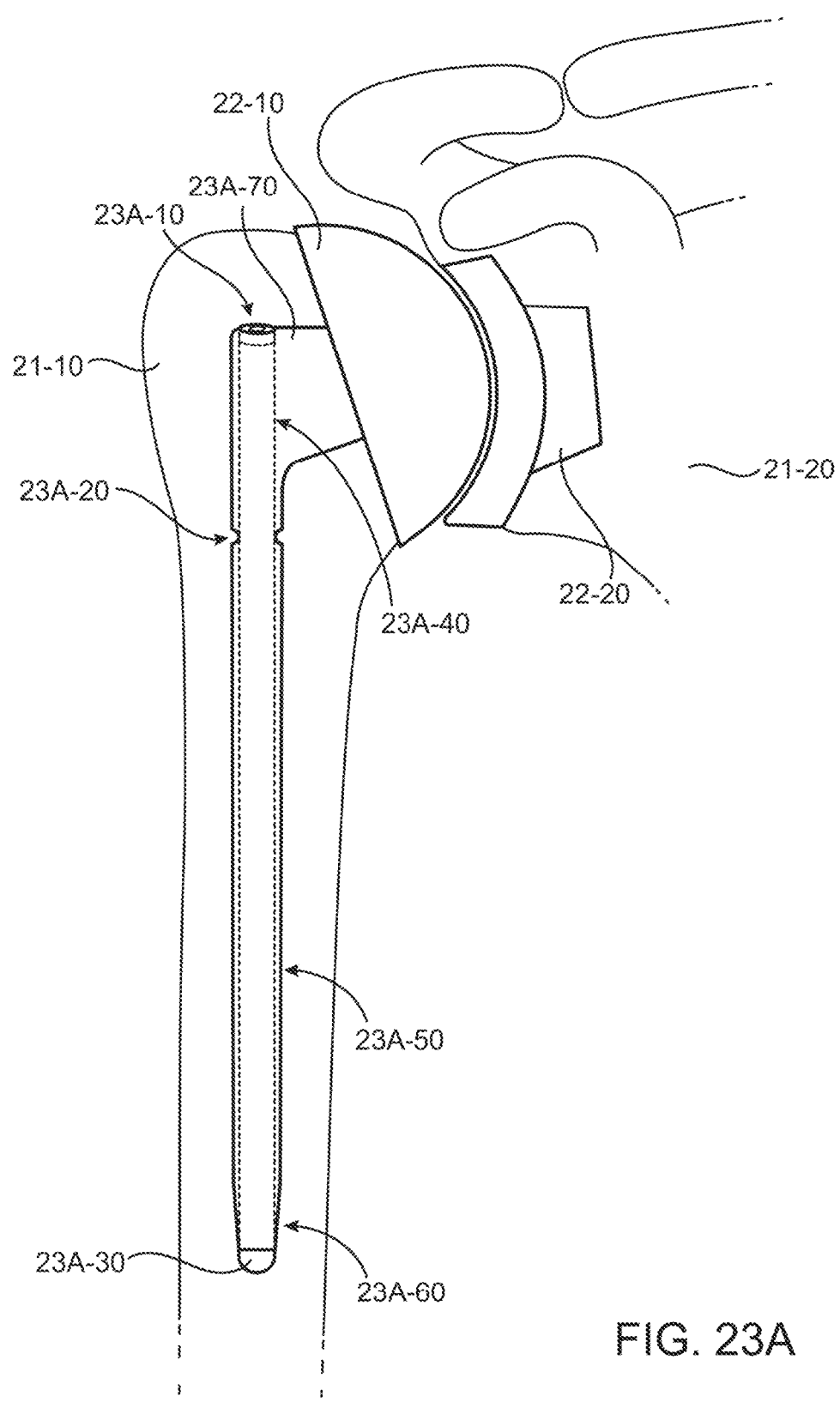
FIG. 23A shows a modified total shoulder arthroplasty with a prosthetic having an integrated solid core surrounded by an outer sheath.

The overall depiction of FIG. 23A represents a modified standard total shoulder arthroplasty with one embodiment detailing contingent features for fracture fixation. Details of the contingent features include the proximal locking cap 23A-10 securing the inner core 23A-40 within the stem component of the humeral arthroplasty. The locking cap 23A-10 was also depicted in FIG. 20. Further details for the stem component represent a combination of the inner core 23A-40 combined with the outer sheath 23A-10 50. The distal extent of the modified humeral stem component 23A-60 includes a taper with a radius to expose the core tip 23A-30. Finally, registration depiction 23A-20 represents registration between the outer sheath 23A-50 and the inner core 23A-40 providing for passage through the stem allowing for future fracture fixation device such as screw or other securing mechanism.

Figure 23B:
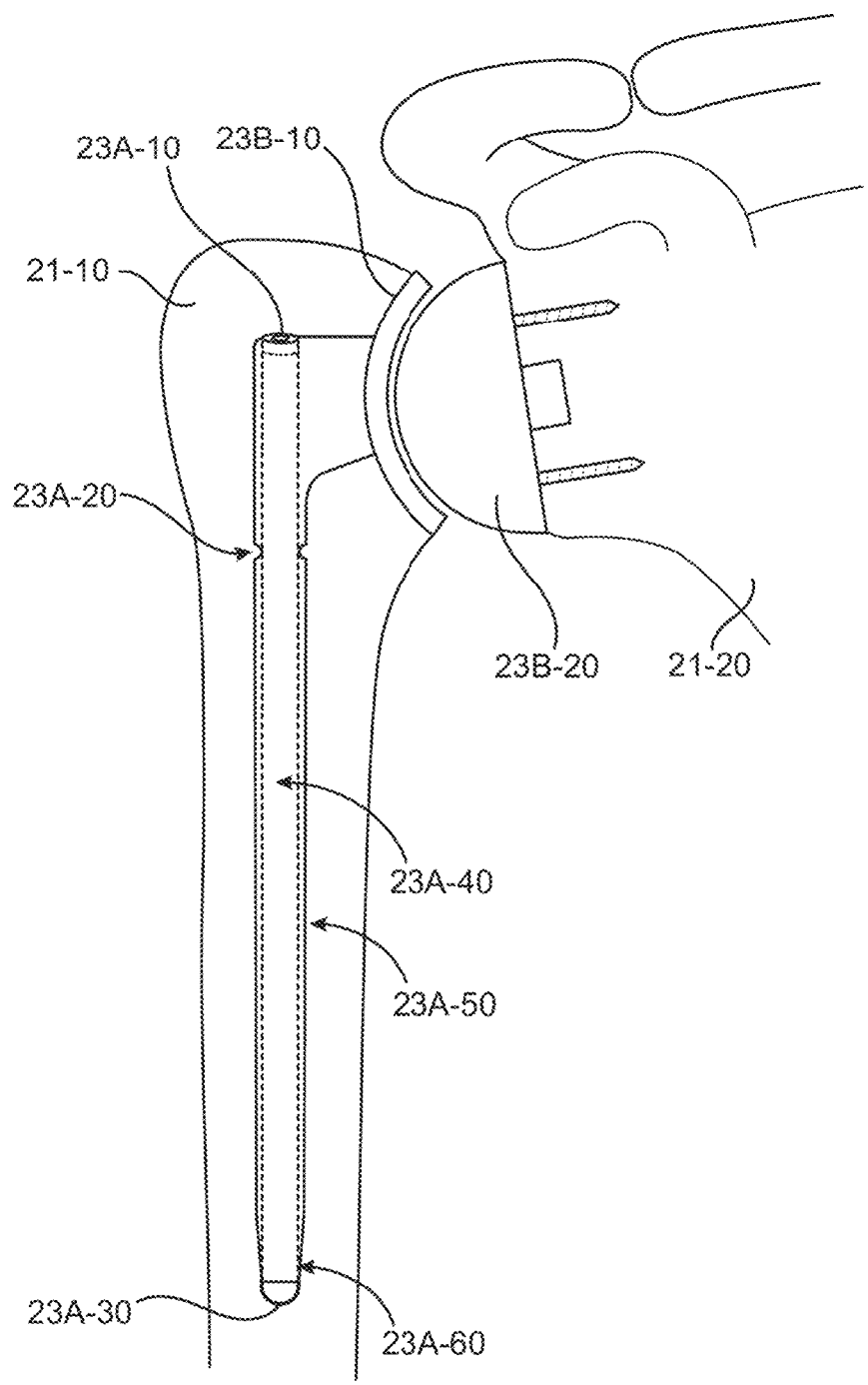
FIG. 23B contains an overall representation of a reverse total shoulder arthroplasty in an alternative embodiment.

FIG. 23B contains an overall representation of a reverse total shoulder arthroplasty in an alternative embodiment. Here the humeral articular surface 23B-10 articulates with the glenosphere 23B-20.

In any of the embodiments herein, the sheath 23A-50 may be a unitary component, or it may itself be a removable component. In the case of a removable implementation, the sheath may be constructed with threads on its outer diameter that engage a corresponding threaded opening insert in a main body of another prosthesis or another periprosthetic structure. Those implementations permit subsequenet replacement of the sheath 23-A.

Figure 24:
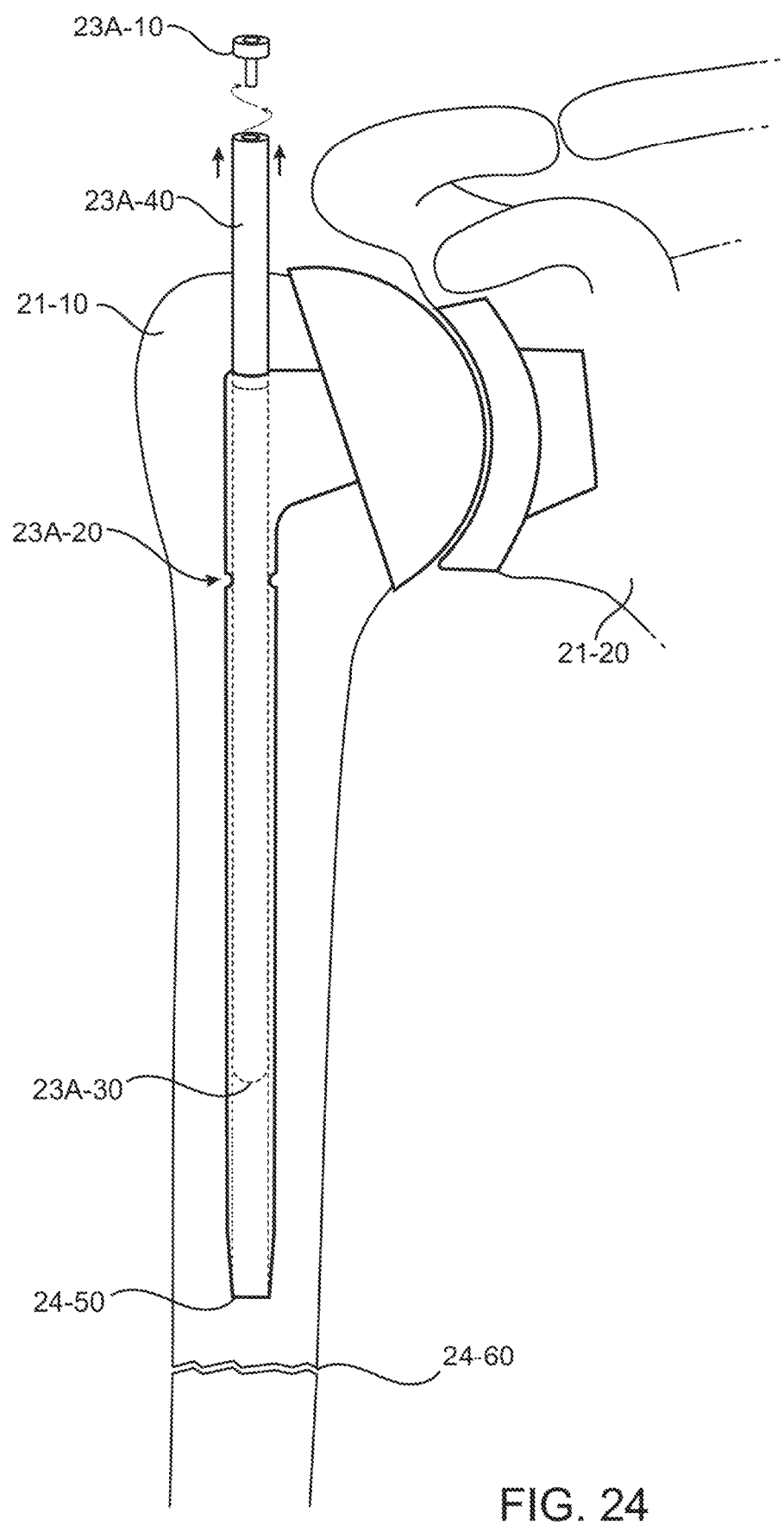
FIG. 24 shows partial disassembly of a cap and core of the prosthesis.

FIG. 24 depicts a periprosthetic fracture below the humeral stem component of a standard total shoulder arthroplasty. This embodiment now details the removal of locking end cap 23A-10 to provide for removal of inner core 23A-40. The distal extent of the outer sheath depicted at 24-50 now has an opening for the acceptance of a modified inner core that allows for fracture fixation and stabilization beyond the distal aspect of the fracture depicted at 24-60.

Figure 25:
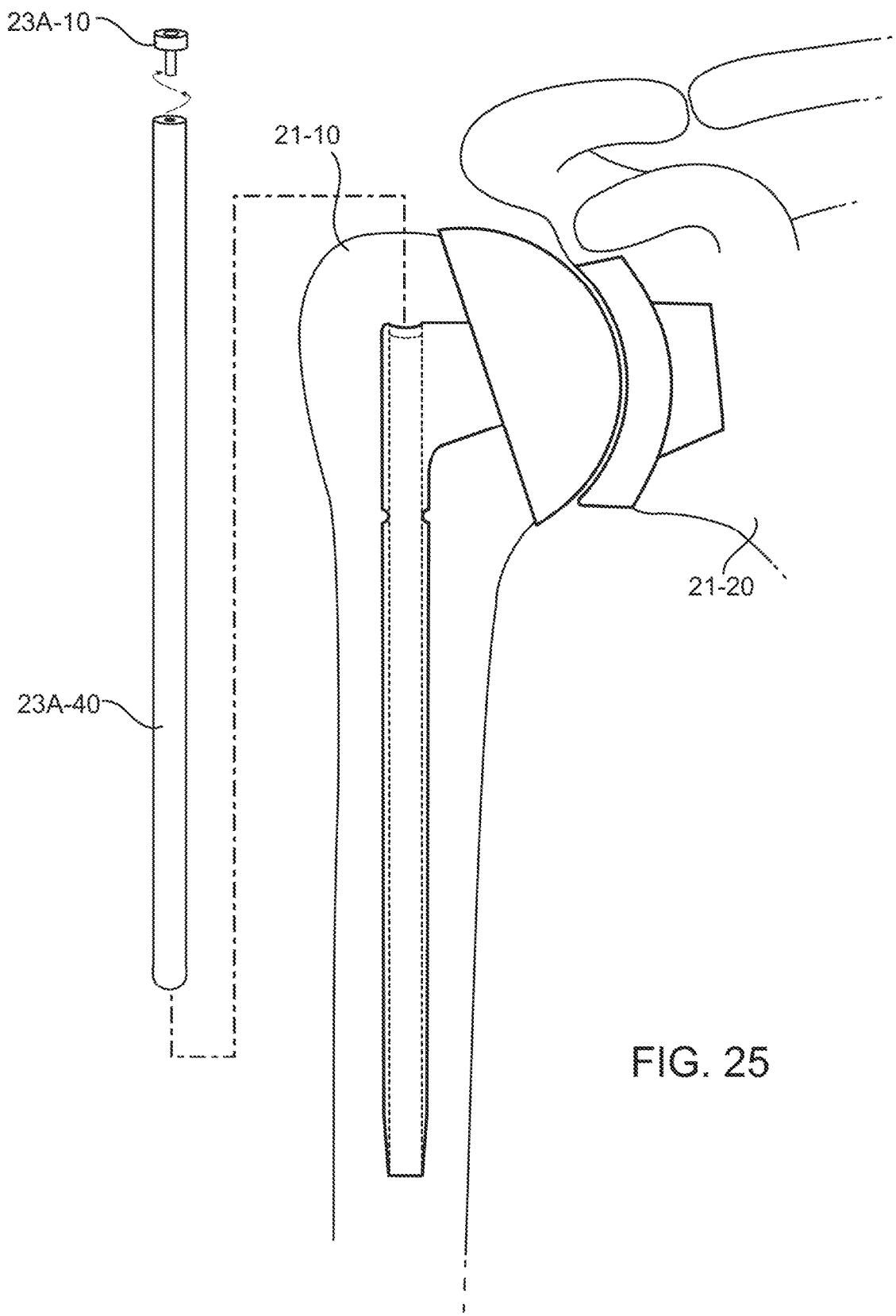
FIG. 25 is a further view of the disassembled core and cap.

FIG. 25 represents an expanded view with complete removal of locking cap 23A-10 as well as the inner core 23A-40 from the humeral stem component/sheath represented at 23A-50. This overall embodiment details a standard total shoulder arthroplasty. Another embodiment may represent a reverse total shoulder arthroplasty or some varying component of shoulder arthroplasty.

Figure 26:
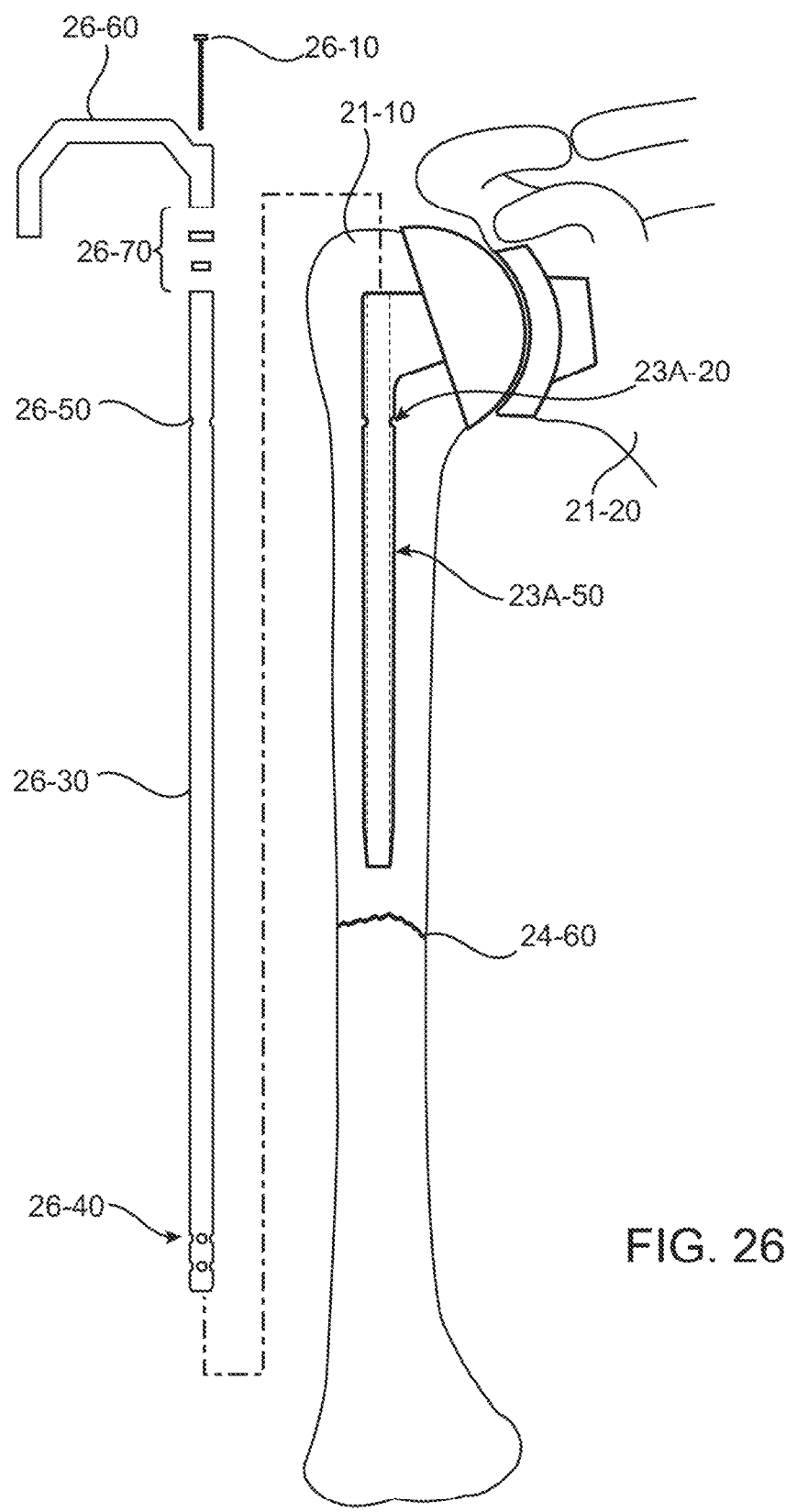
FIG. 26 is a view of a disassembled alignment arm and broken bone.

FIG. 26, again this is an embodiment of a standard total shoulder arthroplasty with a concomitant periprosthetic fracture. It is an overall depiction of one embodiment of a medullary fixation device. Specifics for one embodiment include a locking bolt 26-10 providing for attachment of aiming arm/outrigger 26-60 interfacing through locking washer mechanism 26-70, to an underlying medullary fixation device 26-30. Details of various embodiments of the locking mechanism for interfacing 26-50 with 26-60 will be described in subsequent figures. The embodiment of the medullary fixation device here depicts a registration 26-50 aligning with the intact humeral component sheath 23A-50 at location 23A-20. This provides for insertion, in one embodiment, of a locking screw for length and rotational control. Finally, the distal aspect of the medullary fixation device 26-30 is depicted at 26-40. The ability for insertion of interlocking device, one embodiment being a screw, allows for secure fixation of the distal aspect of the fracture below the intact humeral stem component and humeral component sheath 23A-50.

Figure 27:
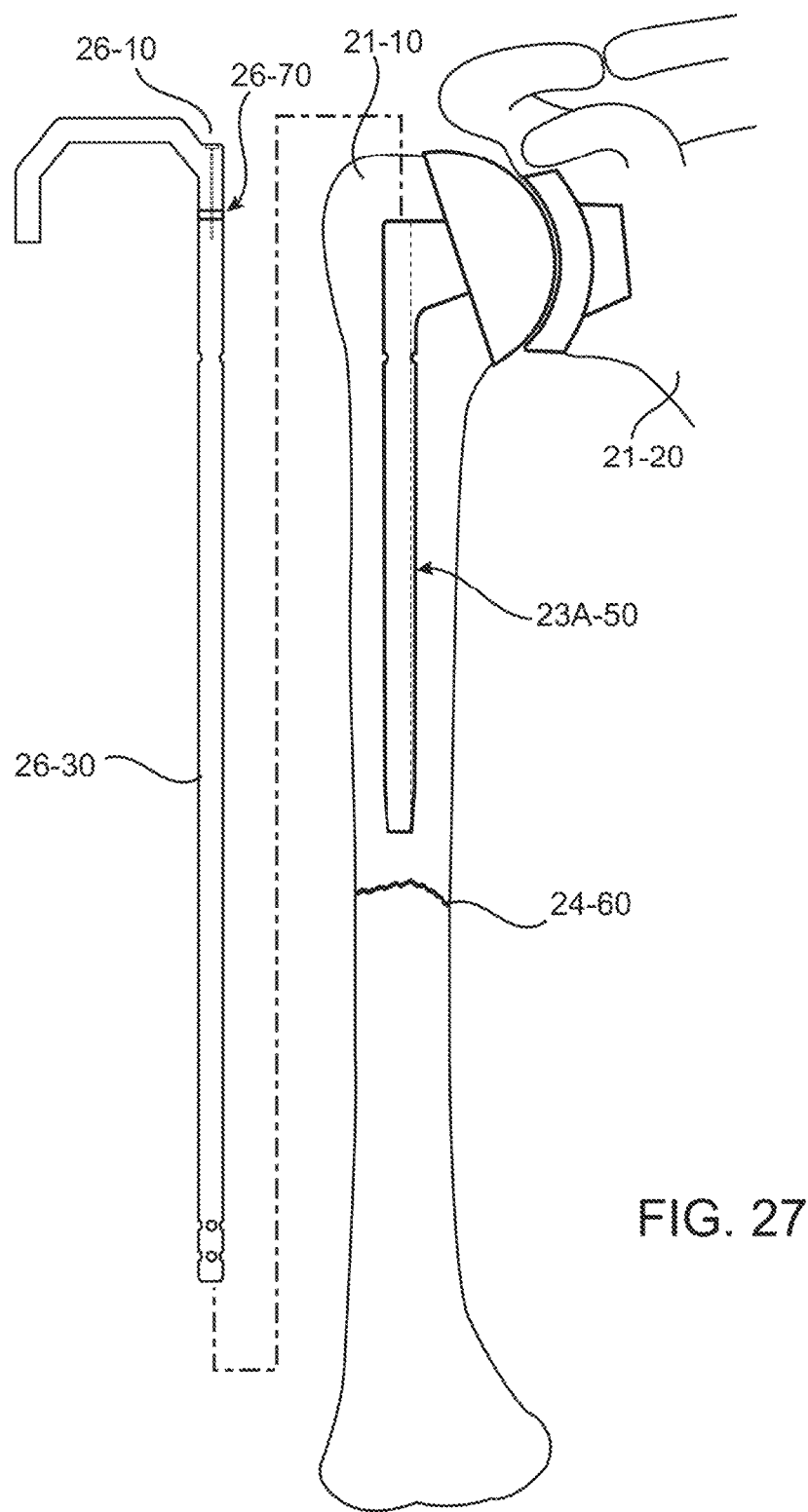
FIG. 27 illustrates the assembled alignment arm.

FIG. 27 represents further detail of the assembly for the medullary fixation device, with the components now being assembled through an interface depicted at 26-70. This provides for registration and rotational control as well as alignment between the medullary fixation device 26-30 and the intact humeral stem outer sheath 23A-50.

Figure 28:
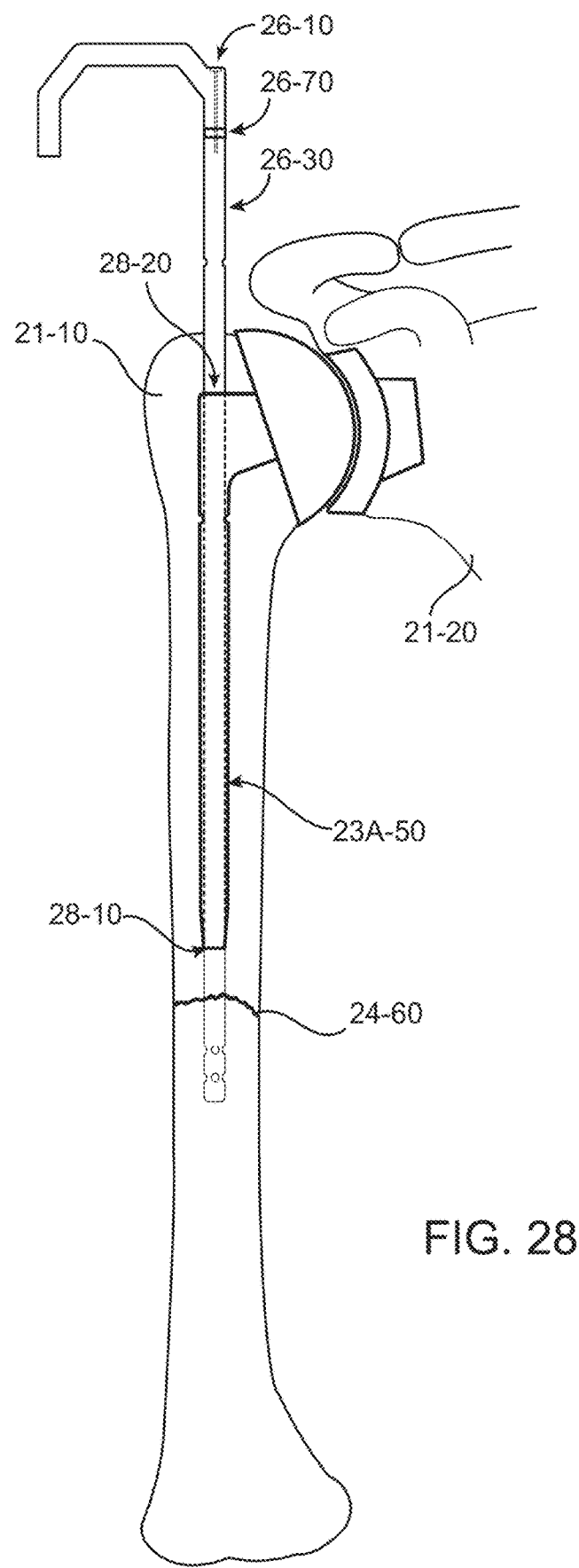
FIG. 28 shows an arm with the cannula for aligning fasteners to the sheath and a longer quote fracture fixation component

FIG. 28 shows the interface occurrence between the medullary fixation device 26-30 and the intact humeral stem sheath 23A-50. This interface occurs through the vacated inner core of the humeral stem sheath 23A-50. The proximal extent of the interface is depicted as 28-20. The medullary fixation device 26-30 now extends beyond the tip of the sheath 23A-50 to cross the fracture site into the intact distal humeral segment. The exit of the medullary fixation device 26-30 from the humeral steam sheath 23A-50 through an exit annulus depicted at 28-10. Previously, the inner core protruded beyond the exit point 28-10 associated with FIG. 23A, now the medullary fixation device extends beyond the tip of the sheath 23A-50 to include the intact distal extent of the fracture beyond the fracture line 24-60.

Figure 29:
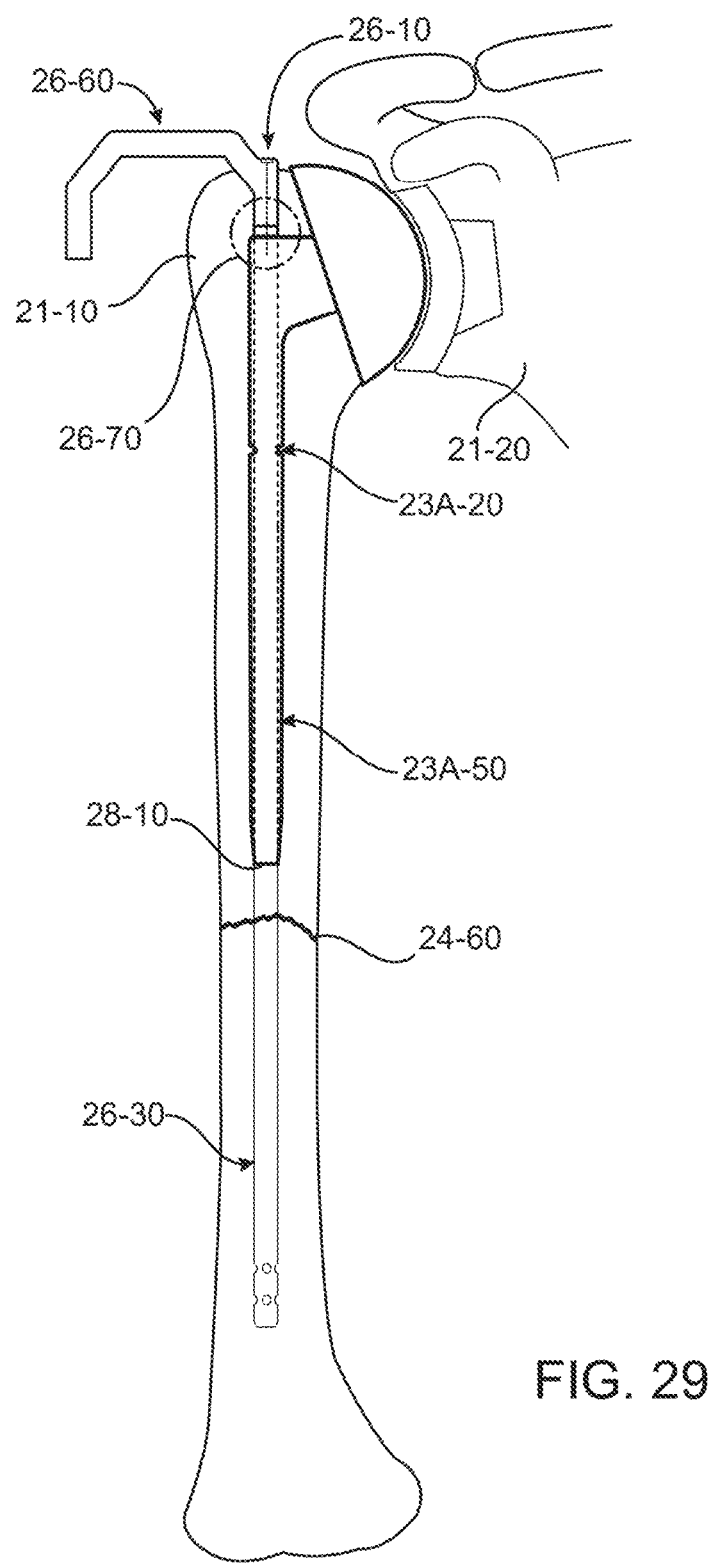
FIG. 29 is an assembled view.

FIG. 29 depicts one embodiment of a standard total shoulder arthroplasty with final placement of the medullary fixation device 26-30. The device does span across the fracture site at 24-60 exiting the outer sheath from the humeral stem at point 28-10. Continued registration is maintained between the outer aiming arm 26-60 with the medullary fixation device 26-30 through the locking screw 26-10. This provides for rotational control as well as distal alignment for targeting and insertion of interlocking devices, one embodiment being an interlocking screw. Coupling between the aiming arm and the medullary fixation device, representing the final insertion site, is depicted as an interface represented at 26-70—distally, the humeral stem sheath.

The distal aspect of the medullary fixation device and the interface locking mechanism 26-70 are associated with FIGS. 36 to 43. Details of this interface in various embodiments will be described to interface with medullary fixation device 26-30 specifics showing assembly of the medullary fixation device. Components would include humeral stem now being exposed for future insertion of fracture fixation device cap 23A-10 to provide for access to outer sheath 23A-50 and the inner core 23A-40. This allows for passage of fixation device for potential future fracture stabilization.

Figure 30:
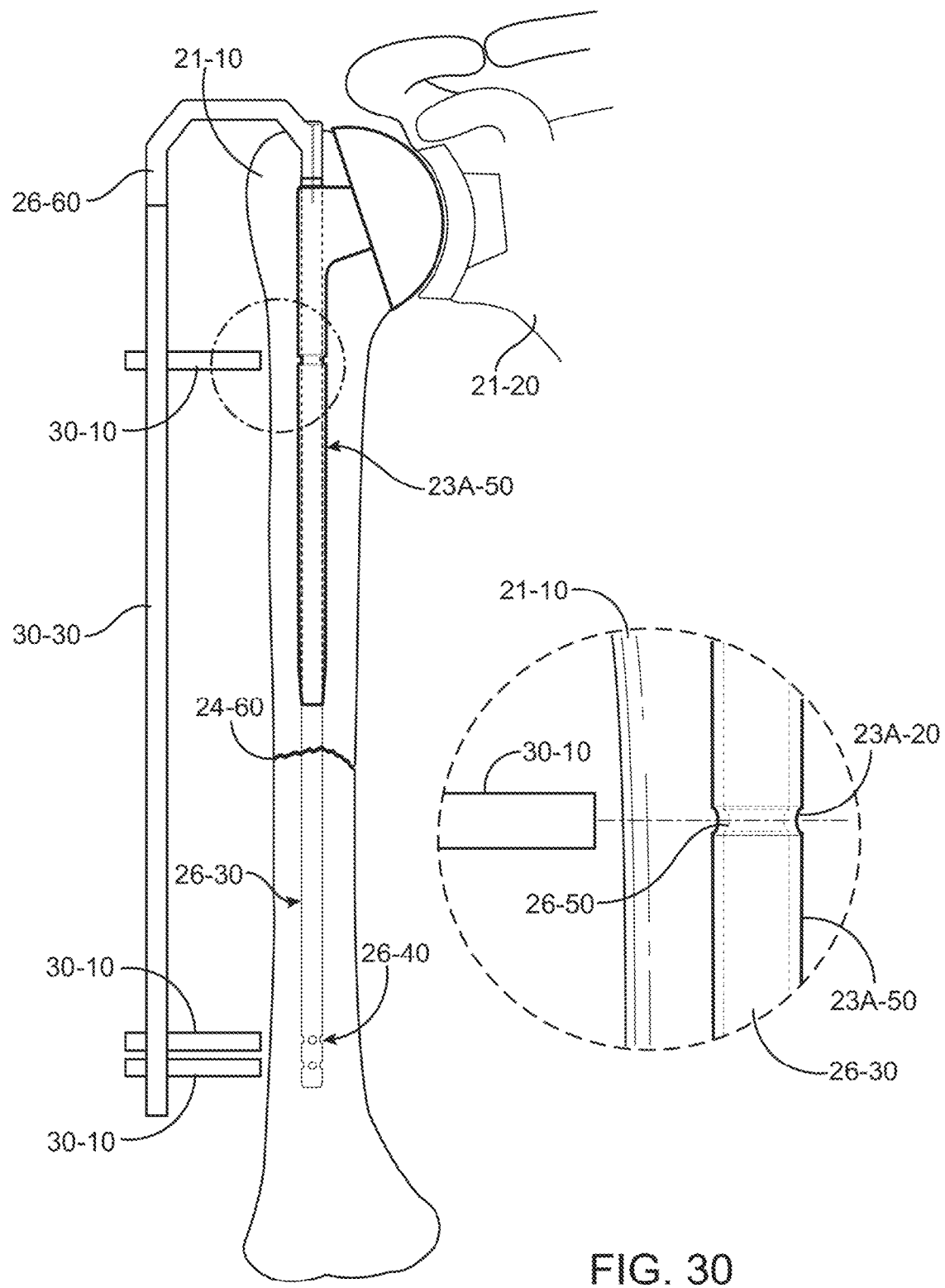
FIG. 30 illustrates screws inserted into clearance holes.

FIG. 30 shows another embodiment of a standard total shoulder arthroplasty containing contingent features for fracture fixation interfaced completely with the medullary fixation device. An aiming arm 30-30 now attaches to the outrigger 26-60 to provide for alignment and registration for interlocking screws both proximal and distal to the fracture site depicted at 24-60. Cannula to align the registration are shown at 30-10. Alignment allows for the passage of a interlocking device, one embodiment being a screw, that passes through the outer bone cortex, the humeral stem sheath 23A-50 as well as the medullary fixation device 20-30. One embodiment of these contingent features shows alignment of the outer sheath 23A-20 with the intramedullary fixation device 26A-50. The distal extent of the fracture fixation embodiment shows the aiming arm 30-30 containing the aiming cannula 30-10 to provide for registration and alignment allowing for the passage of a interlocking device, one embodiment being a screw, through the outer bone cortex, through the distal aspect of the medullary fixation device depicted as 26-40, through the innermost cortex of the distal humeral bone.

Figure 31:
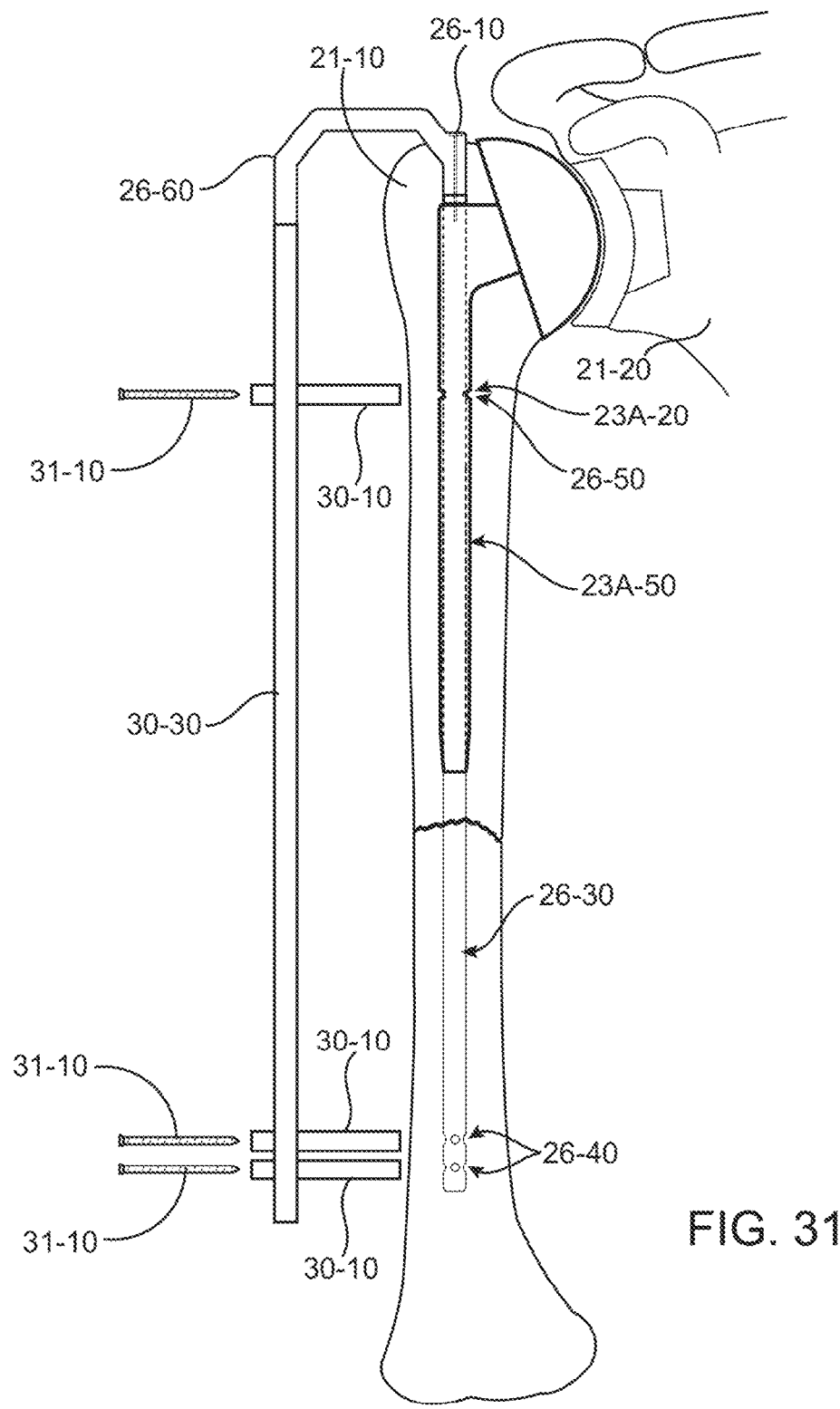
FIG. 31 another view of the assembly of the targeting arm and prosthesis.

FIG. 31 is an embodiment of a standard total shoulder arthroplasty with contingent features for fracture fixation using a medullary based device 26-30. Final insertion of the device across the fracture site is depicted. The aiming arm 30-30 with contained aiming cannula 30-10 both proximal and distal to the fracture site now has the ability for acceptance of interlocking screws depicted as 31-10. Features are depicted showing registration and alignment between the aiming arm 30-30 with inserted cannula 30-10 and alignment proximal to the fracture site through the outer humeral stem sheath 23A-20 as well as the intramedullary fixation device 26-30 at the site through the medullary fixation device 26-50. Distally, the registration alignment for passage of interlocking screws 31-10 occurs through the medullary fixation device 26-30 at holes 26-40.

Figure 32:
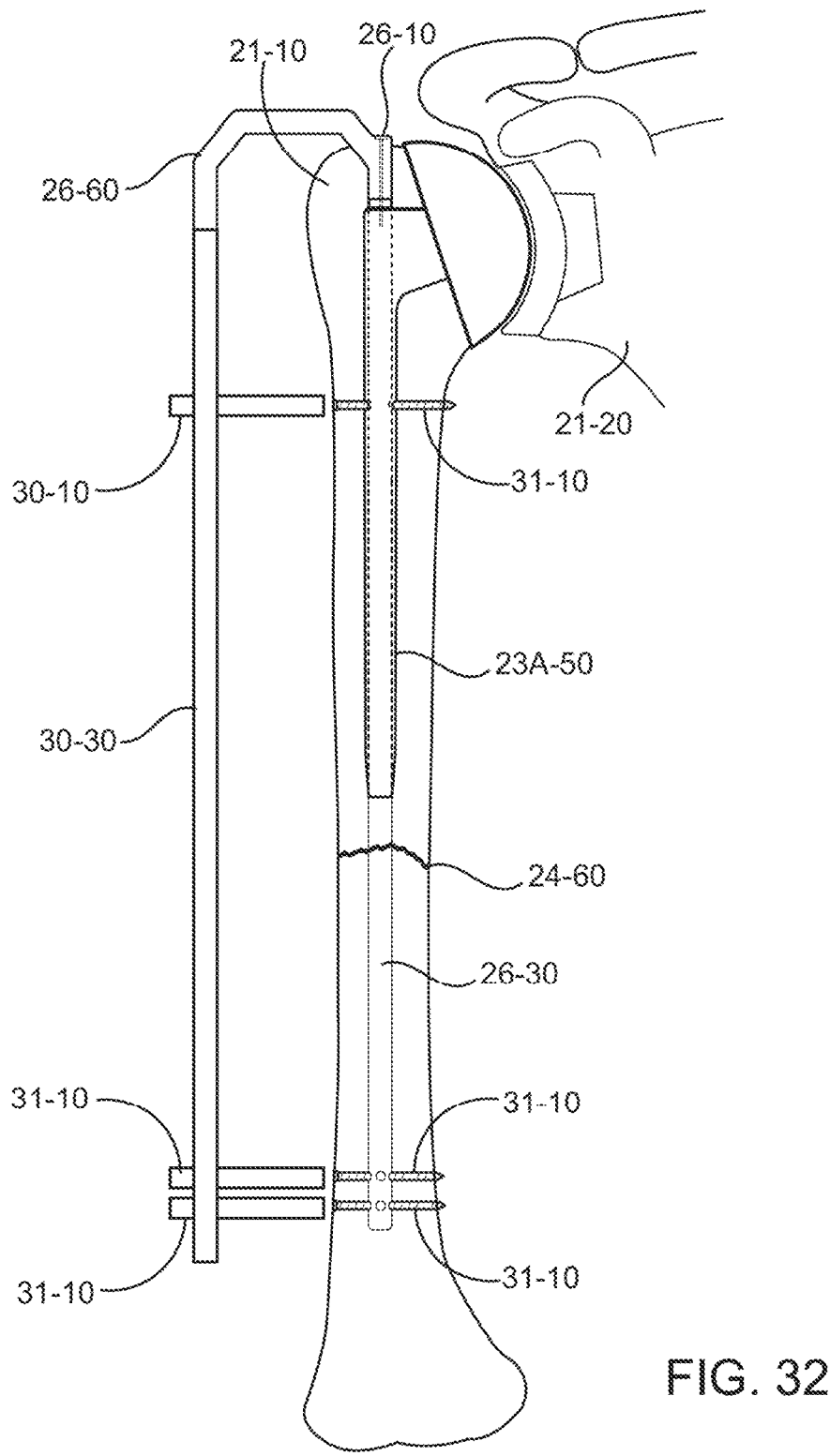
FIG. 32 is another view of the assembly.

FIG. 32 showing final insertion of interlocking screws 31-10 after final insertion of medullary fixation device 26-30, through the humeral stem outer sheath 20A-50. Distal interlocking screws are also depicted passing through the medullary fixation device 26-30 at site 26-40.

Figure 33A:
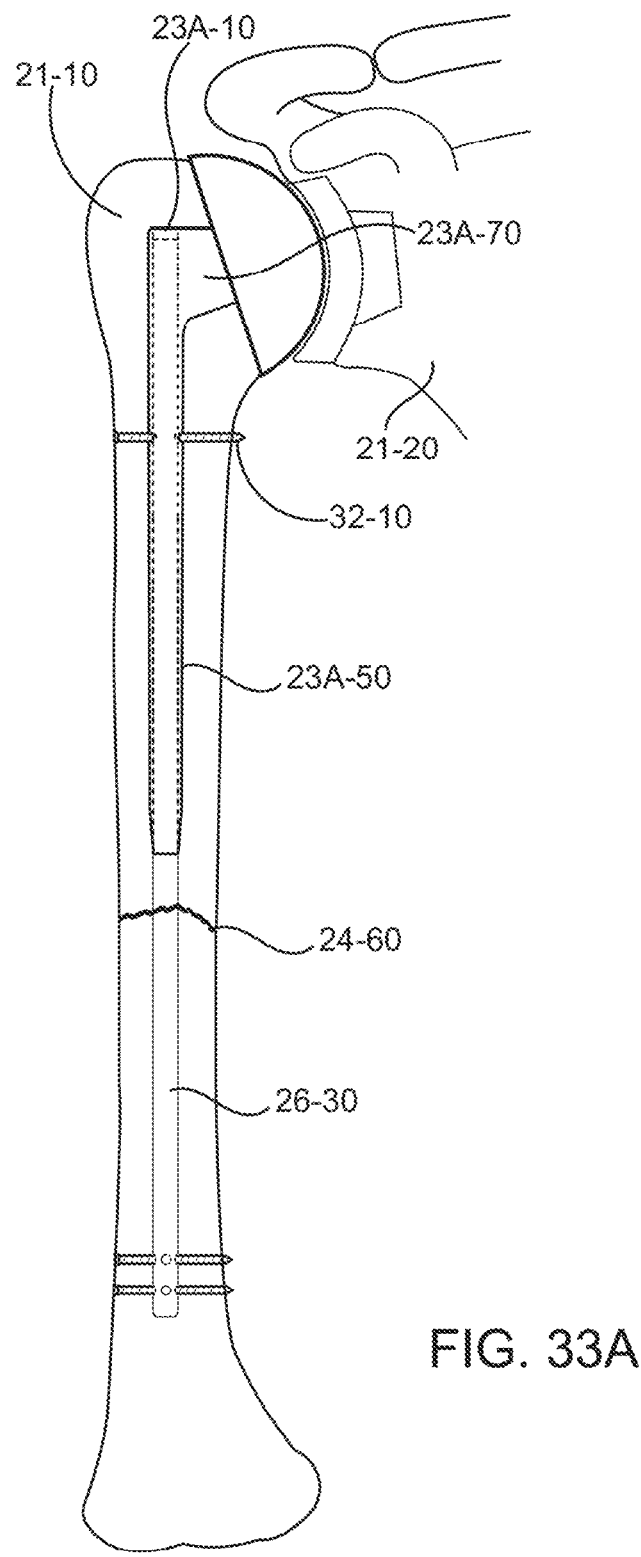
FIG. 33A is a modified total shoulder arthroplasty now showing a prosthetic fracture fixation component.

FIG. 33A depicts the final fixation construct with aiming arm and outrigger moved. This is for a standard total shoulder arthroplasty containing contingent features. The proximal locking cap 23A-10 has now been placed to provide for coverage over the medullary fixation device 26-30 and the underlying humeral stem component screws 23A70. One embodiment of the proximal locking cap 23A-10 allows for alignment and rotational registration between the intact humeral stem component 23A-70 and the underlying medullary fixation device 26-30.

Figure 33B:
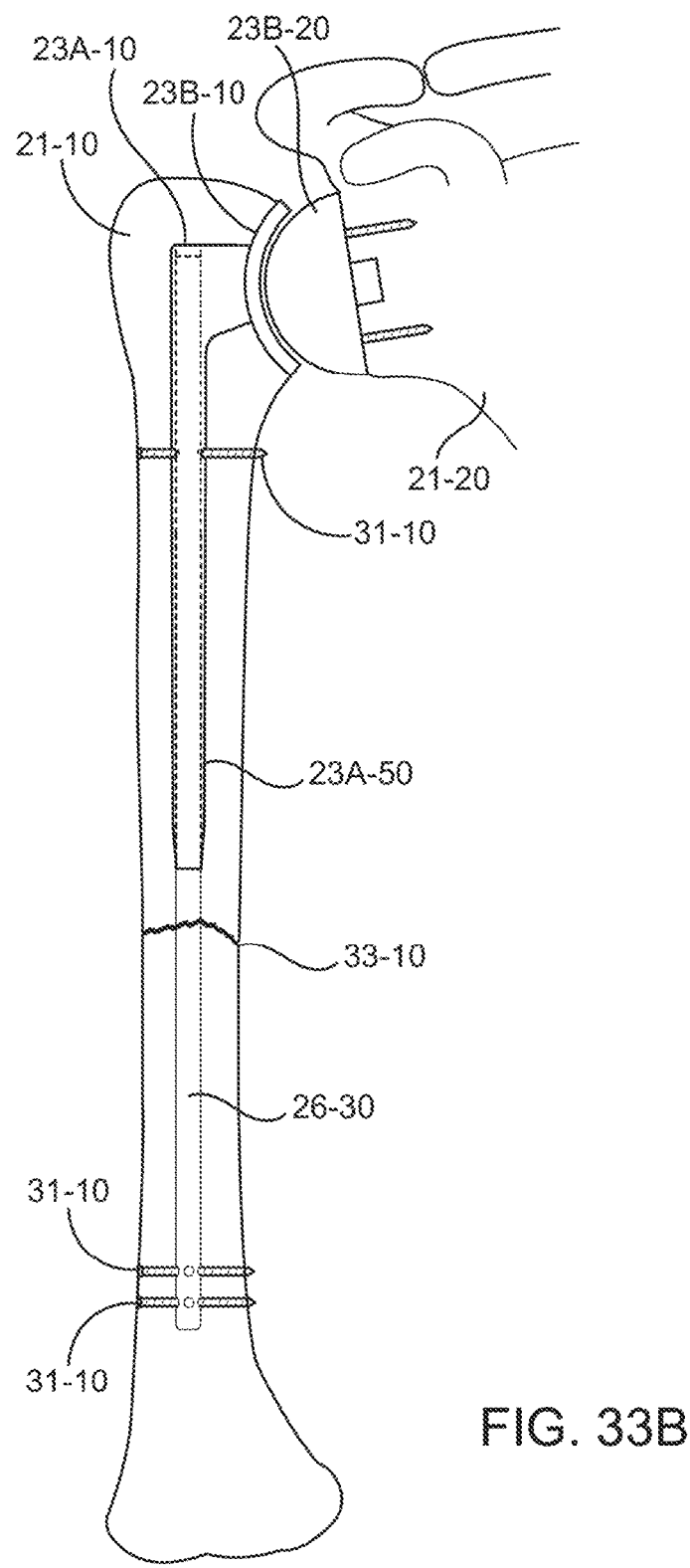
FIG. 33B shows a modified reverse total shoulder arthroplasty with the periprosthetic fracture fixation component having integrated core and outer sheath.

FIG. 33B represents an alternative embodiment of the humeral arthroplasty with contingent features for fracture fixation. This embodiment is described as a reverse total shoulder arthroplasty. The medullary fixation component 26-30 passes through the humeral stem sheath placed at 23A-50 and traverses the fracture site for medullary fixation. The previous embodiment detailing the assembly of the outrigger 26-60 with the aiming arm 30-30 and alignment cannula 30-10 is equally applicable for the alignment and insertion of interlocking screws 31-10 both proximal and distal to the fracture site at 24-60 through the outer core.

Figure 34:
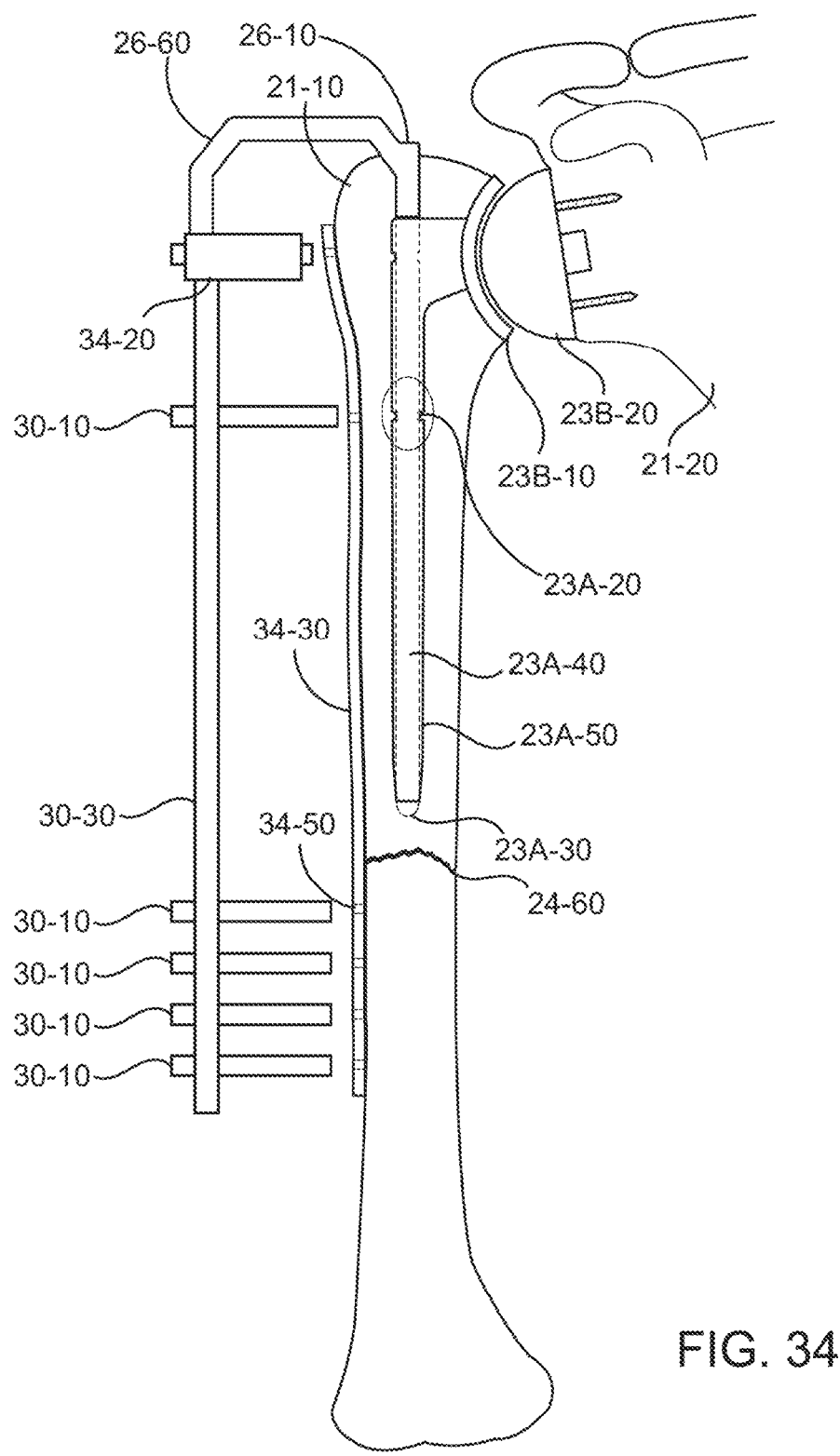
FIG. 34 shows a modified reverse total shoulder arthroplasty with fracture fixation and a registration outrigger plate.

FIG. 34 represents a reverse total shoulder arthroplasty with contingent features for fracture fixation. This embodiment depicts an extra-medullary fixation device, that being a plate, depicted at 34-30. The outrigger/aiming arm 26-60 interfaces with the intact humeral stem component comprised of outer sheath 23A-50 and inner core 23A-40. The plate 34-30 attaches to the outrigger/aiming arm 26-60 using plate attachment device 34-20. The specific embodiments of the aiming arm 30-30 and aiming canula 30-10, as shown and/or described for previous figures, allow for the passage of interlocking screws through the extra-medullary plate, 34-30 through the humeral stem comprised of outer sheath 23a-50 and inner core 23A-40. Distally distal to the fracture site 24-60 are located screw holes 34-50 through the plate 34-30, once again allowing for alignment between the aiming arm 30-30, the aiming canula 30-10 and the plate screw holes 34-50.

Figure 35A:
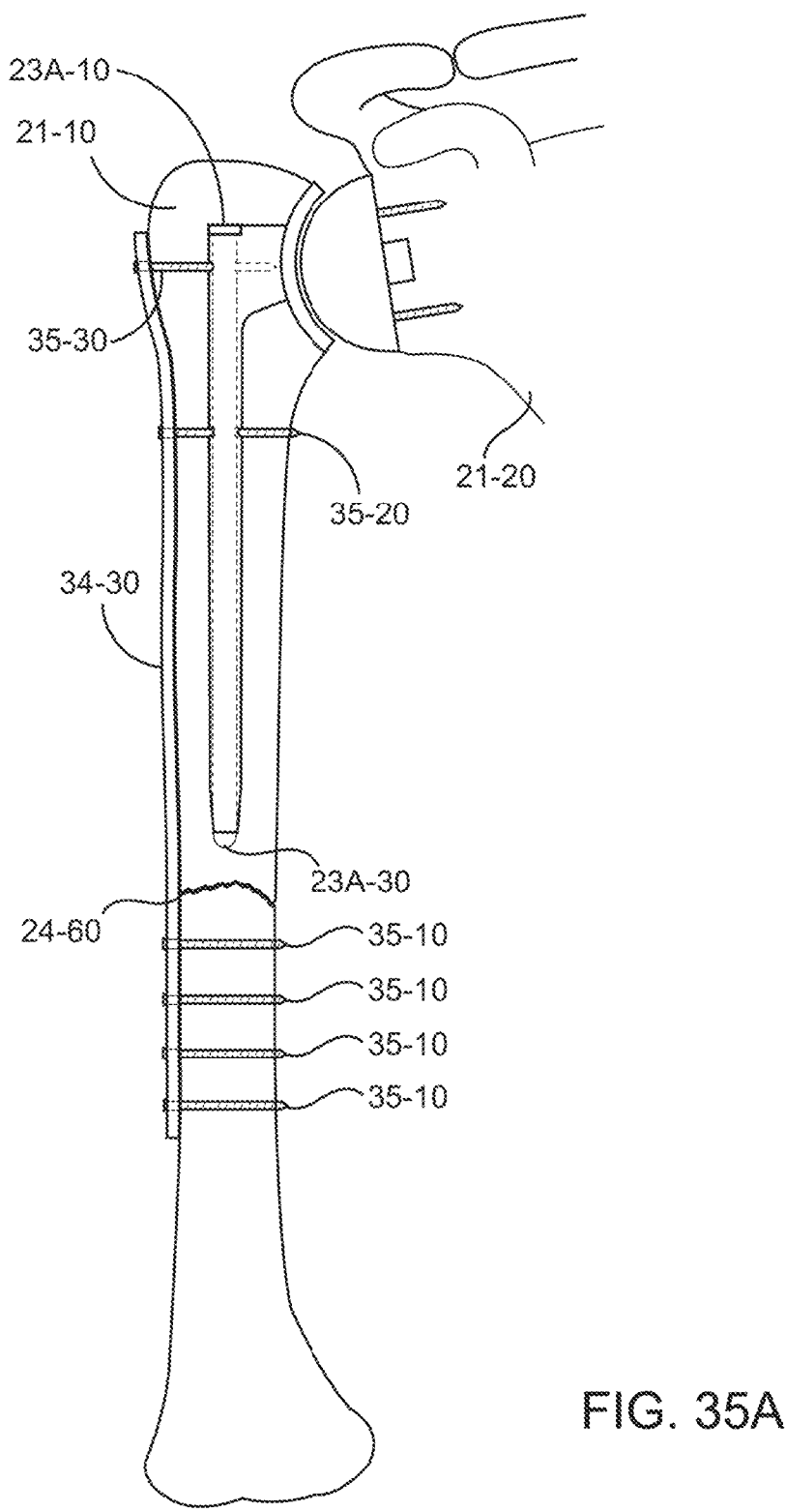
FIG. 35A shows the assembly with screws attached.

FIG. 35A depicts a reverse total shoulder arthroplasty with contingent features for fracture fixation and a final assembly of the extra-medullary fixation plate 34-30 as well as the interlocking screws both proximal and distal to the fracture site 24-60. Screws pass through the plate 34-30 as well as the assembled humeral stem component comprised of outer sheath 23a-50 and inner core 23a-40, utilizing interlocking screws 35-20. These screws, in one embodiment, provide for secure fixation through structures allowing for alignment and rotational stability between plate, bone and humeral stem. Distal to fracture site 24-60 are also depicted interlocking screws passing through the plate 34-30 and the underlying bone. These screws are depicted as 35-10. Finally, a registration screw 35-30 is located in the proximal portion of the humeral arthroplasty component passing through the proximal portion of the plate into the proximal portion of the intact humeral stem component. Design features may include, in one embodiment, appropriate threading to allow for intimate interface between the screw 35-30 and the underlying proximal humeral component.

Figure 35B:
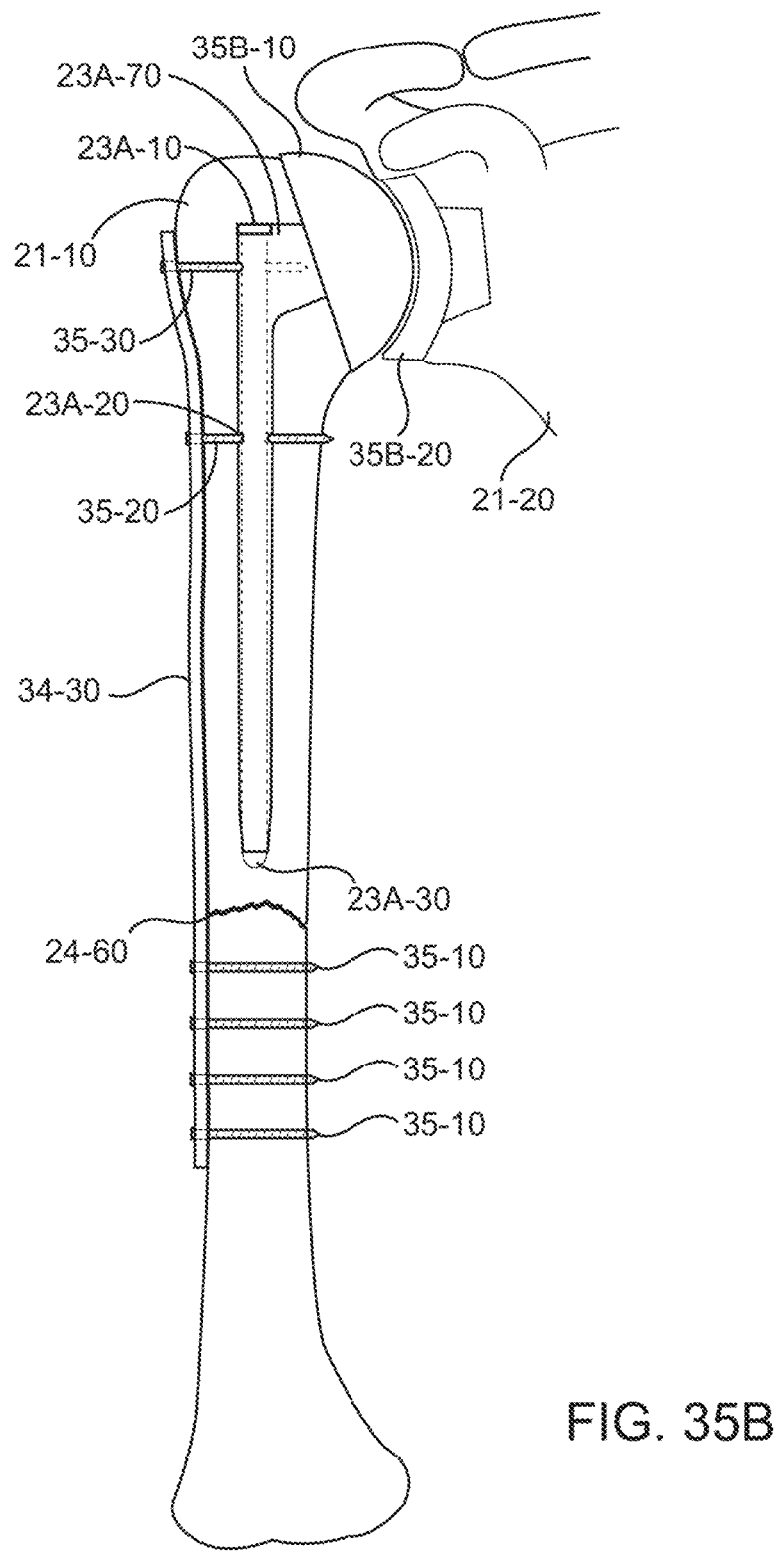
FIG. 35B shows a similar view but with a different joint structure.
Figure 35C:
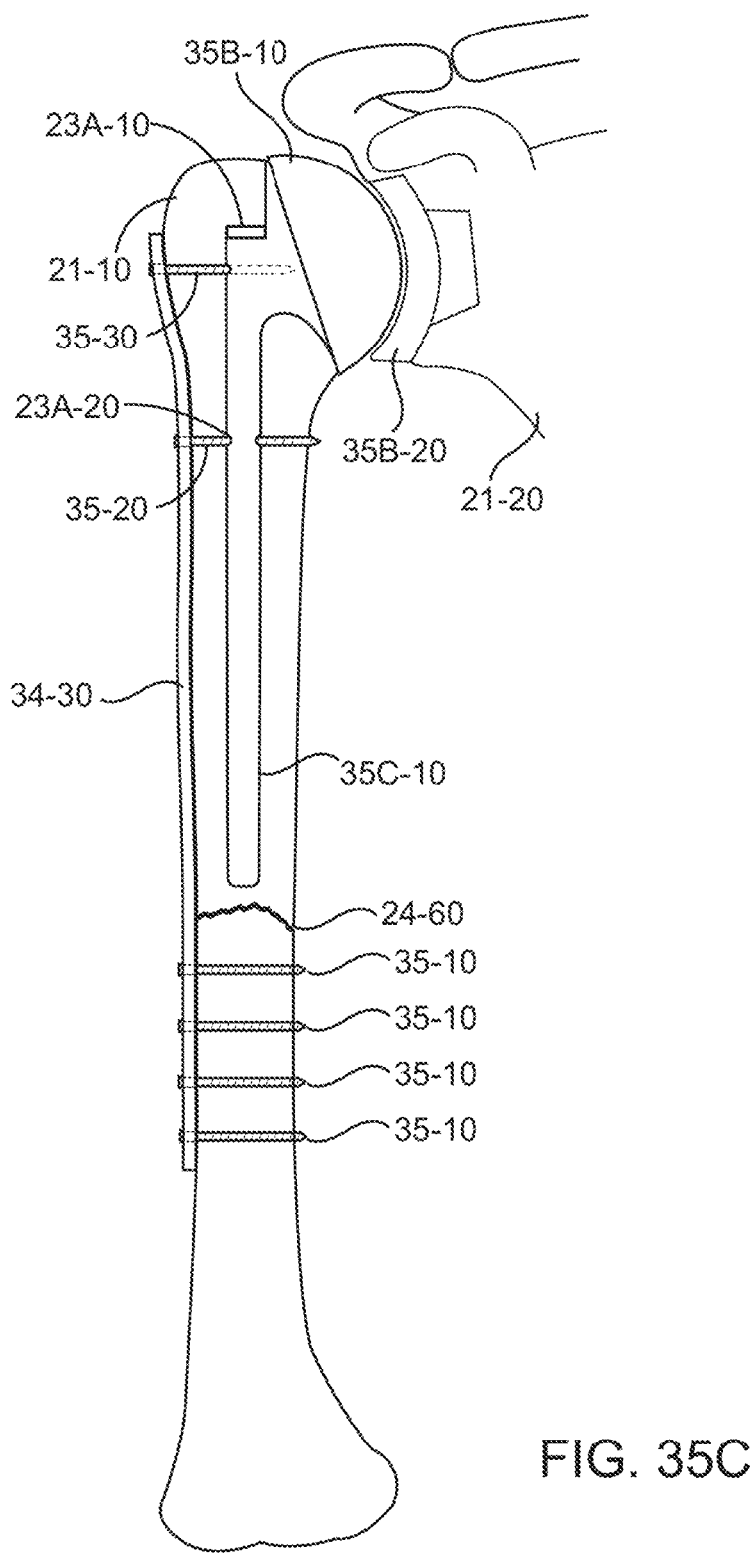
FIG. 35C is yet another embodiment showing fixation fracture fixation with the registered outrigger plate.

FIG. 35B shows an alternative embodiment for a standard total shoulder arthroplasty containing contingent features for fracture fixation. An extra-medullary plate 34-30 is depicted to span the fracture site 24-60. Allowances for interlocking with registration both proximal and distal to the fracture site are noted. Locking screws 35-10 are aligned to pass through the extra-medullary plate 34-30 and anchor into the bone below fracture site 24-60. Proximal to the fracture site 24-60 are noted interlocking screws 35-20. The interlocking screws 35-20 pass through the extra-5 medullary plate 34-30, through the underlying bone as well as through the humeral stem component comprised of outer sheath 23A-50 and inner core 23A-40. The distal extent of the inner core, 23A-40 is shown as 23A-30. The proximal extent of the extra-medullary fixation plate 34-30 is shown with an interfaced interlocking screw 35-30, extending into the proximal portion of the humeral component. One embodiment of this interlocking screw 35-30 is threaded to provide for an intimate interface between the plate 34-30 and the underlying humeral stem component 23A-70. It contains appropriate threat design to allow for interface capabilities between the screw and the intact proximal humeral component. Design features to allow for threading into the underlying humeral fracture FIG. 35C represents an embodiment of an alternative standard total shoulder arthroplasty containing humeral head articular component 35B-10, as well as solid shaft component 35C-10. The alternative embodiment represents a solid humeral stem component 35C-10. This represents standard state-of-the-art humeral component structure with the exception of contingent features 23A-10, representing a novel interface for coupling an extramedullary aiming arm. One example of said aiming arm is depicted at 26-60. Additional features allow for registration and alignment of the extramedullary fixation device 34-30, with the solid core humeral component 35C-10 with similar interfaces allowing for passage of a screw through the extramedullary fixation plate 34-30 and the solid core stem 35C-10. The interface of the interlocking screw through the solid core 35C-10 may be as depicted in FIG. 23A as 23A-20.

Figure 35D:
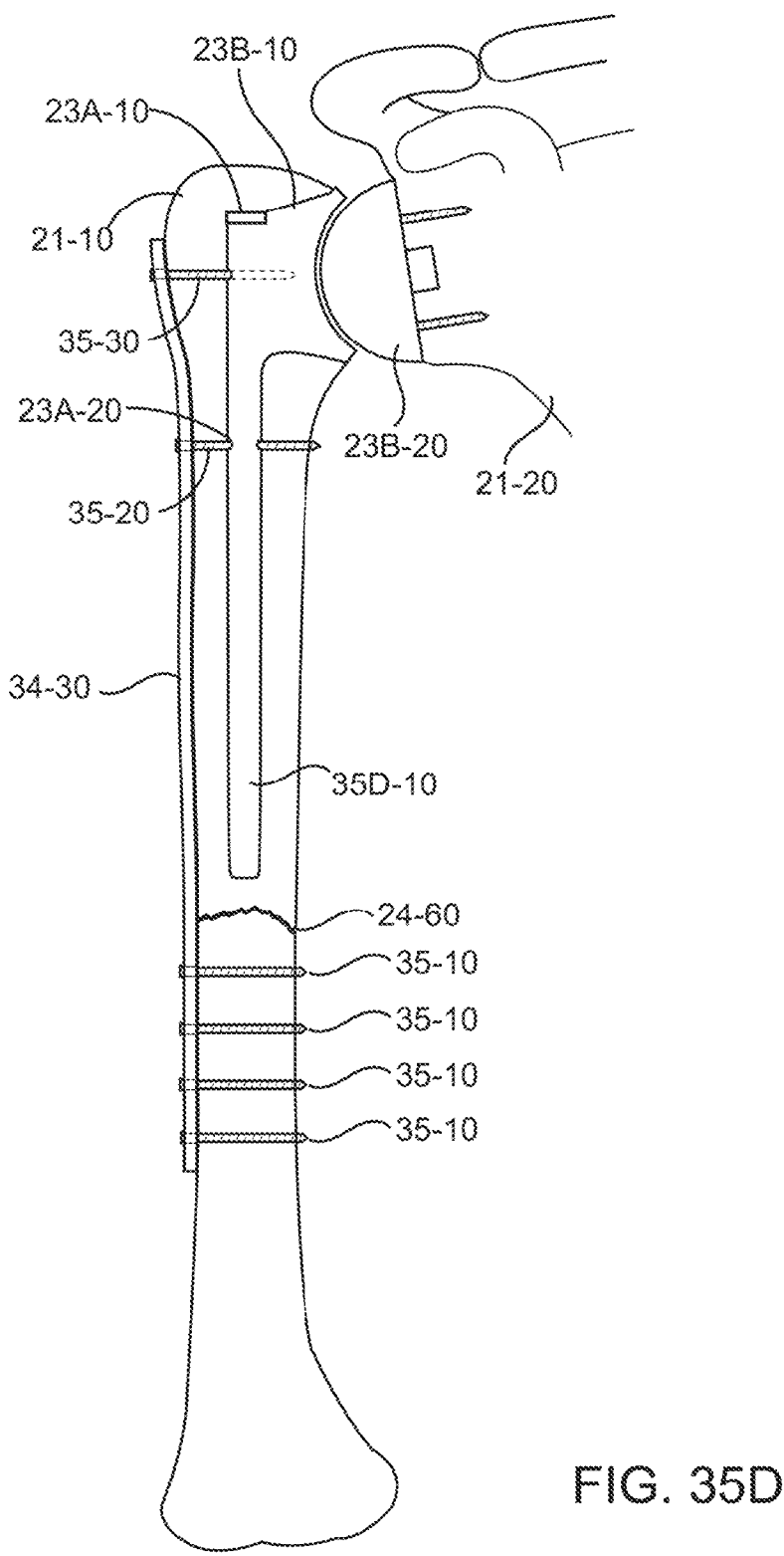
FIG. 35D shows a modified reverse total shoulder arthroplasty with the registered outrigger plate but without a removable core.

FIG. 35D represents an alternative embodiment for a reverse total shoulder arthroplasty containing a solid core humeral shaft component 35D-10 providing a similar unique feature for interface with an extramedullary aiming arm depicted at 23A-10. Extramedullary fixation plate 34-30 interfaces with the solid core humeral stem 35D-10, allowing for passage of interlocking screws 35-30 and 35-20 at interface 23A-20.

Figure 36:
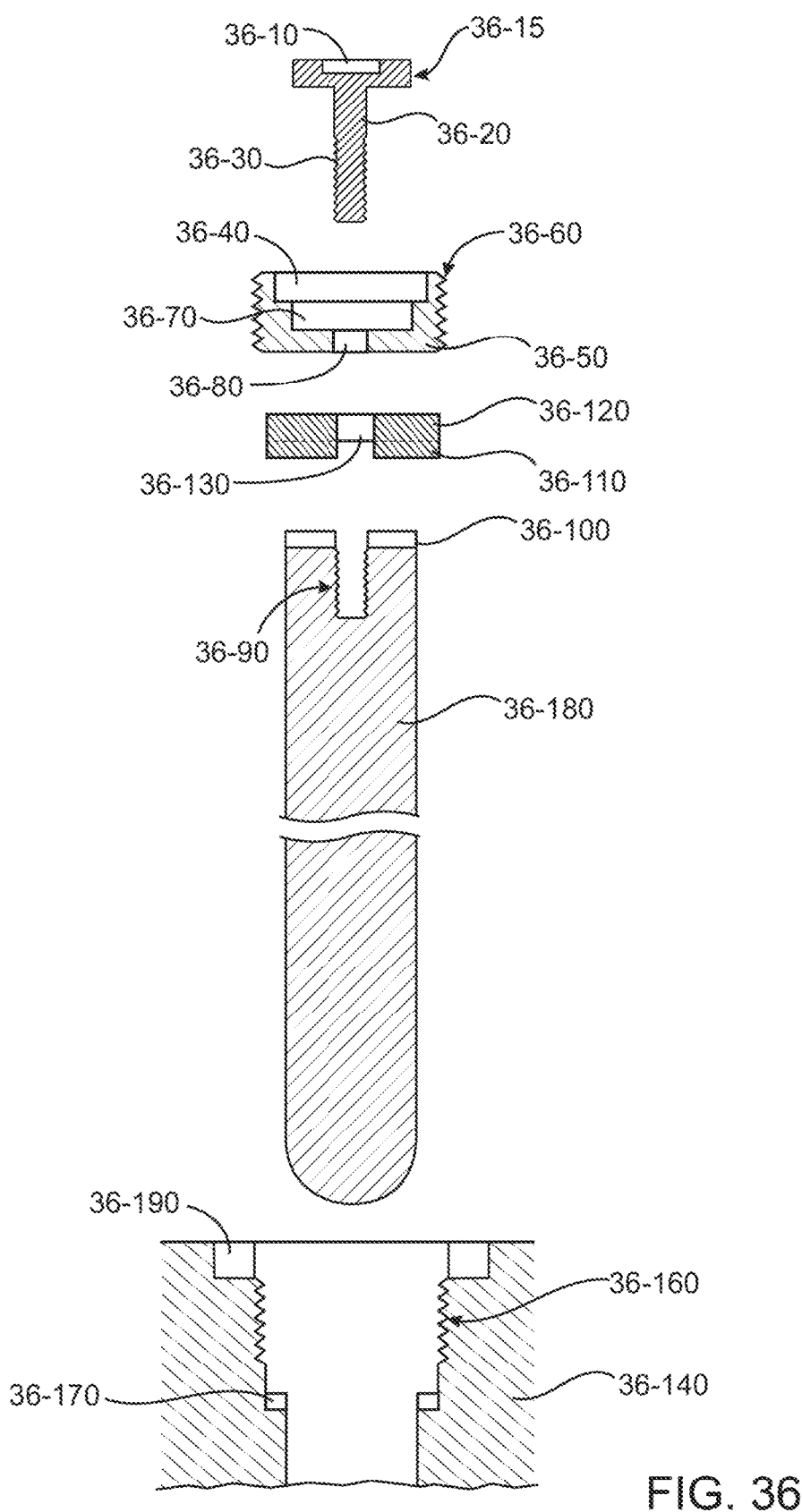
FIG. 36 shows disassembled components of a modified prosthesis.

FIG. 36 represents a disassembled embodiment of the modified prosthesis comprised of parts 36-140 and 36-180. An alternative embodiment of solid core 36-180 is also depicted at 23-40 in another embodiment. Proceeding from top to bottom, first depicted is a locking end cap 36-20, also represented in another embodiment as 23A-10. Locking end cap 36-20 contains a recess for a hex screwdriver 36-10. The threaded tip of the locking end cap allowing for interfacing with solid core 36-180 is represented as 36-30. The interface for these screws is depicted as 36-90. The locking end cap outer diameter 36-50 interfaces with the interface nut 36-50 at the recess depicted as 36-70. Both the recess and the outer diameter of the locking end cap are circular, thus allowing for unencumbered rotation. Again, describing from top to bottom, locking end cap 36-50 passes unencumbered through interface nut 36-50 through opening 36-80. Additionally, locking end cap 36-50 passes unencumbered through registration of washer 36-120 through opening 36-130. Finally, locking end cap 36-15 interfaces with solid core 36-180 through a screw interface between 36-30 and 36-90. This provides for solid coupling and rotational registration. Moving down to interface nut 36-50, two separate recesses are noted, the first at 36-40, which is recessed hex interface to accept a hex screwdriver. The second interface depicted as 36-70 allows for free rotational interface with locking end cap 36-50. The threaded interface on the interface nut is depicted as 36-60. This threads into the intact humeral component at interface 36-160. When this interface is fully engaged, it provides for registration between the registration washer 36-120 and the intact humeral component 36-140 at the registration slot 36-170. Additionally, the registration slot 36-170 aligns with registration slot 36-100 as part of the solid core 36-180. Registration slot 36-170 together with registration slot 36-100 will receive registration thin 36-110 of registration washer 36-120. Once registration thin 36-110 is inserted in the associated registration slots and tightened utilizing tension and compression between locking end cap 36-20 and solid core 36-180, rotational and axial registration is maintained. Finally, humeral component 36-140 contains an additional registration 36-190 allowing for alignment and registration with aiming arm 26-60 in one embodiment. This registration would happen after removal of components 36-20, 36-50, 36-120, and solid core 36-180.

Figure 37A:
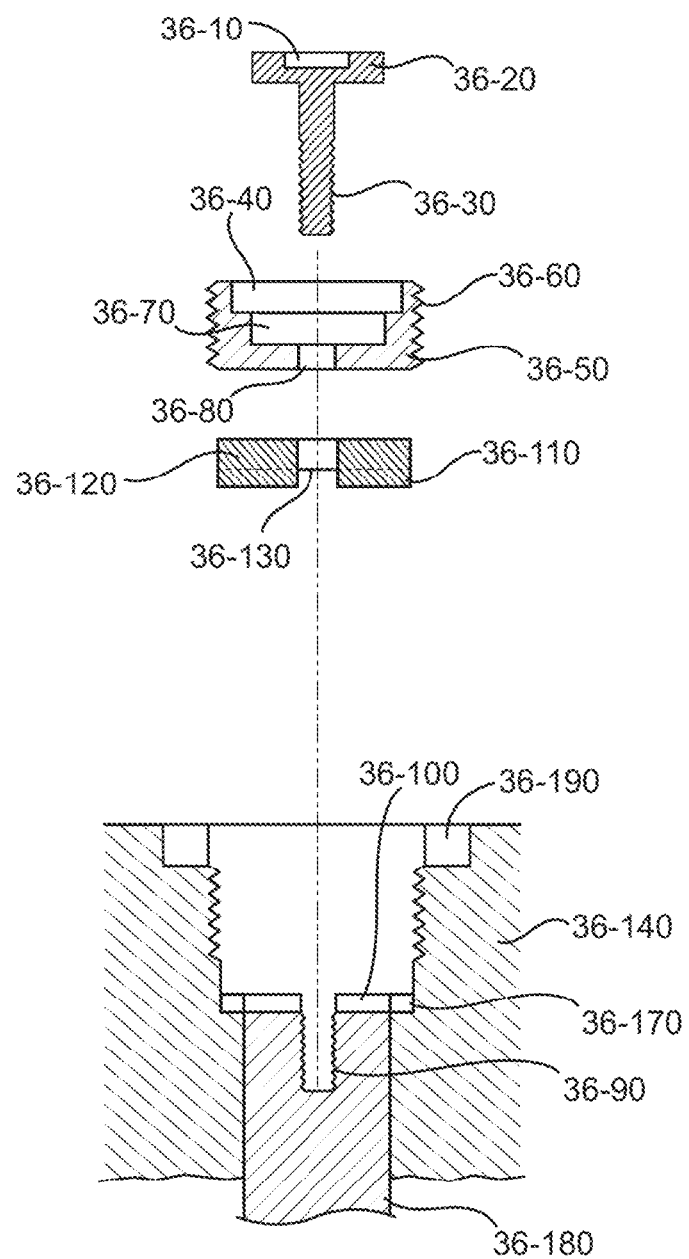
FIGS. 37A, 37B and 37C illustrate a recessed end interface, registration washer and cap.

Turning attention to FIG. 37A, again the recessed end cap interface is depicted as unassembled. Additionally, a cutaway diagram shows the interface between the humeral component solid core 36-180 and the surrounding humeral component 36-140. Registration slots are depicted as 36-100 as well as 36-170. These registration slots are brought into alignment with the use of the registration washer 36-120 and the underlying registration thin 36-110. Further three-dimensional details of the registration washer are also depicted in FIG. 37C.

Figure 37B:
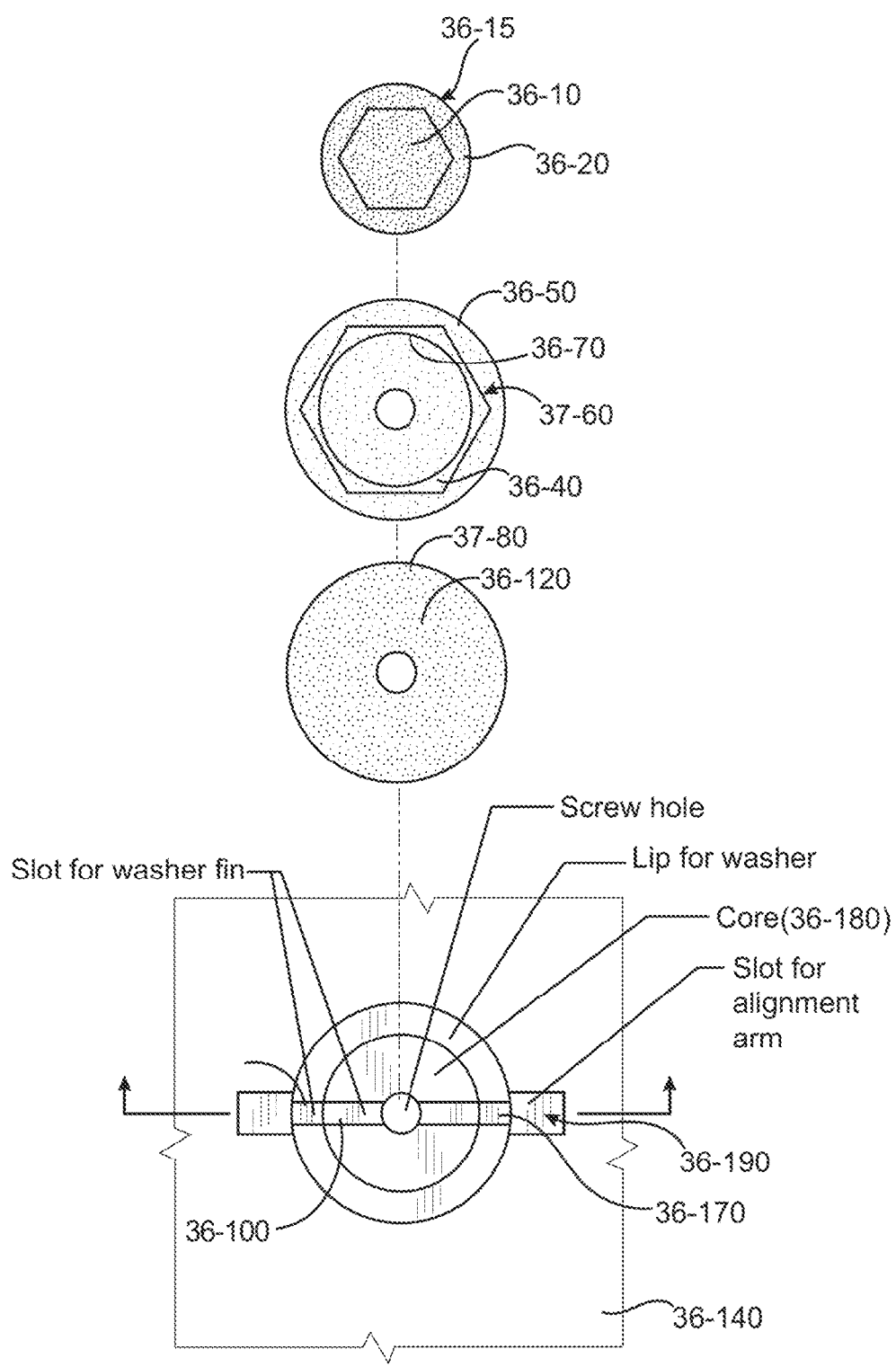
Figure 37C:
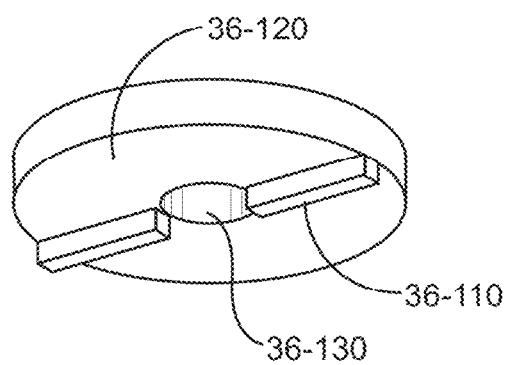

FIG. 37B shows a disassembled recessed end cap interface along with a superior view of the humeral component comprising the outer solid body 36-140 and the inner solid core 36-180. The superior view depicts notches for the aiming arm registration at 36-190. The superior view of the registration slot between the outer humeral component core 36-140 and the inner core component 36-180 is seen allowing for the acceptance of the registration thin 36-110 as a component of the registration washer 36-120. The washer is compressed into place with the placement of the interface nut 36-50. The tightening of the interface occurs with the insertion of a hex screwdriver at the hex notch interface of the interface nut depicted as 37-60. Finally, the locking screw 36-20 is seen from a superior view noting the inner hex recess 36-10 allowing for acceptance of a hex screwdriver. The outer diameter depicted as 36-15 interfaces with the underlying interface nut through the circular interface 36-70. This provides for free, unencumbered rotation allowing for threads 36-30 to tighten and interface with threads 36-90 of the solid humeral core component 36-180. Tightening provides for solid axial and rotational control.

Figure 38A:
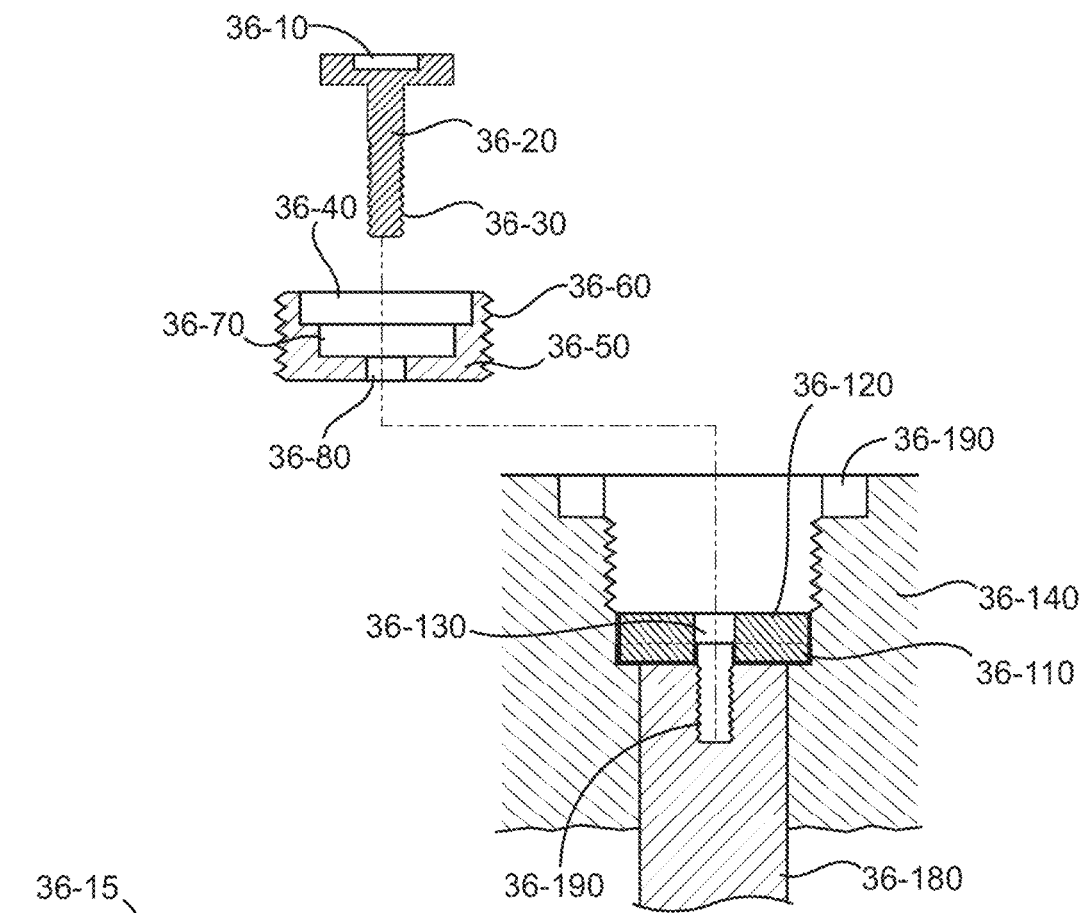
FIGS. 38A and 38B illustrate sequential assembly of an interface.
Figure 38B:
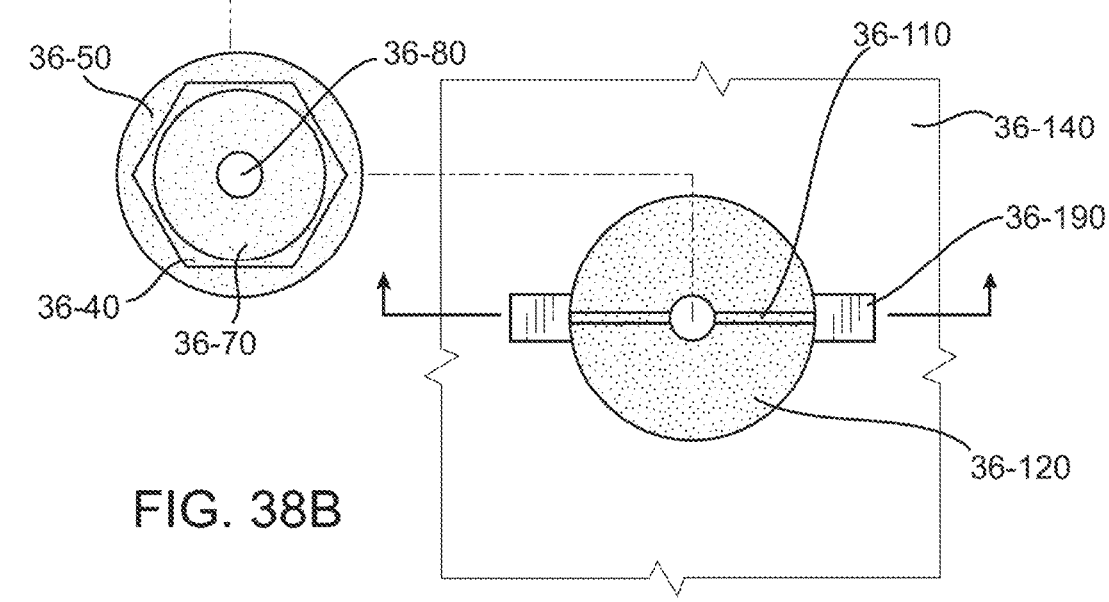

FIGS. 38A and 38B show further sequential assembly of the locking interface analogous to FIGS. 37A and 37B. The registration washer is now shown registering with the intact outer humeral component and the internal solid humeral core through the registration thin 36-110. A cutaway depiction is seen in FIG. 38A with the superior depiction seen in FIG. 38B.

Figure 39A:
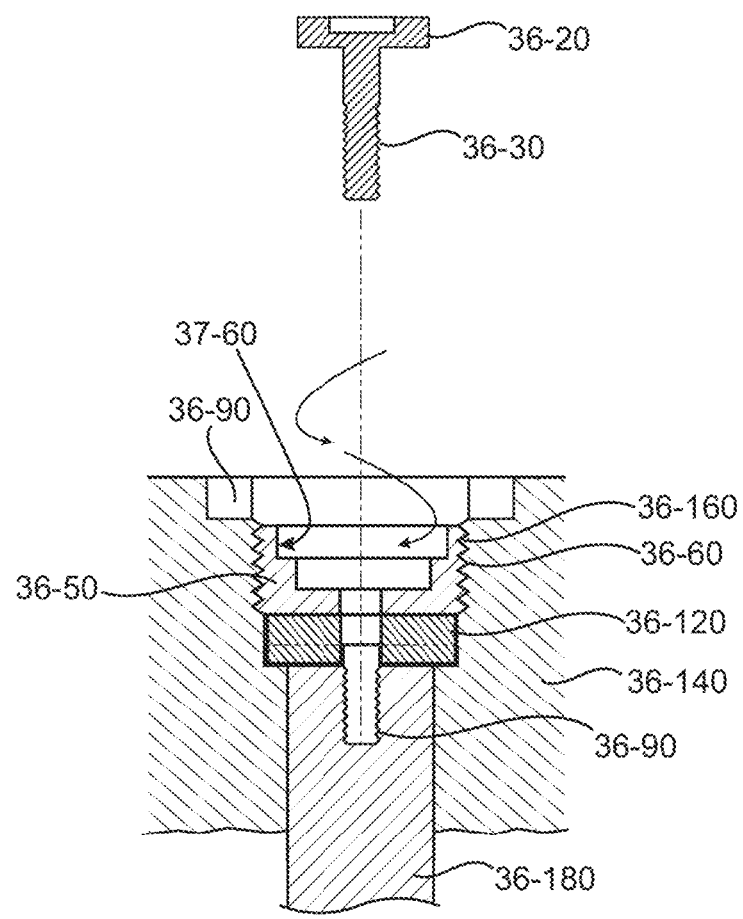
FIGS. 39A and 39B also illustrate further sequential assembly in cutaway and superior views.
Figure 39B:
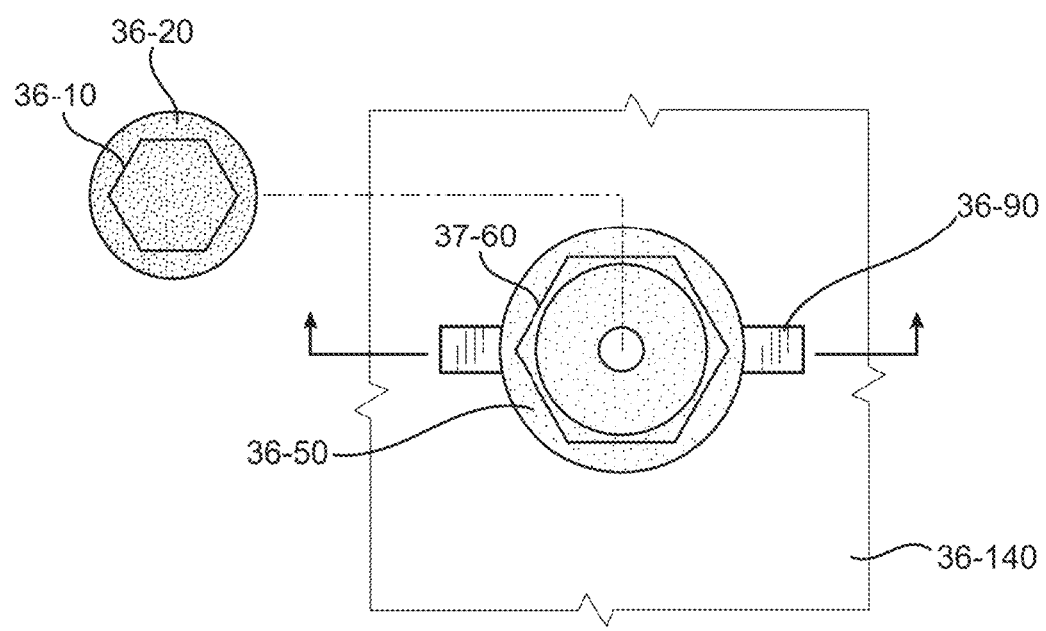

FIGS. 39A and 39B illustrate further sequential assembly in both cutaway and superior views respectively. The interface nut is now inserted and tightened through screw interface 36-160 and 36-60. Insertion of the interface nut and tightening occurs with the use of a hex screwdriver which interfaces at the hex interface 37-60. This is seen again cutaway view in FIG. 39A as well as the superior view in FIG. 39B. Of note, the insertion of the interface nut now provides for compression and registration of the interface washer with the intact humeral component.

Figure 40A:
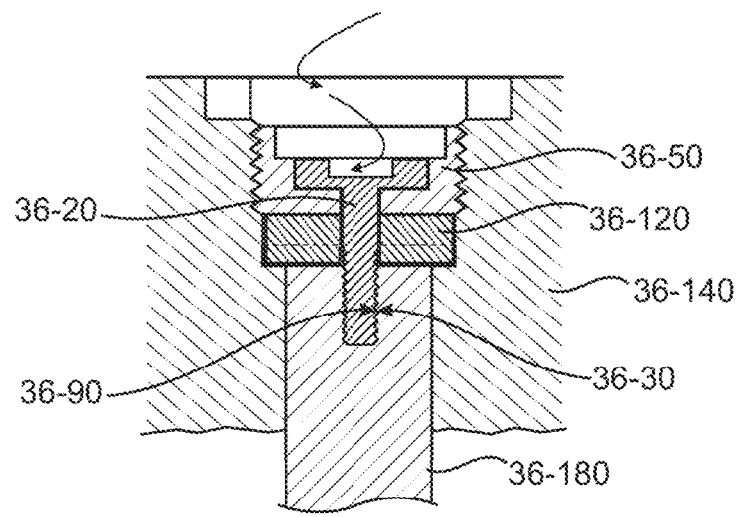
FIG. 40A a cutaway view of recessed locking interface cutaway.
Figure 40B:
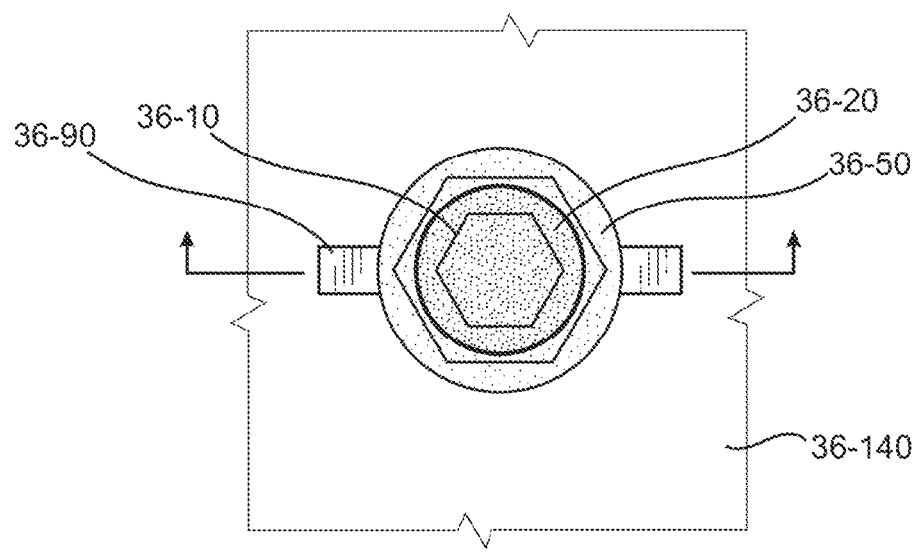
FIG. 40B is superior view for FIG. 40A.

Final assembly of the recessed locking interface is seen in cutaway for FIG. 40A as well as superiorly for FIG. 40B. The locking end cap 36-20 is inserted with the use of a hex screwdriver at the hex interface 36-10. It seats through a thread interface with the native threads of the end cap 36-30 interfacing with the outer threads of the solid core humeral component 36-180 at thread interface 36-90. Of note in FIG. 40B, the superior view, is that the sequential final assembly is seen with the outer registration end cap slot being unobstructed to provide for interface with an aiming arm previously shown in one embodiment as 26-60.

After reading the above text and inspecting the referenced figures, one of ordinary skill in the art would now understand that interface details of FIGS. 36 through 40A and B respectively may be applied to other joint embodiments such as a knee, hip, or elsewhere and are not limited to embodiments of the shoulder alone. Additionally, one of ordinary skill in the art would understand these figures depict only one arrangement for securing the solid core with the prosthesis body and other arrangements may be employed without limitation. As but one example, one depiction is now fully secure and threaded into position at interface 36-30 with the solid core 36-60.

Figure 41:
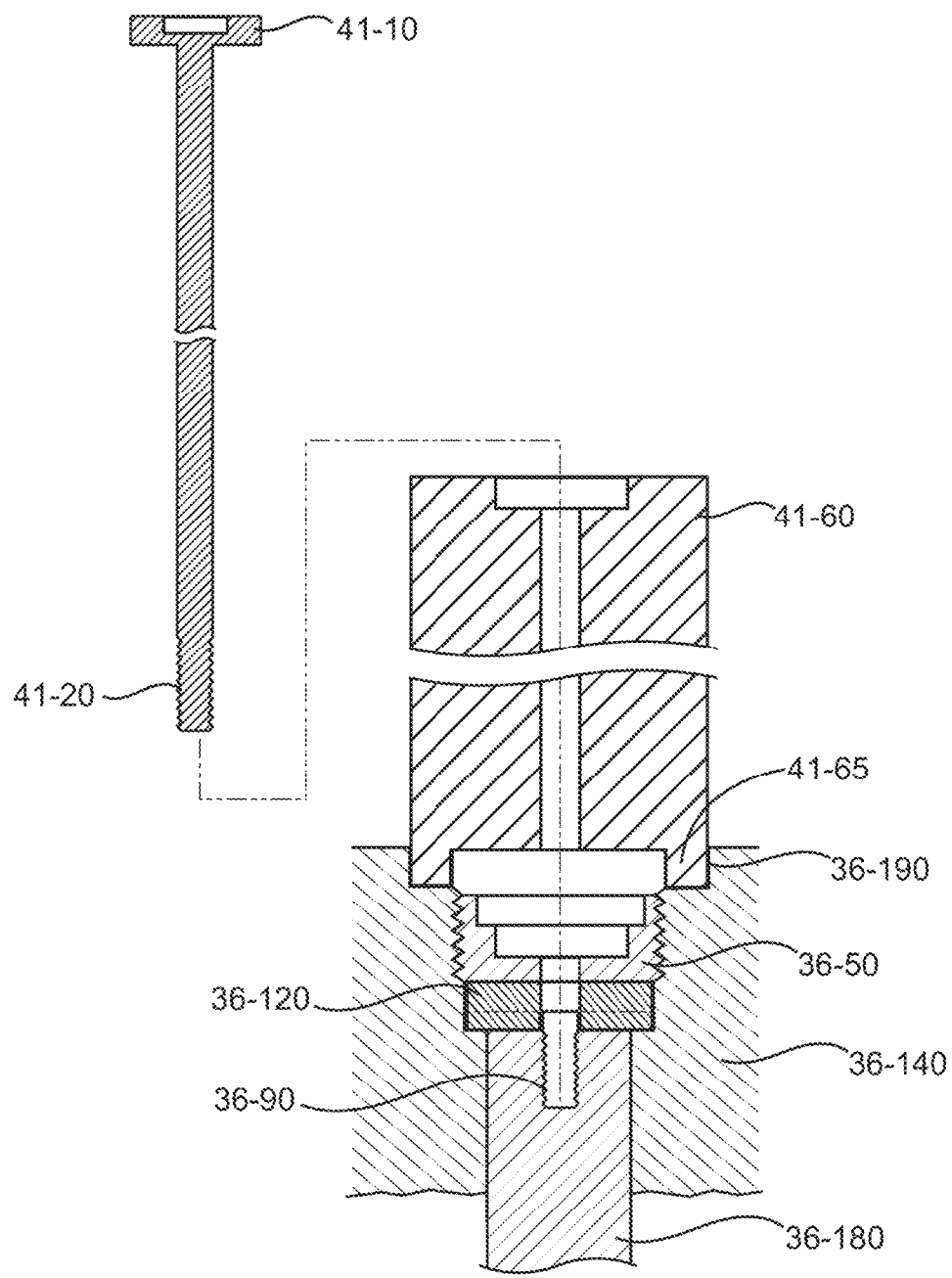
FIG. 41 illustrates attachment of an aiming arm for registration.

FIG. 41 shows attachment of an outer aiming arm 41-60 with a previous embodiment depicted as 26-60. The aiming arm is slotted to provide for registration including axial and rotational control with the intact humeral component 36-140 through slot 36-90. The elongated locking bolt 41-10 passes through aiming arm 41-60 and the final assembly of the recessed end cap interface to thread into the solid humeral component 36-180 with threads 41-20 and threads 36-90. Secure tightening allows for registration to occur at interface registration slot 36-190 of the humeral component and tab 41-65 of the aiming arm.

Figure 42:
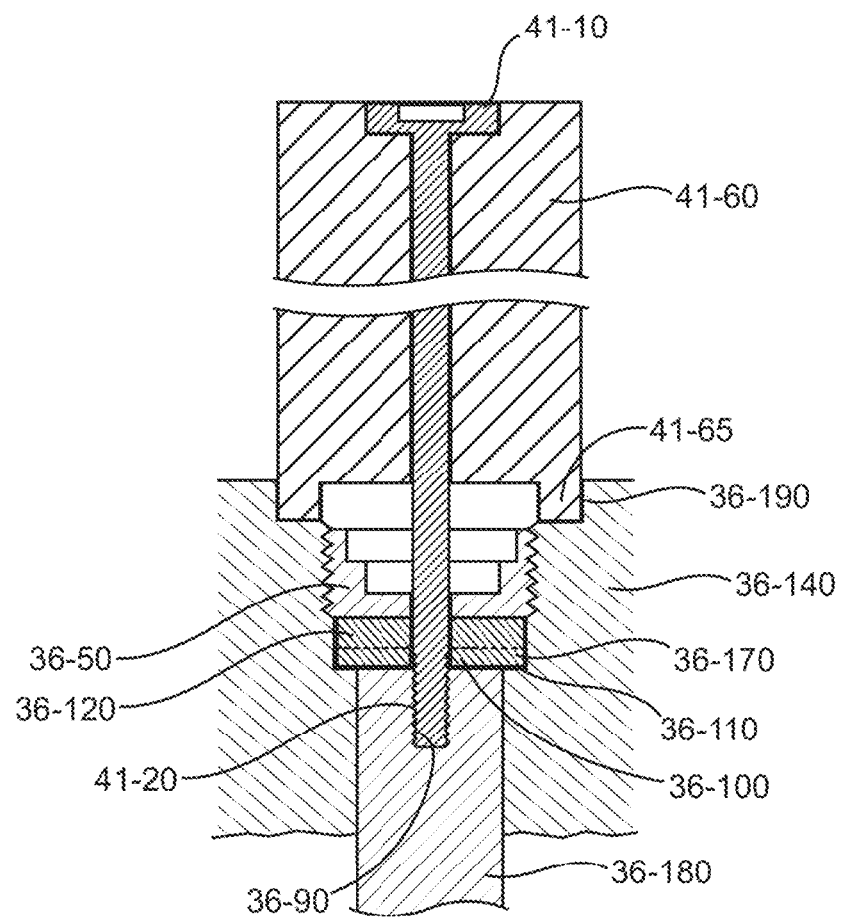
FIG. 42 illustrates assembly of the aiming arm with intact humoral component.

FIG. 42 illustrates assembly of the aiming arm 41-60 with the intact humeral component 36-140. Secure registration occurs with alignment of registration slot 36-190 with registration tab 41-65. Tightening of the elongated locking bolt 41-10 at thread interface 36-90 and 41-20 secures axial and rotational control. In particular, this registration allows for axial and rotational control at interfaces 41-20 and 36-90. The securing of the registration occurs with tightening of elongated locking bolt 41-10 with the intact humeral core component 36-180 through screw interface.

Figure 43:
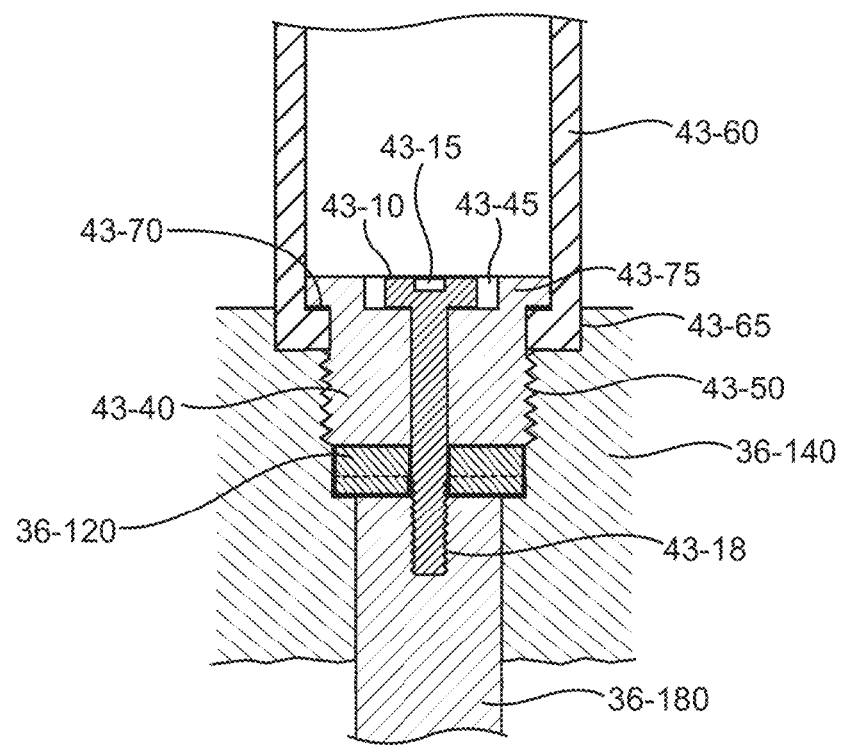
FIG. 43 illustrates another implementation of the outer aiming arm and humeral components.

FIG. 43 is an alternative embodiment of the interface between outer aiming arm 43-60 and humeral component 36-140. The registration for rotational and axial control occurs at 36-190 and 43-65. Reference numeral 43-40 depicts an aligning interface nut that provides for secure fixation and registration between intact humeral component 36-140 and aiming arm 43-60. Free rotation of the aligning interfaced nut 43-40 occurs at interface 43-70. Free rotation at this interface provides for registration of the aiming arm as well as secure fixation of the underlying registration washer 36-120, the intact humeral component 36-140, as well as the solid humeral core component 36-180. Finally, an alternative embodiment of the locking end cap is shown at 43-10. The outer diameter of the locking end cap 43-10 is smaller than the inter-diameter of the aligning interfaced nut 43-40. The gap is shown as 43-45. This provides for the ability to insert a hex screwdriver to interface with 43-40 at the hex interface 43-75. For a hex interface 43-75 to be unencumbered by the outer diameter of the locking end cap 43-10. 43-40 represents an alternative embodiment of the interfaced nut. The interfaced nut provides for compression and secures registration between the underlying humeral core component 36-180, the interface 43-60 and solid humeral component 36-140. Interface between the outer aiming arm 46-36 and threads 36-120. Tightening of elongated locking bolt 41-10 allows for secure registration, both axially and rotationally, between aiming arm 41-60 and intact humeral component 36-140.

Figures 44A, 44B:
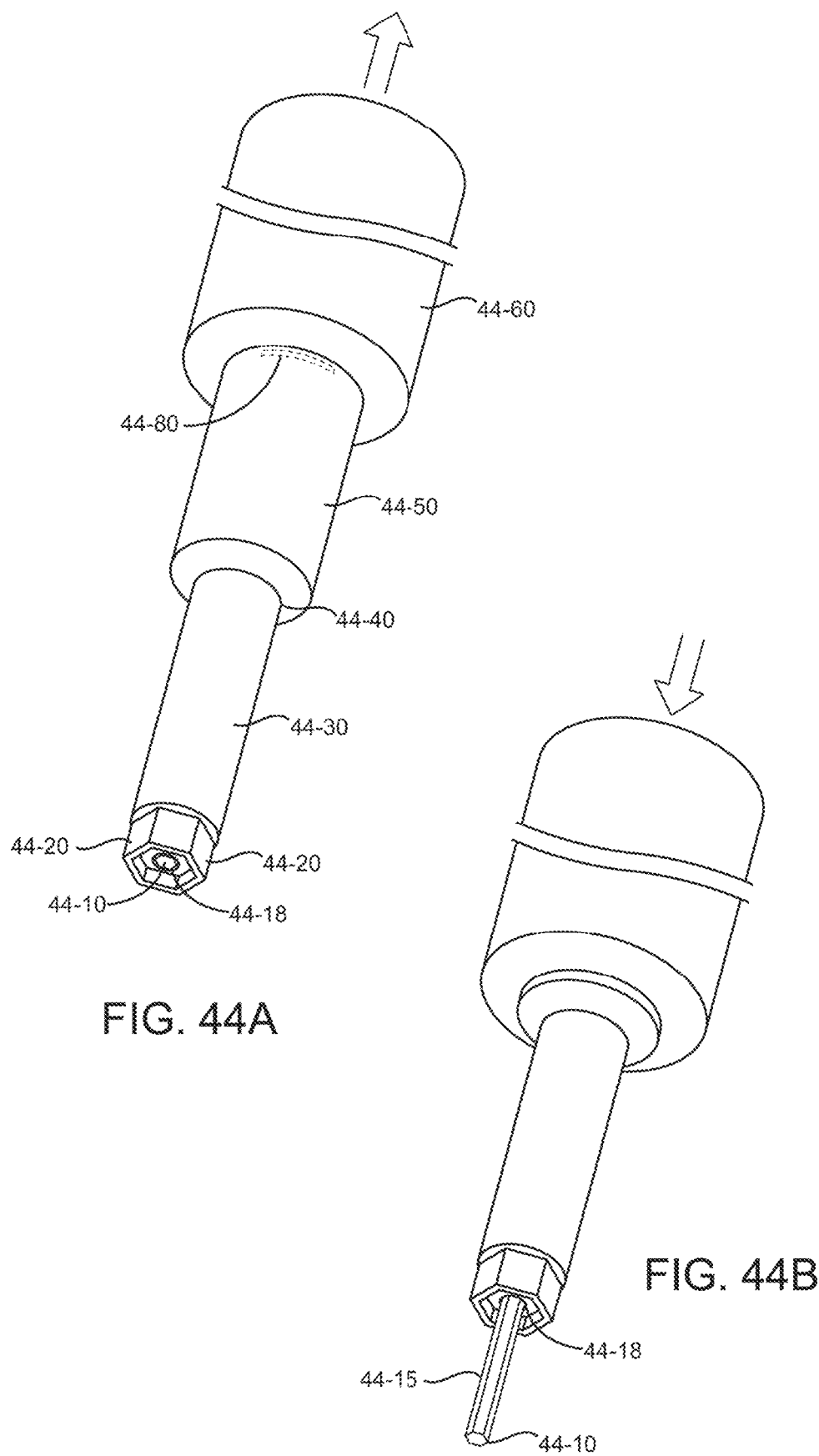
FIGS. 44A and 44B show a telescopic hex fixation tool.

FIGS. 44A and 44B show a telescopic hex fixation tool, including an inner core comprising a smaller hex diameter 44-10 with the proximal rounded shaft 44-15 exiting the outer hex component 44-20 through interface 44-18. The outer core hex component 44-20 interfaces to the rounded shaft at 44-30. The rounded shaft 4430 is solidly coupled to the core handle 44-50 at interface 44-40. The telescopic handle 44-60 is allowed to axially travel over the core handle 44-50 providing for travel of hex component 44-10 into and out of the outer hex 4420 through interface 44-18. Inner body 44-50 at interface 44-40. The telescopic handle 44-60 may traverse a fixed distance.

Note that the provided descriptions of embodiments are for example purposes only to aid in the understanding of the use of the invention. The provided embodiments, figures and discussion should not be construed as limiting the scope or application of the invention contained herein. There are variations and modification to the specific embodiments described which are intended to be included within the scope of this invention.

It should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein. The invention has been described in relation to particular examples, which are intended in all respects to be illustrative rather than restrictive. Those skilled in the art will appreciate that many different combinations of hardware, software, and firmware will be suitable for practicing the present invention. Various aspects and/or components of the described embodiments may be used singly or in any combination. It is intended that the specification and examples be considered as exemplary only, with a true scope and spirit of the invention being indicated by the claims.

While this invention has been particularly shown and described with references to example embodiments thereof, it will be understood by those skilled in the art that various changes in form and details may be made therein without departing from the scope of the invention encompassed by the appended claims.

What is claimed is:

1. A prosthesis comprising:
    a joint interface surface, configured to articulate against a second joint interface surface;
    one or more contingent features integrally disposed on or within the prosthesis;
    a removable contingent component interfaced with at least one of the contingent features; and
    wherein the removable contingent component is further configured to:
        provide access for insertion of a fracture stabilization component within a medullary canal of a shoulder bone in which the prosthesis is configured to reside; and
        expose the one or more contingent features for use in securing the fracture stabilization component with the prosthesis.

2. The prosthesis of claim 1, wherein the removable contingent component is further configured to secure an aligning arm in mechanical registration with both the prosthesis and the fracture stabilization component.

3. The prosthesis of claim 2, wherein the aligning arm is further in mechanical registration with both the prosthesis and the fracture stabilization component, and configured for aligning one or more screws with holes in the prosthesis.

4. The prosthesis of claim 2, wherein the aligning arm is further in mechanical registration with both the prosthesis and the fracture stabilization component, and configured for aligning one or more screws with holes in both the fracture fixation component and the prosthesis.

5. The prosthesis of claim 1 wherein the fracture stabilization component further comprises a humeral sheath.

6. The prosthesis of claim 5 wherein the humeral sheath includes a vacated inner core.

7. The prosthesis of claim 5 wherein the humeral sheath further interfaces to a fixation device that extends beyond a distal extent of a humeral fracture.

8. The prosthesis of claim 1, wherein at least one of the removable contingent components includes one or more interfaces of the prosthesis.

9. The prosthesis of claim 1, wherein the joint interface surface is notched or keyed for rotational alignment in situ.

10. The prosthesis of claim 1 wherein the one or more contingent features include one or more of a pre-engineered notched interface, a pre-engineered threaded interface or a pre-engineered keyed interface.

11. The prosthesis of claim 1, wherein the one or more contingent features are further configured to be located adjacent to a terminal end and within an outer surface layer of a bone within which the prosthesis resides when in situ.

12. A shoulder prosthesis comprising:
a joint interface surface, configured to articulate in situ against a second joint interface surface of a companion joint structure;
one or more contingent features integrally disposed on or within the prosthesis; and
one or more removable contingent components interfaced with at least one of the contingent features, wherein at least one of the removable contingent components is configured to be removable in situ to expose at least one of the contingent features, so that the one or more contingent feature is further configured to both:
secure a fracture stabilization component with the prosthesis; and
secure an aligning arm in mechanical registration with both the prosthesis and the fracture stabilization component.

13. The prosthesis of claim 12, wherein the at least one removable contingent component is further configured to secure the aligning arm in mechanical registration with both the prosthesis and the fracture stabilization component, and to align one or more screws with holes in the fracture stabilization component.

14. The prosthesis of claim 12, wherein the aligning arm is in mechanical registration with both the prosthesis and the fracture stabilization component, and configured to align one or more screws with holes in the prosthesis.

15. The prosthesis of claim 12, wherein the aligning arm is in mechanical registration with both the prosthesis and the fracture stabilization component, and configured for further use to align one or more screws with holes in both the fracture stabilization component and the prosthesis.

16. The prosthesis of claim 12 additionally comprising:
an extra-meduallary fixation device comprising an aiming arm that interfaces with an intact humeral stem component.

17. The prosthesis of claim 16 wherein the extra-medullary fixation device comprises a plate and aiming canula.

18. The prosthesis of claim 17 additionally comprising a proximal locking cap covering the extra-medullary fixation device.

19. The prosthesis of claim 12, wherein at least one of the removable contingent components includes one or more interfaces of the prosthesis.

20. The prosthesis of claim 12, wherein the joint interface surface is notched or keyed for rotational alignment in situ.

21. The prosthesis of claim 12 wherein the one or more contingent features include one or more of a pre-engineered notched interface, a pre-engineered threaded interface or a pre-engineered keyed interface.

22. The prosthesis of claim 12, wherein the one or more contingent features are further configured to be located adjacent to a terminal end and within an outer surface layer of a bone within which the prosthesis resides when in situ.

* * * * *